US008367684B2

(12) United States Patent  
Vernier et al.

(10) Patent No.: US 8,367,684 B2  
(45) Date of Patent: Feb. 5, 2013

(54) DERIVATIVES OF 4-(N-AZACYCLOALKYL) ANILIDES AS POTASSIUM CHANNEL MODULATORS

(75) Inventors: Jean-Michel Vernier, Laguna Niguel, CA (US); Samedy Ouk, Los Angeles, CA (US); Martha A. De La Rosa, San Diego, CA (US)

(73) Assignee: Valeant Pharmaceuticals International, Aliso Viejo, CA (US)

( * ) Notice: Subject to any disclaimer, the term of this patent is extended or adjusted under 35 U.S.C. 154(b) by 1146 days.

(21) Appl. No.: 12/138,251

(22) Filed: Jun. 12, 2008

(65) Prior Publication Data

US 2008/0318979 A1 Dec. 25, 2008

Related U.S. Application Data

(60) Provisional application No. 60/934,396, filed on Jun. 13, 2007.

(51) Int. Cl.
*A01N 43/54* (2006.01)
*A61K 31/505* (2006.01)

(52) U.S. Cl. ......... 514/275; 514/307; 544/324; 546/194

(58) Field of Classification Search .................. 546/122, 546/144
See application file for complete search history.

(56) References Cited

U.S. PATENT DOCUMENTS

| | | | |
|---|---|---|---|
| 4,181,803 | A | 1/1980 | Morita et al. |
| 4,554,281 | A | 11/1985 | vonBebenburg et al. |
| 4,668,684 | A | 5/1987 | Tibes et al. |
| 4,778,799 | A | 10/1988 | Tibes et al. |
| 4,923,858 | A | 5/1990 | Engel et al. |
| 4,923,974 | A | 5/1990 | Ueda et al. |
| 5,032,591 | A | 7/1991 | Evans et al. |
| 5,162,346 | A | 11/1992 | Lobisch et al. |
| 5,234,947 | A | 8/1993 | Cherksey |
| 5,262,419 | A | 11/1993 | Aberg et al. |
| 5,284,861 | A | 2/1994 | Lobisch et al. |
| 5,384,330 | A | 1/1995 | Dieter et al. |

(Continued)

FOREIGN PATENT DOCUMENTS

| | | |
|---|---|---|
| CA | 2542434 | 5/2005 |
| DE | 3337593 | 10/1983 |

(Continued)

OTHER PUBLICATIONS

S.J. Said, Trends in Pharmacological Sciences, 20, 132-134 (1999).*

(Continued)

*Primary Examiner* — James O Wilson
*Assistant Examiner* — Alexander R Pagano
(74) *Attorney, Agent, or Firm* — Jones Day

(57) ABSTRACT

This invention provides potassium channel modulators which are compounds of formula I

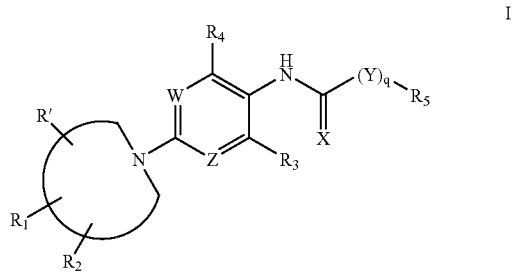

where at least one of W and Z is N;
where the moiety

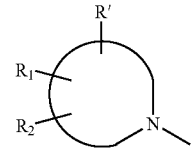

is one of Groups A or B below

A

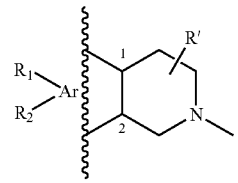

where Ar is a 1,2-fused, six membered ring aromatic group, bearing substituents $R_1$ and $R_2$ as defined below, and containing zero or one ring nitrogen atom; and where other substituents are defined herein.

The invention also provides a composition comprising a pharmaceutically acceptable carrier and at least one of the following: i) a pharmaceutically effective amount of a compound of formula I and ii) a pharmaceutically acceptable salt, ester, or prodrug thereof. The invention also provides a method of preventing or treating a disease or disorder which is affected by activities of potassium channels, comprising administering to a patient in need thereof a therapeutically effective amount of a compound of formula I or a salt, ester, or prodrug thereof.

43 Claims, No Drawings

U.S. PATENT DOCUMENTS

| | | | |
|---|---|---|---|
| 5,428,039 | A | 6/1995 | Cohen |
| 5,502,058 | A | 3/1996 | Mayer et al. |
| 5,643,921 | A | 7/1997 | Grover |
| 5,679,706 | A | 10/1997 | D'Alonzo et al. |
| 5,760,007 | A | 6/1998 | Shank |
| 5,800,385 | A | 9/1998 | Demopulos et al. |
| 5,849,789 | A | 12/1998 | Rostock et al. |
| 5,852,053 | A | 12/1998 | Rostock et al. |
| 5,858,017 | A | 1/1999 | Demopulos et al. |
| 5,860,950 | A | 1/1999 | Demopulos et al. |
| 5,914,425 | A | 6/1999 | Meisel et al. |
| 5,925,634 | A | 7/1999 | Olney |
| 5,965,582 | A * | 10/1999 | Lebaut et al. ............. 514/338 |
| 6,117,900 | A | 9/2000 | Rundfeldt et al. |
| 6,211,171 | B1 | 4/2001 | Sawynok et al. |
| 6,218,411 | B1 | 4/2001 | Koga |
| 6,265,417 | B1 | 7/2001 | Carroll et al. |
| 6,281,211 | B1 | 8/2001 | Cai et al. |
| 6,326,385 | B1 | 12/2001 | Wickenden et al. |
| 6,348,486 | B1 | 2/2002 | Argentieri et al. |
| 6,395,736 | B1 | 5/2002 | Parks et al. |
| 6,451,857 | B1 | 9/2002 | Hurtt et al. |
| 6,469,042 | B1 | 10/2002 | Hewawasam et al. |
| 6,472,165 | B1 | 10/2002 | Rundfeldt et al. |
| 6,495,550 | B2 | 12/2002 | McNaughton-Smith et al. |
| 6,500,455 | B1 | 12/2002 | Frantsits |
| 6,537,991 | B1 | 3/2003 | Shaw et al. |
| 6,538,004 | B2 | 3/2003 | Drizin |
| 6,538,151 | B1 | 3/2003 | Meisel et al. |
| RE38,115 | E | 5/2003 | Smith et al. |
| 6,589,986 | B2 | 7/2003 | Bowlby et al. |
| 6,593,335 | B1 | 7/2003 | Carroll |
| 6,642,209 | B1 | 11/2003 | Fukunaga |
| 6,645,521 | B2 | 11/2003 | Cassel |
| 6,737,422 | B2 | 5/2004 | McNaughton-Smith et al. |
| 6,831,087 | B2 * | 12/2004 | Alanine et al. ............. 514/307 |
| 7,045,551 | B2 | 5/2006 | Wu et al. |
| 7,160,684 | B2 | 1/2007 | Argentieri et al. |
| 7,309,713 | B2 | 12/2007 | Rundfeldt et al. |
| 7,419,981 | B2 | 9/2008 | Field et al. |
| 2002/0013349 | A1 | 1/2002 | Wickenden |
| 2002/0015730 | A1 | 2/2002 | Hoffmann et al. |
| 2002/0183395 | A1 | 12/2002 | Argentieri |
| 2004/0198724 | A1 | 10/2004 | McNaughton-Smith et al. |
| 2005/0089473 | A1 | 4/2005 | Black et al. |
| 2005/0089559 | A1 | 4/2005 | Szelenyi et al. |
| 2005/0090547 | A1 | 4/2005 | Szelenyi et al. |
| 2005/0202394 | A1 | 9/2005 | Dobson |
| 2005/0277579 | A1 | 12/2005 | Krishnan et al. |
| 2007/0066612 | A1 | 3/2007 | Khanzhin et al. |
| 2009/0170885 | A1* | 7/2009 | Vernier et al. ............. 514/275 |
| 2011/0039827 | A1* | 2/2011 | Blackburn et al. ...... 514/217.01 |
| 2011/0104315 | A1* | 5/2011 | Sun et al. ............. 424/757 |

FOREIGN PATENT DOCUMENTS

| | | |
|---|---|---|
| DE | 3604575 A1 | 8/1986 |
| DE | 103 49 729.3 | 10/2003 |
| DE | 103 59 335 | 5/2005 |
| EP | 189788 A1 | 8/1986 |
| EP | 0 343 429 | 5/1989 |
| EP | 1 334 972 | 8/2003 |
| EP | 1 407 768 | 4/2004 |
| EP | 1 813 285 A1 | 8/2007 |
| JP | 2000 14350 | 5/2000 |
| JP | 2000 143510 A | 5/2000 |
| RU | 2006117525 | 12/2005 |
| WO | WO 00/55137 | 9/2000 |
| WO | WO 00/59487 A2 | 10/2000 |
| WO | WO 00/59508 A1 | 10/2000 |
| WO | WO 01/01970 | 1/2001 |
| WO | WO 01/01972 A2 | 1/2001 |
| WO | WO 01/09612 | 2/2001 |
| WO | WO 01/22953 A2 | 4/2001 |
| WO | WO 02/080898 | 10/2002 |
| WO | WO 03/020706 | 3/2003 |
| WO | WO 03/097586 | 11/2003 |
| WO | WO 03/106454 A1 | 12/2003 |
| WO | WO 2004/058739 | 7/2004 |
| WO | WO 2004/080950 | 9/2004 |
| WO | WO 2004/082677 | 9/2004 |
| WO | WO 2004/096767 | 11/2004 |
| WO | WO 2004/105795 | 12/2004 |
| WO | WO 2005/039576 A1 | 5/2005 |
| WO | WO 2005/048975 | 6/2005 |
| WO | WO 2005/087754 | 9/2005 |
| WO | WO 2005/100349 | 10/2005 |
| WO | WO 2006/029623 | 3/2006 |
| WO | WO 2006/092143 | 9/2006 |
| WO | WO 2008/024398 | 2/2008 |
| WO | WO 2008/066900 | 6/2008 |

OTHER PUBLICATIONS

C-C. Shieh, et al. 52 Pharmacological Reviews, 557-593, 557 (2000).*
Z. Wang., Potassium Channels: Oncogenic Potential and Therapeutic Target for Cancers in, 3 Topics in Medicinal Chemistry 55-89, 59 (P. R. Bernstein et al., eds, 2008).*
A.M. Traynor et al., Drugs of Today, 40(8), 697-710, 698 (2004).*
F.F. De Arruda, et al., Int. J. Radiation Oncology Biol. Phys., 64(2), 363-373 (2006).*
A.K. Rustgi, Molecular Biology of the Esophagus and Stomach, in 1 Cancer Principles & Practice of Oncology 989-993, 991 (V.T. DeVita, Jr. et al. eds., 8th ed., 2008).*
B.C. Bastian, Genetic Progression, in From Melanocytes to Melanoma the Progression to Malignancy 197, 201 (V. J. Hearing et al., eds., 2006).*
L. Pusztai, Histopathologic and Molecular Markers of Prognosis and Response to Therapy, in Breast Cancer 324, 326-328 (Kelly k. Hunt et al., ed., 2nd ed., 2008).*
S. Cannistra et al, Ovarian Cancer, Fallopian Tube Carcinoma and Peritoneal Carcinoma in, 2 Cancer Principles & Practice of Oncology 1568 (V.T. DeVita, Jr. et al. eds., 8th ed., 2008).*
K. Odunsi et al, Molecular Biology of Gynecological Cancers, in 2 Cancer Principles & Practice of Oncology 1487, 1492 (V.T. DeVita, Jr. et al. eds., 8th ed., 2008).*
S.K. Libutti, Colon Cancer in, 1 Cancer Principles & Practice of Oncology 1232, 1243 (V.T. DeVita, Jr. et al. eds., 8th ed., 2008).*
J.H. Poupaert, Drug Design: Basic Principles and Applications, in 2 Encyclopedia of Pharmaceutical Technology 1362-1369, 1367 (James Swarbrick ed., 3rd ed., 2007).*
L.I. Zon et al., Nature Reviews Drug Discovery 4, 35 (2005).*
A. Kamb, Nature Reviews Drug Discovery 2, 161-165 (2005).*
N.F. Smith, Molecular Cancer Therapeutics, 6, 428-440, 428 (2007).*
N. E. Sharpless et al., Nature Reviews Drug Discovery 5, 741-754, 742 (2006).*
A.T. Hawley et al., Etiology of Cancer: Cancer Susceptibility Syndromes, in 2 Cancer Principles & Practice of Oncology 157-168, 157 (V.T. DeVita, Jr. et al. eds., 8th ed., 2008).*
G.C. Terstappen, 272 Analytical Biochemistry, 149-155, 150 (1999).*
Abad-Zapatero, Drug Discovery Today, 1-8 (2010).*
K.P. Olive et al., Clinical Cancer Research 12, 5277-5287 (2006).*
I. Collins, Current Signal Transduction Therapy, 1, 13-23, 13 (2006).*
Y. Song et al., Cancer a Conceptual Framework in, 1 Cancer Principles & Practice of Oncology 1, 5-6 (V.T. DeVita, Jr. et al. eds., 8th ed., 2008).*
B. Hann et al., Current Opinion in Cell Biology, 13, 778-784 (2001).*
K. G. Chen et al., How Melanoma Cells Evade Chemotherapy, in From Melanocytes to Melanoma the Progression to Malignancy 591 (V. J. Hearing et al., eds., 2006).*
Armand et al., "Effects of retigabine (D-23129) on different patterns of epileptiform activity induced by 4-aminopyridine in rat entorhinal cortex hippocampal slices," *Naunyn-Schmiedeberg's Arch Pharmacol* 359:33-39 (1999).
Armijo et al., "Ion channels and epilepsy," *Curr Pharm Des.* 11:1975-2003 (2005).
Barhanin, M., et al., "$K_vLQT1$ and ISK (minK) proteins associate to form the $I_{Ks}$ cardiac potassium current," *Nature* 384(6604):78-80 (1996).

Beeby et al. "The synthesis and properties of 2:7-Disubstituted 1:2:3:4-tetrahydroisoquinolines," *J. Chem. Soc.*¶ 385, 1799-1803 (1949).

Bialer et al., "Progress report on new antiepileptic drugs: a summary of the fourth Eilat conference (EILAT IV)," *Epilepsy Res*. 34:1-41 (1999).

Bialer, "Progress report on new antiepileptic drugs: a summary of the Sixth Eilat Conference (EILAT VI)," *Epilepsy Res*. 51:31-71 (2002).

Bialer, "Progress report on new antiepileptic drugs: a summary of the Seventh Eilat Conference (EILAT VII)," *Epilepsy Res*. 61:1-48 (2004).

Biervert et al., "A potassium channel mutation in neonatal human epilepsy," *Science* 279:403-406 (1998).

Blackburn-Munro and Jensen, "The anticonvulsant retigabine attenuates nociceptive behaviours in rat models of persistent and neuropathic pain," *Eur J Pharmacol*. 460:109-116 (2003).

Brown and Adams, "Muscarinic suppression of a novel voltage-sensitive $K^+$ current in a vertebrate neurone," *Nature* 283:673-676 (1980).

Brown, D.A., *Ion Channels*, T. Narahashi, Ed. (Plenum Press, New York) pp. 55-94 (1988).

Charlier et al., "A pore mutation in a novel KQT-like potassium channel gene in an idiopathic epilepsy family," *Nat Genet*. 18:53-55 (1998).

Cooper et al., "Colocalization and coassembly of two human brain M-type potassium in channel subunits that are mutated in epilepsy." *Proc Natl Acad Sci USA* 97:4914-4919 (2000).

Delmas and Brown, "Pathways modulating neural KCNQ/M (Kv7) potassium channels," *Nat Rev Neurosci*. 6:850-862 (2005).

Dickenson al., "Neurobiology of neuropathic pain: mode of action of anticonvulsants," *Eur. J. Pain* 6:51-60 (2002).

Dost et al., "The anticonvulsant retigabine potently suppresses epileptiform discharges in the low Ca ++ and low Mg++ model in the hippocampal slice preparation," *Epilepsy Res*. 38:53-56 (2000).

Friedel and Fitton, "Flupirtine: a review of its analgesic properties, and therapeutic efficacy in pain states," *Drugs* 45:548-569 (1993).

Hiller et al., "Retigabine N-glucuronidation and its potential role in enterohepatic circulation," *Drug Metab Dispos*. 27(5):605-612 (1999).

Hunt and Mantyh, "The molecular dynamics of pain control," *Nat Rev Neurosci*.2:83-91 (2001).

Jentsch, "Neuronal KCNQ potassium channels; physiology and role in disease," *Nat. Rev Neurosci.*, 1:21-30 (2000).

Jiang et al., "X-ray structure of a voltage-dependent K+ channel," *Nature* 423:33-41 (2003).

Kharkovets et al., "Mice with altered KCNQ4 $K^+$ channels implicate sensory outer hair cells in human progressive deafness," *EMBO J* 25:642-652 (2006).

Kibbe *Handbook of Pharmaceutical Excipients* (Pharmaceutical Press, London) (2000).

Kubisch et al., "KCNQ4, a novel potassium channel expressed in sensory outer hair cells, is mutated in dominant deafness," *Cell* 96:437-446 (1999).

Lamas et al., "Effects of a cognition-enhancer, linopirdine (DuP 996), on M-type potassium currents ($I_{K(M)}$) and some other voltage- and ligand-gated membrane currents in rat sympathetic neurons," *Eur. J Neurosci.*, 9:605-616 (1997).

Lee et al., "Structure of the KvAP voltage-dependent $K^+$ channel and its dependence on the lipid membrane," *Proc Natl Acad Sci USA* 102:15441-15446 (2005).

Long et al., "Crystal Structure of a mammalian voltage-dependent *Shaker family* $K^+$ channel," *Science* 309:897-903 (2005).

Main et al., "Modulation of KCNQ2/3 potassium channels by the novel anticonvulsant retigabine," *Mol. Pharmacol*. 58:253-262 (2000).

Marrion, "Control of M-currents," *Annu Rev Physiol*. 59:483-504 (1997).

Parcej and Eckhardt-Strelau, Structural characterization sensitive of neuronal voltage-sensitive $K^+$ channels heterologously expressed in *Pichia pastoris, J Mol Biol* 333:103-116 (2003).

Passmore et al., "KCNQ/M currents in sensory neurons: significance for pain therapy," *J. Neurosci*. 23:7227-7236 (2003).

Porter et al., "Retigabine," *Neurotherapeutics* 4:149-154 (2007).

Reich et al., "Design and synthesis of novel 6,7-imidazotetrahydroquinoline inhibitors of thymidylate synthase using iterative protein crystal structure analysis," *J. Med. Chem*. 35:847-858 (1992).

Rogawski, MA, "KCNQ2/KCNQ3 K+ channels and the molecular pathogenesis of epilepsy: implications for therapy," *Trends Neurosci*. 23:393-398 (2000).

Rostock et al., "A new anticonvulsant with broad spectrum activity in animal models of epileptic seizures," *Epilepsy Res*.23:211-223 (1996).

Rundfeldt et al., "Multiple actions of the new anticonvulsant D-23129 on voltage-gated inward currents and GABA-induced currents in cultured neuronal cells (abstract)," *Naunyn-Schmiedeberg's Arch Pharmacol* 351 (Suppl):R160 (1995).

Rundfeldt, "Characterization of the $K^+$ channel opening effect of the anti-convulsant retigabine in PC12 cells," *Epilepsy Res*.35:99-107 (1999).

Rundfeldt, "The new anticonvulsant retigabine (D23129) acts as an opener of $K^+$ channels in neuronal cells," *Eur J Pharmacol*. 336:243-249 (1997).

Schroeder et al., "KCNQ5, a novel potassium channel broadly expressed in brain, mediates M-type currents," *J. Biol. Chem*. 275:24089-24095 (2000).

Schroeder, "Moderate loss of function of cyclic-AMP-modulated KNCQ2/KCNQ3 $K^+$ channels causes epilepsy," *Nature* 396:687-690 (1998).

Singh et al., "A novel potassium channel gene, KCNQ2, is mutated in an inherited epilepsy of newborns," *Nat Genet*. 18:25-29 (1998).

Suzuki and Dickenson, "Neuropathic pain: nerves bursting with excitement," *NeuroReport* 11:R17-R21 (2000).

Tatulian and Brown, "Effect of the KCNQ potassium channel opener retigabine on single KCNQ2/3 channels express in CHO cells," *J Physiol*. 549:57-63 (2003).

Tatulian et al., "Activation of expressed KCNQ potassium currents and native neuronal M-type potassium currents by the anti-convulsant drug retigabine," *J. Neurosci*. 21:5535-5545 (2001).

Tober et al., "D-23129: a potent anticonvulsant in the amygdala kindling model of complex partial seizures," *Eur J Pharmacol*, 303:163-169 (1996).

Von Bebenburg et al., "Substituierte Polyaminopyridine" *Chemiker-Zeitung* 103:387-399 (1979). (German language article attached.).

Wang et al., KCNQ2 and KCNQ3 potassium channel subunits: molecular correlates of the M-channel, *Science* 282:1890-1893 (1998).

Wang et al., "Positional cloning of a novel potassium channel gene: KVLQT1 mutations cause cardiac arrhythmias," *Nat Genet* 12:17-23 (1996).

Watanbe et al., "Disruption of the epilepsy KCNQ2 gene results in neural hyperexcitability," *J. Neurochem* 75:28-33 (2000).

Wickenden et al., "KCNQ potassium channels: drug targets for the treatment of epilepsy and pain," *Exp. Opin Thera Patents* 14(4): 457-469 (2004).

Wickenden et al., "Retigabine, a novel anti-convulsant, enhances activation of KCNQ2/Q3 potassium channels," *Mol. Pharmacol*. 58:591-600 (2000).

Wuttke, "The new anticonvulsant retigabine favors voltage-dependent opening of the Kv7.2 (KCNQ2) channel by binding to its activation gate," *Mol. Pharmacol*. 67:1009-1017 (2005).

Beck et al., "Kreuzschmerzen in der Gynaekologischen praxis," Ginaekologe, Springer Verlag, Berlin Germany 35(5):490-494 (2002).

Kuo et al., "Inhibition of $Na^+$ current by diphenhydramine and other diphenyl compounds: molecular determinants of selective binding to the inactivated channels," *Mol. Pharmacol*. 57(1):135-143(2000).

Patani, "Bioisosterism: A Rational Approach in Drug Design," *Chem. Rev*. 96:3147-3176 (1996).

Touboul et al. "A Comparative evaluation of the effects of Propafenone and lidocaine on early ventricular arrhythmias after acute myocardial infarction," *Eur. Heart J*. 9:1188-1193 (1988). Abstract.

Vippagunta et al., "Crystalline solids," *Adv. Drug Deliv. Rev*. 48:3-26 (2001).

Wolf (ed.), Burger's Medicinal Chemistry and Drug Discovery, 5th Edition vol. 1: Principles and Practice, John Wiley & Sons, New York, pp. 975-977 (1995).

Wu et al., "Regulatory perspectives of Type II prodrug development and time-dependent toxicity management: nonclinical Pharm/Tox analysis and the role of comparative toxicology," *Toxicology* 236:1-6 (2007).

Zani et al., "Sodium channels are required during in vivo sodium chloride hyperosmolarity to stimulate increase in intestinal endothelial nitric oxide production," *Am. J. Physiol. Heart Circ. Physiol.* 288:H89-H95 (2005).

* cited by examiner

DERIVATIVES OF 4-(N-AZACYCLOALKYL) ANILIDES AS POTASSIUM CHANNEL MODULATORS

CROSS-REFERENCE TO RELATED APPLICATIONS

This application claims priority under 35 U.S.C. §119(e) to U.S. Provisional Application No. 60/934,396, filed Jun. 13, 2007, which is incorporated by reference herein in its entirety.

FIELD OF THE INVENTION

This invention concerns novel compounds that modulate potassium channels. The compounds are useful for the treatment and prevention of diseases and disorders which are affected by activities of potassium ion channels. One such condition is seizure disorders.

BACKGROUND OF THE INVENTION

Retigabine (N-[2-amino-4-(4-fluorobenzylamino)phenyl] carbamic acid, ethyl ester] (U.S. Pat. No. 5,384,330) has been found to be an effective treatment of seizure disorders in children. Bialer, M. et al., *Epilepsy Research* 1999, 34, 1-41. Retigabine has also been found to be useful in treating pain, including neuropathic pain. Blackburn-Munro and Jensen, *Eur. J. Pharmacol.* 2003, 460, 109-116.

A form of epilepsy known as "benign familial neonatal convulsions" has been associated with mutations in the KCNQ2/3 channels. Biervert, C. et al., *Science* 1998, 27, 403-06; Singh, N. A. et al., *Nat. Genet.* 1998, 18, 25-29; Charlier, C. et al., *Nat. Genet.* 1998, 18, 53-55, Rogawski, *Trends in Neurosciences* 2000, 23, 393-398. Subsequent investigations have established that the primary site of retigabine action is the KCNQ2/3 channel. Wickenden, A. D. et al., *Mol. Pharmacol.* 2000, 58, 591-600; Main, M. J. et al., *Mol. Pharmcol.* 2000, 58, 253-62. Retigabine has been shown to increase the conductance of the channels at the resting membrane potential and to bind the activation gate of the KCNQ 2/3 channel. Wuttke, T. V. et al., *Mol. Pharmacol.* 2005, 67, 1009-1017.

The recognition of retigabine as a potassium channel modulator has prompted a search for other potassium channel modulators among compounds related to retigabine. Several such searches have been reported in the patent literature, most notably the following: WO 2004/058739; WO 2004/80950; WO 2004/82677; WO 2004/96767; WO 2005/087754; and WO 2006/029623.

BRIEF DESCRIPTION OF THE INVENTION

In one embodiment, this invention provides a compound of formula I

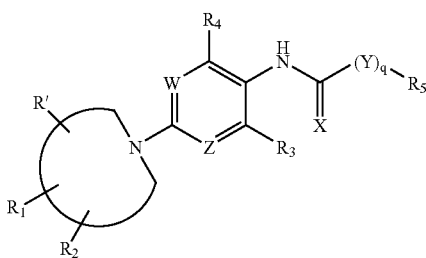

where at least one of W and Z is N;

where the moiety

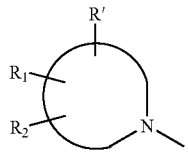

hereafter denoted "Amine-Ring" is one of Groups A or B below

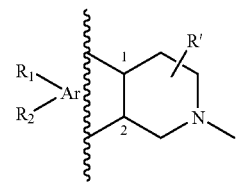

A where Ar is a 1,2-fused, six membered ring aromatic group, bearing substituents $R_1$ and $R_2$ as defined below, and containing zero or one ring nitrogen atom;

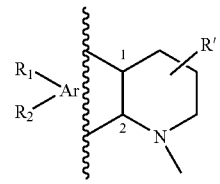

B where Ar is a 1,2-fused, six membered ring aromatic group, bearing substituents $R_1$ and $R_2$ as defined below, and containing zero or one ring nitrogen atom;

where $R_1$ and $R_2$, are, independently, H, CN, halogen, $CH_2CN$, OH, $NO_2$, $CH_2F$, $CHF_2$, $CF_3$, $CF_2CF_3$, $C_1$-$C_6$ alkyl, $C(=O)C_1$-$C_6$ alkyl, NH—$C_1$-$C_6$ alkyl, $NHC(=O)C_1$-$C_6$ alkyl, $C(=O)N(CH_3)_2$, $C(=O)N(Et)_2$, $C(=O)NH$—$C_1$-$C_6$ alkyl, $C(=O)OC_1$-$C_6$ alkyl, $OC(=O)C_1$-$C_6$ alkyl, $OC_1$-$C_6$ alkyl, $SC_1$-$C_6$ alkyl, $C_3$-$C_6$ cycloalkyl, $(CH_2)_mC_3$-$C_6$ cycloalkyl, $C_3$-$C_6$ cycloalkenyl, $(CH_2)_mC_3$-$C_6$ cycloalkenyl, $C_2$-$C_6$ alkenyl, $C_2$-$C_6$ alkynyl, $Ar_1$, $(CH_2)_mAr_1$, phenyl, pyridyl, pyrrolyl, $(CH_2)_m$imidazolyl, $(CH_2)_m$pyrazyl, furyl, thienyl, $(CH_2)_m$oxazolyl, $(CH_2)_m$isoxazolyl, $(CH_2)_m$thiazolyl, $(CH_2)_m$isothiazolyl, $(CH_2)_m$phenyl, $(CH_2)_m$pyrrolyl, $(CH_2)_m$pyridyl, or $(CH_2)_m$pyrimidyl, which cycloalkyl and said cycloalkenyl groups optionally contain one or two heteroatoms selected independently from O, N, and S, and which alkyl, cycloalkyl, cycloalkenyl, alkenyl, alkynyl, imidazolyl, pyrazyl, oxazolyl, isoxazolyl, thiazolyl, isothiazolyl, phenyl, pyrrolyl, pyridyl, or pyrimidyl groups are optionally substituted with one or two groups selected, independently, from OH, halogen, cyano, methyl, ethyl, or trifluoromethyl, where m is zero, 1, or 2; or $R_1$ and $R_2$, together with the ring carbon atoms to which they are attached, form a 5- or 6-member fused ring, which ring may be saturated, unsaturated, or aromatic, which optionally contains one or two heteroatoms selected independently from O, N, and S, and which is optionally substituted with halogen, $CF_3$, or $C_1$-$C_3$ alkyl; R' is H, halogen, $CF_3$, or $C_1$-$C_3$ alkyl; $R_3$ and $R_4$ are, independently, H, CN, halogen, $CF_3$, $OCF_3$, $OC_1$-$C_3$ alkyl, or $C_1$-$C_6$ alkyl, all said $C_1$-$C_3$ alkyl groups and said $C_1$-$C_6$ alkyl groups optionally substituted with one or two groups selected, independently, from OH, halogen, $C_1$-$C_3$ alkyl, $OC_1$-$C_3$ alkyl, or trifluoromethyl; X=O or S; Y is O or S; q=1 or 0; $R_5$ is $C_1$-$C_6$ alkyl, $(CHR_6)_wC_3$-$C_6$ cycloalkyl, $(CHR_6)_wCH_2C_3$-$C_6$ cycloalkyl, $CH_2(CHR_6)_wC_3$-$C_6$ cycloalkyl, $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, $C_2$-$C_6$ alkynyl, $Ar_1$, $(CHR_6)_wAr_1$, $CH_2(CHR_6)_wAr_1$, or $(CHR_6)_wCH_2Ar_1$, where w=0-3, $Ar_1$ is a 5- to 10-member mono- or bicyclic aromatic group, optionally containing 1-4 ring heteroatoms selected independently from N, O, and S; $R_6$ is hydrogen or $C_1$-$C_3$ alkyl; where all cycloalkyl and cycloalkenyl groups optionally contain one or two ring heteroatoms selected independently from N, O, and S; where all alkyl, cycloalkyl, alkenyl, cycloalkenyl, heterocycloalkyl, heterocycloalkenyl, alkynyl, aryl, and heteroaryl groups in $R_1$, $R_2$, $R_3$, $R_4$, $R_5$, $R_6$, or $Ar_1$ are optionally substituted with one or two substituents selected independently from $C_1$-$C_3$ alkyl, halogen, OH, OMe, SMe, CN, $CH_2F$, and trifluoromethyl; where, additionally, all cycloalkyl and heterocycloalkyl groups are optionally substituted with either an exocyclic carbon-carbon double bond or a carbonyl group; and where, additionally, the alkenyl and alkynyl groups are also optionally substituted with phenyl or $C_3$-$C_6$ cycloalkyl and all pharmaceutically acceptable salts thereof. Such compounds are potassium channel modulators.

In alternative embodiments, this invention provides a compound of formula I,

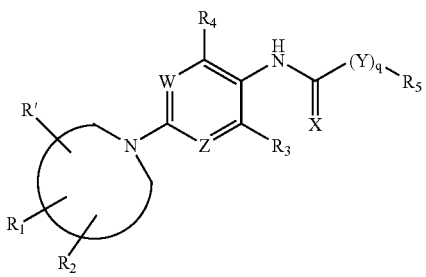

I where at least one of W and Z is N;
where the moiety

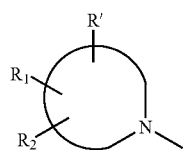

hereafter denoted "Amine-Ring" is one of Groups A or B below

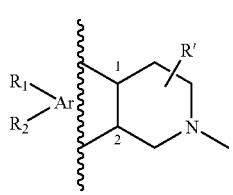

A where Ar is a 1,2-fused, six membered ring aromatic group, bearing substituents $R_1$ and $R_2$ as defined below, and containing zero, one, or two ring nitrogen atom;

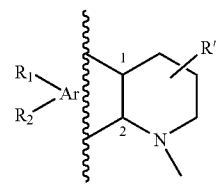

B where Ar is a 1,2-fused, six membered ring aromatic group, bearing substituents $R_1$ and $R_2$ as defined below, and containing zero, one, or two ring nitrogen atom;
where $R_1$ and $R_2$, are, independently, H, CN, halogen, $CH_2CN$, OH, $NO_2$, $CH_2F$, $CHF_2$, $CF_3$, $CF_2CF_3$, $C_1$-$C_6$ alkyl, C(=O)$C_1$-$C_6$ alkyl, NH—$C_1$-$C_6$ alkyl, NHC(=O)$C_1$-$C_6$ alkyl, C(=O)N($CH_3$)$_2$, C(=O)N(Et)$_2$, C(=O)NH—$C_1$-$C_6$ alkyl, C(=O)O$C_1$-$C_6$ alkyl, OC(=O)$C_1$-$C_6$ alkyl, $OC_1$-$C_6$ alkyl, $SC_1$-$C_6$ alkyl, $C_3$-$C_6$ cycloalkyl, $(CH_2)_mC_3$-$C_6$ cycloalkyl, $C_3$-$C_6$ cycloalkenyl, $(CH_2)_mC_3$-$C_6$ cycloalkenyl, $C_2$-$C_6$ alkenyl, $C_2$-$C_6$ alkynyl, $Ar_1$, $(CH_2)_mAr_1$, phenyl, pyridyl, pyrrolyl, $(CH_2)_m$imidazolyl, $(CH_2)_m$pyrazyl, furyl, thienyl, $(CH_2)_m$oxazolyl, $(CH_2)_m$isoxazolyl, $(CH_2)_m$thiazolyl, $(CH_2)_m$isothiazolyl, $(CH_2)_m$phenyl, $(CH_2)_m$pyrrolyl, $(CH_2)_m$pyridyl, or $(CH_2)_m$pyrimidyl, which cycloalkyl and said cycloalkenyl groups optionally contain one or two heteroatoms selected independently from O, N, and S, and which alkyl, cycloalkyl, cycloalkenyl, alkenyl, alkynyl, imidazolyl, pyrazyl, oxazolyl, isoxazolyl, thiazolyl, isothiazolyl, phenyl, pyrrolyl, pyridyl, or pyrimidyl groups are optionally substituted with one or two groups selected, independently, from OH, halogen, cyano, methyl, ethyl, or trifluoromethyl, where m is zero, 1, or 2; or $R_1$ and $R_2$, together with the ring carbon atoms to which they are attached, form a 5- or 6-member fused ring, which ring may be saturated, unsaturated, or aromatic, which optionally contains one or two heteroatoms selected independently from O, N, and S, and which is optionally substituted with halogen, $CF_3$, or $C_1$-$C_3$ alkyl; R' is H, halogen, $CF_3$, or $C_1$-$C_3$ alkyl; $R_3$ and $R_4$ are, independently, H, CN, halogen, $CF_3$, $OCF_3$, $OC_1$-$C_3$ alkyl, or $C_1$-$C_6$ alkyl, all said $C_1$-$C_3$ alkyl groups and said $C_1$-$C_6$ alkyl groups optionally substituted with one or two groups selected, independently, from OH, halogen, $C_1$-$C_3$ alkyl, $OC_1$-$C_3$ alkyl, or trifluoromethyl; X=O or S; Y is O or S; q=1 or 0; $R_5$ is $C_1$-$C_6$ alkyl, $(CHR_6)_wC_3$-$C_6$ cycloalkyl, $(CHR_6)_wCH_2C_3$-$C_6$ cycloalkyl, $CH_2(CHR_6)_wC_3$-$C_6$ cycloalkyl, $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, $C_2$-$C_6$ alkynyl, $Ar_1$, $(CHR_6)_wAr_1$, $CH_2(CHR_6)_wAr_1$, or $(CHR_6)_wCH_2Ar_1$, where w=0-3, $Ar_1$ is a 5- to 10-member mono- or bicyclic aromatic group, optionally containing 1-4 ring heteroatoms selected independently from N, O, and S; $R_6$ is hydrogen or $C_1$-$C_3$ alkyl; where all cycloalkyl and cycloalkenyl groups optionally contain one or two ring heteroatoms selected independently from N, O, and S; where all alkyl, cycloalkyl, alkenyl, cycloalkenyl, heterocycloalkyl, heterocycloalkenyl, alkynyl, aryl, and heteroaryl groups in $R_1$, $R_2$, $R_3$, $R_4$, $R_5$, $R_6$, or $Ar_1$ are optionally substituted with one or two substituents selected independently from $C_1$-$C_3$ alkyl, halogen, OH, OMe, SMe, CN, $CH_2F$, and trifluoromethyl; where, additionally, all cycloalkyl and heterocycloalkyl groups are optionally substituted with either an exocyclic carbon-carbon double bond or a carbonyl group; and where, additionally, the alkenyl and alkynyl groups are also optionally substituted with phenyl or $C_3$-$C_6$ cycloalkyl and all pharmaceutically acceptable salts thereof. Such compounds are potassium channel modulators.

In another embodiment, this invention provides a composition comprising a pharmaceutically acceptable carrier and at least one of the following: i) a pharmaceutically effective amount of a compound of formula I and ii) a pharmaceutically acceptable salt, ester, or prodrug thereof.

In yet another embodiment, this invention provides a method of preventing or treating a disease or disorder which is affected by modulation of potassium channels, comprising administering to a patient in need thereof a therapeutically effective amount of a compound of formula I or a salt, ester, or prodrug thereof.

This invention includes all tautomers and salts, as well as all stereoisomeric forms, of compounds of this invention. This invention also includes all compounds of this invention where one or more atoms are replaced by a radioactive isotope thereof.

This invention provides or contemplates compounds of formula I above where NH—C(=X)—(Y)$_q$—R$_5$ is each of the following: NHC(=O)R$_5$, NHC(=O)OR$_5$, NHC(=S)R$_5$, NHC(=S)SR$_5$, NHC(=S)OR$_5$, and NHC(=O)SR$_5$.

Thus, in one embodiment, this invention provides a compound of formula I, where NH—C(=X)—(Y)$_q$—R$_5$ is NHC(=O)R$_5$.

In another embodiment, this invention provides a compound of formula I, where NH—C(=X)—(Y)$_q$—R$_5$ is NHC(=S)R$_5$.

In another embodiment, this invention provides a compound of formula I, where NH—C(=X)—(Y)$_q$—R$_5$ is NHC(=S)SR$_5$.

In another embodiment, this invention provides a compound of formula I, where NH—C(=X)—(Y)$_q$—R$_5$ is each NHC(=O)OR$_5$.

In another embodiment, this invention provides a compound of formula I, where NH—C(=X)—(Y)$_q$—R$_5$ is NHC(=S)OR$_5$.

In another embodiment, this invention provides a compound of formula I, where NH—C(=X)—(Y)$_q$—R$_5$ is NHC(=O)SR$_5$.

In one subgeneric embodiment, this invention provides a compound of formula I, where Amine-Ring is Group A and NH—C(=X)—(Y)$_q$—R$_5$ is NHC(=O)R$_5$ or NHC(=S)R$_5$.

In another subgeneric embodiment, this invention provides a compound of formula I, where Amine-Ring is Group A and NH—C(=X)—(Y)$_q$—R$_5$ is NHC(=O)SR$_5$ or NHC(=S)OR$_5$.

In another subgeneric embodiment, this invention provides a compound of formula I, where Amine-Ring is Group A and NH—C(=X)—(Y)$_q$—R$_5$ is NHC(=O)OR$_5$ or NHC(=S)SR$_5$.

In another subgeneric embodiment, this invention provides a compound of formula I, where Amine-Ring is Group B and NH—C(=X)—(Y)$_q$—R$_5$ is NHC(=O)R$_5$ or NHC(=S)R$_5$.

In another subgeneric embodiment, this invention provides a compound of formula I, where Amine-Ring is Group B and NH—C(=X)—(Y)$_q$—R$_5$ is NHC(=O)SR$_5$ or NHC(=S)OR$_5$.

In another subgeneric embodiment, this invention provides a compound of formula I, where Amine-Ring is Group B and NH—C(=X)—(Y)$_q$—R$_5$ is NHC(=O)OR$_5$ or NHC(=S)SR$_5$.

In another subgeneric embodiment, this invention provides a compound of formula IA1 below.

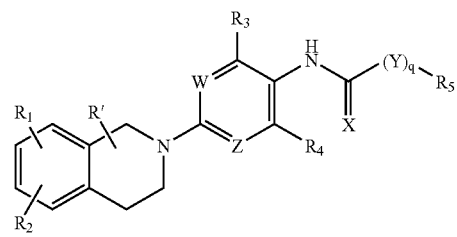

IA1

In another subgeneric embodiment, this invention provides a compound of formula IA2 below.

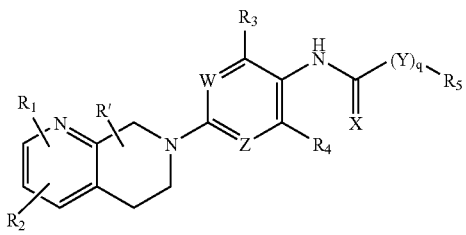

IA2

In another subgeneric embodiment, this invention provides a compound of formula IA3 below.

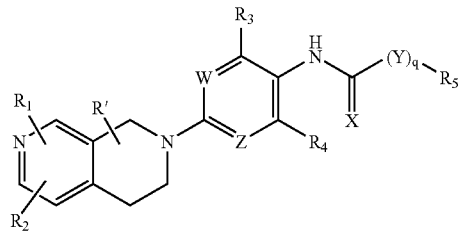

IA3

In another subgeneric embodiment, this invention provides a compound of formula IA4 below.

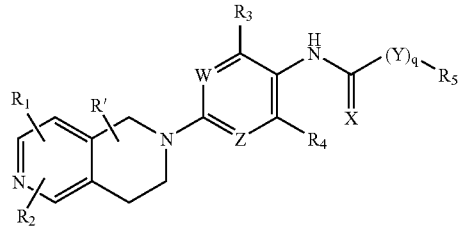

IA4

In another subgeneric embodiment, this invention provides a compound of formula IA5 below.

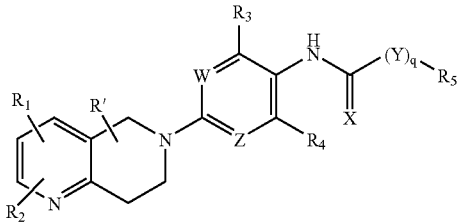

IA5

In another subgeneric embodiment, the invention provides a compound of formula IB1 below.

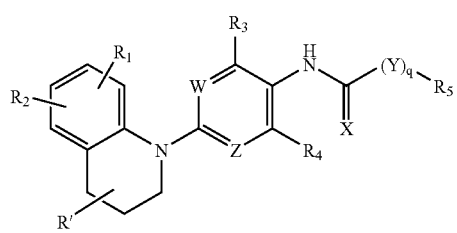

IB1

In another subgeneric embodiment, the invention provides a compound of formula IB2 below.

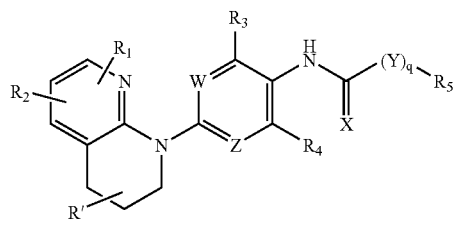

IB2

In another subgeneric embodiment, the invention provides a compound of formula IB3 below.

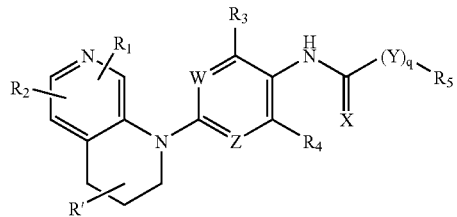

IB3

In another subgeneric embodiment, the invention provides a compound of formula IB4 below.

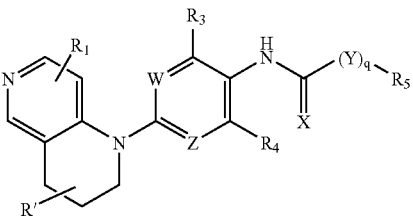

IB4

In another subgeneric embodiment, the invention provides a compound of formula IB5 below.

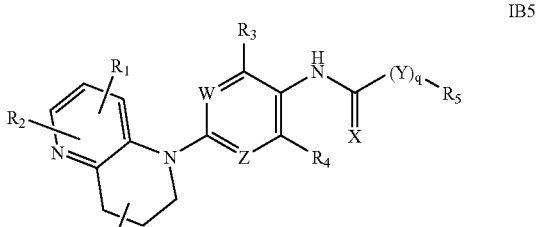

IB5

In a more specific subgeneric embodiment, the invention provides a compound of any of formulas IA1-IA5, where W and Z are both N.

In another more specific subgeneric embodiment, this invention provides a compound of any of formulas IA1-IA5, where W is N and Z is C.

In another more specific subgeneric embodiment, this invention provides a compound of any of formulas IA1-IA5, where W is C and Z is N.

In another more specific subgeneric embodiment, this invention provides a compound of any of formulas IA1-IA5, where R' is H, halogen, CF3, or methyl.

In another more specific subgeneric embodiment, this invention provides a compound of any of formulas IA1-IA5, where W and Z are both N and R' is H, F, or methyl.

In another more specific subgeneric embodiment, the invention provides a compound of any of formulas IB1-IB5, where W and Z are both N.

In another more specific subgeneric embodiment, this invention provides a compound of any of formulas IB1-IB5, where W is N and Z is C.

In another more specific subgeneric embodiment, this invention provides a compound of any of formulas IB1-IB5, where W is C and Z is N.

In another more specific subgeneric embodiment, this invention provides a compound of any of formulas IB1-IB5, where R' is H, halogen, CF3, or methyl.

In another more specific subgeneric embodiment, this invention provides a compound of any of formulas IB1-IB5, where W and Z are both N and R' is H, F, or methyl.

In a more specific subgeneric embodiment, this invention provides or contemplates a compound of any of formulas IA1-IA5, where X is O, q=1, Y is O, and $R_5$ is $C_1$-$C_6$ alkyl, $(CHR_6)_w C_3$-$C_6$ cycloalkyl, $(CHR_6)_w CH_2 C_3$-$C_6$ cycloalkyl, or $CH_2(CHR_6)_w C_3$-$C_6$ cycloalkyl.

In a still more specific subgeneric embodiment, this invention provides or contemplates a compound of any of formulas IA1-IA5, where X is O; q=1; Y is O; $R_5$ is $C_1$-$C_6$ alkyl, $(CHR_6)_w C_3$-$C_6$ cycloalkyl, $(CHR_6)_w CH_2 C_3$-$C_6$ cycloalkyl, or $CH_2(CHR_6)_w C_3$-$C_6$ cycloalkyl; and $R_1$ is H, CF3, or halogen.

In a still more specific subgeneric embodiment, this invention provides or contemplates a compound of any of formulas IA1-IA5, where X is O; q=1; Y is O; $R_5$ is $C_1$-$C_6$ alkyl, substituted with methoxy, methylthio, or halogen; and $R_1$ is H, $CF_3$, or halogen.

In another subgeneric embodiment, this invention provides or contemplates a compound of any of formulas IA1-IA5, where X is O, q=1, Y is O, and $R_5$ is $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, or $C_2$-$C_6$ alkynyl.

In another more specific subgeneric embodiment, this invention provides or contemplates a compound of any of formulas IA1-IA5, where X is O, q=1, Y is O, and $R_5$ is $Ar_1$, $(CHR_6)_wAr_1$, $CH_2(CHR_6)_wAr_1$, or $(CHR_6)_wCH_2Ar_1$.

In another more specific subgeneric embodiment, this invention provides or contemplates a compound of any of formulas IA1-IA5, where X is O, q=1, Y is S, and $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl.

In another more specific subgeneric embodiment, this invention provides or contemplates a compound of any of formulas IA1-IA5, where X is O, q=1, Y is S, and $R_5$ is $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, or $C_2$-$C_6$ alkynyl.

In another more specific subgeneric embodiment, this invention provides or contemplates a compound of any of formulas IA1-IA5, where X is O, q=1, Y is S, and $R_5$ is $Ar_1$, $(CHR_6)_wAr_1$, $CH_2(CHR_6)_wAr_1$, or $(CHR_6)_wCH_2Ar_1$.

In another more specific subgeneric embodiment, this invention provides or contemplates a compound of any of formulas IA1-IA5, where X is O, q=zero, and $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl.

In another more specific subgeneric embodiment, this invention provides or contemplates a compound of any of formulas IA1-IA5, where X is O; q=zero; $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl; and $R_1$ is halogen.

In another more specific subgeneric embodiment, this invention provides or contemplates a compound of any of formulas IA1-IA5, where X is O; q=zero; $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl; R' is halogen or $C_1$-$C_3$ alkyl; and $R_1$ is halogen.

In another more specific subgeneric embodiment, this invention provides or contemplates a compound of any of formulas IA1-IA5, where X is O, q=zero, and $R_5$ is $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, or $C_2$-$C_6$ alkynyl.

In another more specific subgeneric embodiment, this invention provides or contemplates a compound of any of formulas IA1-IA5, where X is O, q=zero, and $R_5$ is $Ar_1$, $(CHR_6)_wAr_1$, $CH_2(CHR_6)_wAr_1$, or $(CHR_6)_wCH_2Ar_1$.

In another more specific subgeneric embodiment, this invention provides or contemplates a compound of any of formulas IA1-IA5, where X is S, q=1, Y is O, and $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl.

In another more specific subgeneric embodiment, this invention provides or contemplates a compound of any of formulas IA1-IA5, where X is S, q=1, Y is O, and $R_5$ is $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, or $C_2$-$C_6$ alkynyl.

In another more specific subgeneric embodiment, this invention provides or contemplates a compound of any of formulas IA1-IA5, where X is S, q=1, Y is O, and $R_5$ is $Ar_1$, $(CHR_6)Ar_1$, $CH_2(CHR_6)_wAr_1$, or $(CHR_6)_wCH_2Ar_1$.

In another more specific subgeneric embodiment, this invention provides or contemplates a compound of any of formulas IA1-IA5, where X is S, q=zero, and $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl.

In another more specific subgeneric embodiment, this invention provides or contemplates a compound of any of formulas IA1-IA5, where X is S, q=zero, and $R_5$ is $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, or $C_2$-$C_6$ alkynyl.

In another more specific subgeneric embodiment, this invention provides or contemplates a compound of any of formulas IA1-IA5, where X is S, q=zero, and $R_5$ is $Ar_1$, $(CHR_6)Ar_1$, $CH_2(CHR_6)_wAr_1$, or $(CHR_6)_wCH_2Ar_1$.

In another more specific subgeneric embodiment, this invention provides or contemplates a compound of any of formulas IA1-IA5, where X is S, q=1, Y is S, and $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl.

In another more specific subgeneric embodiment, this invention provides or contemplates a compound of any of formulas IA1-IA5, where X is S, q=1, Y is S, and $R_5$ is $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, or $C_2$-$C_6$ alkynyl.

In another more specific subgeneric embodiment, this invention provides or contemplates a compound of any of formulas IA1-IA5, where X is S, q=1, Y is S, and $R_5$ is $Ar_1$, $(CHR_6)_wAr_1$, $CH_2(CHR_6)_wAr_1$, or $(CHR_6)_wCH_2Ar_1$.

In a more specific subgeneric embodiment, this invention provides or contemplates a compound of formula IA-1, where X is O, q=1, Y is O, and $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl.

In a still more specific subgeneric embodiment, this invention provides or contemplates a compound of any of formulas IA-1, where X is O; q=1; Y is O; and $R_5$ is $C_1$-$C_6$ alkyl, substituted with methoxy, methylthio, or halogen.

In another more specific subgeneric embodiment, this invention provides or contemplates a compound of formula IA-1, where X is O, q=1, Y is O, and $R_5$ is $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, or $C_2$-$C_6$ alkynyl.

In another more specific subgeneric embodiment, this invention provides or contemplates a compound of formula IA-1, where X is O, q=1, Y is O, and $R_5$ is $Ar_1$, $(CHR_6)_wAr_1$, $CH_2(CHR_6)_wAr_1$, or $(CHR_6)_wCH_2Ar_1$.

In another more specific subgeneric embodiment, this invention provides or contemplates a compound of formula IA-1, where X is O, q=1, Y is S, and $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl.

In another more specific subgeneric embodiment, this invention provides or contemplates a compound of formula IA-1, where X is O, q=1, Y is S, and $R_5$ is $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, or $C_2$-$C_6$ alkynyl.

In another more specific subgeneric embodiment, this invention provides or contemplates a compound of formula IA-1, where X is O, q=1, Y is S, and $R_5$ is $Ar_1$, $(CHR_6)_w Ar_1$, $CH_2(CHR_6)_w Ar_1$, or $(CHR_6)_w CH_2 Ar_1$.

In another more specific subgeneric embodiment, this invention provides or contemplates a compound of formula IA-1, where X is O, q=zero, and $R_5$ is $C_1$-$C_6$ alkyl, $(CHR_6)_w$ $C_3$-$C_6$ cycloalkyl, $(CHR_6)_w CH_2 C_3$-$C_6$ cycloalkyl, or $CH_2(CHR_6)_w C_3$-$C_6$ cycloalkyl.

In another more specific subgeneric embodiment, this invention provides or contemplates a compound of formula IA-1, where X is O, q=zero, and $R_5$ is $CR_6$=CH—$C_3$-$C_6$ cycloalkyl, CH=$CR_6$—$C_3$-$C_6$ cycloalkyl, $(CHR_6)_w C_5$-$C_6$ cycloalkenyl, $CH_2(CHR_6)_w C_5$-$C_6$ cycloalkenyl, $C_2$-$C_6$ alkenyl, or $C_2$-$C_6$ alkynyl.

In another more specific subgeneric embodiment, this invention provides or contemplates a compound of formula IA-1, where X is O, q=zero, and $R_5$ is $Ar_1$, $(CHR_6)_w Ar_1$, $CH_2(CHR_6)_w Ar_1$, or $(CHR_6)_w CH_2 Ar_1$.

In another more specific subgeneric embodiment, this invention provides or contemplates a compound of formula IA-1, where X is S, q=1, Y is O, and $R_5$ is $C_1$-$C_6$ alkyl, $(CHR_6)_w C_3$-$C_6$ cycloalkyl, $(CHR_6)_w CH_2 C_3$-$C_6$ cycloalkyl, or $CH_2(CHR_6)_w C_3$-$C_6$ cycloalkyl.

In another more specific subgeneric embodiment, this invention provides or contemplates a compound of formula IA-1, where X is S, q=1, Y is O, and $R_5$ is $CR_6$=CH—$C_3$-$C_6$ cycloalkyl, CH=$CR_6$—$C_3$-$C_6$ cycloalkyl, $(CHR_6)_w C_5$-$C_6$ cycloalkenyl, $CH_2(CHR_6)_w C_5$-$C_6$ cycloalkenyl, $C_2$-$C_6$ alkenyl, or $C_2$-$C_6$ alkynyl.

In another more specific subgeneric embodiment, this invention provides or contemplates a compound of formula IA-1, where X is S, q=1, Y is O, and $R_5$ is $Ar_1$, $(CHR_6)_w Ar_1$, $CH_2(CHR_6)_w Ar_1$, or $(CHR_6)_w CH_2 Ar_1$.

In another more specific subgeneric embodiment, this invention provides or contemplates a compound of formula IA-1, where X is S, q=zero, and $R_5$ is $C_1$-$C_6$ alkyl, $(CHR_6)_w$ $C_3$-$C_6$ cycloalkyl, $(CHR_6)_w CH_2 C_3$-$C_6$ cycloalkyl, or $CH_2(CHR_6)_w C_3$-$C_6$ cycloalkyl.

In another more specific subgeneric embodiment, this invention provides or contemplates a compound of formula IA-1, where X is S, q=zero, and $R_5$ is $CR_6$=CH—$C_3$-$C_6$ cycloalkyl, CH=$CR_6$—$C_3$-$C_6$ cycloalkyl, $(CHR_6)_w C_5$-$C_6$ cycloalkenyl, $CH_2(CHR_6)_w C_5$-$C_6$ cycloalkenyl, $C_2$-$C_6$ alkenyl, or $C_2$-$C_6$ alkynyl.

In another more specific subgeneric embodiment, this invention provides or contemplates a compound of formula IA-1, where X is S, q=zero, and $R_5$ is $Ar_1$, $(CHR_6)_w Ar_1$, $CH_2(CHR_6)_w Ar_1$, or $(CHR_6)_w CH_2 Ar_1$.

In another more specific subgeneric embodiment, this invention provides or contemplates a compound of formula IA-1, where X is S, q=1, Y is S, and $R_5$ is $C_1$-$C_6$ alkyl, $(CHR_6)_w C_3$-$C_6$ cycloalkyl, $(CHR_6)_w CH_2 C_3$-$C_6$ cycloalkyl, or $CH_2(CHR_6)_w C_3$-$C_6$ cycloalkyl.

In another more specific subgeneric embodiment, this invention provides or contemplates a compound of formula IA-1, where X is S, q=1, Y is S, and $R_5$ is $CR_6$=CH—$C_3$-$C_6$ cycloalkyl, CH=$CR_6$—$C_3$-$C_6$ cycloalkyl, $(CHR_6)_w C_5$-$C_6$ cycloalkenyl, $CH_2(CHR_6)_w C_5$-$C_6$ cycloalkenyl, $C_2$-$C_6$ alkenyl, or $C_2$-$C_6$ alkynyl.

In another more specific subgeneric embodiment, this invention provides or contemplates a compound of any of formulas IA1-IA5, where X is S, q=1, Y is S, and $R_5$ is $Ar_1$, $(CHR_6)_w Ar_1$, $CH_2(CHR_6)_w Ar_1$, or $(CHR_6)_w CH_2 Ar_1$.

In another more specific subgeneric embodiment, this invention provides or contemplates a compound of formula IB, where X is O, q=1, Y is O, and $R_5$ is $C_1$-$C_6$ alkyl, $(CHR_6)_w$ $C_3$-$C_6$ cycloalkyl, $(CHR_6)_w CH_2 C_3$-$C_6$ cycloalkyl, or $CH_2(CHR_6)_w C_3$-$C_6$ cycloalkyl.

In another more specific subgeneric embodiment, this invention provides or contemplates a compound of formula IB, where X is O, q=1, Y is O, and $R_5$ is $CR_6$=CH—$C_3$-$C_6$ cycloalkyl, CH=$CR_6$—$C_3$-$C_6$ cycloalkyl, $(CHR_6)_w C_5$-$C_6$ cycloalkenyl, $CH_2(CHR_6)_w C_5$-$C_6$ cycloalkenyl, $C_2$-$C_6$ alkenyl, or $C_2$-$C_6$ alkynyl.

In another more specific subgeneric embodiment, this invention provides or contemplates a compound of formula IB, where X is O, q=1, Y is O, and $R_5$ is $Ar_1$, $(CHR_6)_w Ar_1$, $CH_2(CHR_6)_w Ar_1$, or $(CHR_6)_w CH_2 Ar_1$.

In another more specific subgeneric embodiment, this invention provides or contemplates a compound of formula IB, where X is O, q=1, Y is S, and $R_5$ is $C_1$-$C_6$ alkyl, $(CHR_6)_w$ $C_3$-$C_6$ cycloalkyl, $(CHR_6)_w CH_2 C_3$-$C_6$ cycloalkyl, or $CH_2(CHR_6)_w C_3$-$C_6$ cycloalkyl.

In another more specific subgeneric embodiment, this invention provides or contemplates a compound of formula IB, where X is O, q=1, Y is S, and $R_5$ is $CR_6$=CH—$C_3$-$C_6$ cycloalkyl, CH=$CR_6$—$C_3$-$C_6$ cycloalkyl, $(CHR_6)_w C_5$-$C_6$ cycloalkenyl, $CH_2(CHR_6)_w C_5$-$C_6$ cycloalkenyl, $C_2$-$C_6$ alkenyl, or $C_2$-$C_6$ alkynyl.

In another more specific subgeneric embodiment, this invention provides or contemplates a compound of formula IB, where X is O, q=1, Y is S, and $R_5$ is $Ar_1$, $(CHR_6)_w Ar_1$, $CH_2(CHR_6)_w Ar_1$, or $(CHR_6)_w CH_2 Ar_1$.

In another more specific subgeneric embodiment, this invention provides or contemplates a compound of formula IB, where X is O, q=zero, and $R_5$ is $C_1$-$C_6$ alkyl, $(CHR_6)_w C_3$-$C_6$ cycloalkyl, $(CHR_6)_w CH_2 C_3$-$C_6$ cycloalkyl, or $CH_2(CHR_6)_w C_3$-$C_6$ cycloalkyl.

In another more specific subgeneric embodiment, this invention provides or contemplates a compound of formula IB, where X is O, q=zero, and $R_5$ is $CR_6$=CH—$C_3$-$C_6$ cycloalkyl, CH=$CR_6$—$C_3$-$C_6$ cycloalkyl, $(CHR_6)_w C_5$-$C_6$ cycloalkenyl, $CH_2(CHR_6)_w C_5$-$C_6$ cycloalkenyl, $C_2$-$C_6$ alkenyl, or $C_2$-$C_6$ alkynyl.

In another more specific subgeneric embodiment, this invention provides or contemplates a compound of formula IB, where X is O, q=zero, and $R_5$ is $Ar_1$, $(CHR_6)_w Ar_1$, $CH_2(CHR_6)_w Ar_1$, or $(CHR_6)_w CH_2 Ar_1$.

In another more specific subgeneric embodiment, this invention provides or contemplates a compound of formula IB, where X is S, q=1, Y is O, and $R_5$ is $C_1$-$C_6$ alkyl, $(CHR_6)_w$ $C_3$-$C_6$ cycloalkyl, $(CHR_6)_w CH_2 C_3$-$C_6$ cycloalkyl, or $CH_2(CHR_6)_w C_3$-$C_6$ cycloalkyl.

In another more specific subgeneric embodiment, this invention provides or contemplates a compound of formula IB, where X is S, q=1, Y is O, and $R_5$ is $CR_6$=CH—$C_3$-$C_6$ cycloalkyl, CH=$CR_6$—$C_3$-$C_6$ cycloalkyl, $(CHR_6)_w C_5$-$C_6$ cycloalkenyl, $CH_2(CHR_6)_w C_5$-$C_6$ cycloalkenyl, $C_2$-$C_6$ alkenyl, or $C_2$-$C_6$ alkynyl.

In another more specific subgeneric embodiment, this invention provides or contemplates a compound of formula IB, where X is S, q=1, Y is O, and $R_5$ is $Ar_1$, $(CHR_6)_w Ar_1$, $CH_2(CHR_6)_w Ar_1$, or $(CHR_6)_w CH_2 Ar_1$.

In another more specific subgeneric embodiment, this invention provides or contemplates a compound of formula IB, where X is S, q=zero, and $R_5$ is $C_1$-$C_6$ alkyl, $(CHR_6)_w C_3$-$C_6$ cycloalkyl, $(CHR_6)_w CH_2 C_3$-$C_6$ cycloalkyl, or $CH_2(CHR_6)_w C_3$-$C_6$ cycloalkyl.

In another more specific subgeneric embodiment, this invention provides or contemplates a compound of formula IB, where X is S, q=zero, and $R_5$ is $CR_6$=CH—$C_3$-$C_6$ cycloalkyl, CH=$CR_6$—$C_3$-$C_6$ cycloalkyl, $(CHR_6)_w C_5$-$C_6$ cycloalkenyl, $CH_2(CHR_6)_w C_5$-$C_6$ cycloalkenyl, $C_2$-$C_6$ alkenyl, or $C_2$-$C_6$ alkynyl.

In another more specific subgeneric embodiment, this invention provides or contemplates a compound of formula IB, where X is S, q=zero, and $R_5$ is $Ar_1$, $(CHR_6)_w Ar_1$, $CH_2(CHR_6)_w Ar_1$, or $(CHR_6)_w CH_2 Ar_1$.

In another more specific subgeneric embodiment, this invention provides or contemplates a compound of formula IB, where X is S, q=1, Y is S, and $R_5$ is $C_1$-$C_6$ alkyl, $(CHR_6)_w C_3$-$C_6$ cycloalkyl, $(CHR_6)_w CH_2 C_3$-$C_6$ cycloalkyl, or $CH_2(CHR_6)_w C_3$-$C_6$ cycloalkyl.

In another more specific subgeneric embodiment, this invention provides or contemplates a compound of formula IB, where X is S, q=1, Y is S, and $R_5$ is $CR_6=CH-C_3$-$C_6$ cycloalkyl, $CH=CR_6-C_3$-$C_6$ cycloalkyl, $(CHR_6)_w C_5$-$C_6$ cycloalkenyl, $CH_2(CHR_6)_w C_5$-$C_6$ cycloalkenyl, $C_2$-$C_6$ alkenyl, or $C_2$-$C_6$ alkynyl.

In another more specific subgeneric embodiment, this invention provides or contemplates a compound of formula IB, where X is S, q=1, Y is S, and $R_5$ is $Ar_1$, $(CHR_6)_w Ar_1$, $CH_2(CHR_6)_w Ar_1$, or $(CHR_6)_w CH_2 Ar_1$.

In another more specific subgeneric embodiment, this invention provides or contemplates a compound of formula IA1, IA2, IA3, IA4, IA5, IB1, IB2, IB3, IB4 or IB5, where X is O, q=1, Y is O, and $R_5$ is $C_1$-$C_6$ alkyl or $(CHR_6)_w C_3$-$C_6$ cycloalkyl.

In another more specific subgeneric embodiment, this invention provides or contemplates a compound of formula IA1, IA2, IA3, IA4, IA5, IB1, IB2, IB3, IB4 or IB5, where X is S, q=1, Y is S, and $R_5$ is $C_1$-$C_6$ alkyl or $(CHR_6)_w C_3$-$C_6$ cycloalkyl.

In another more specific subgeneric embodiment, this invention provides or contemplates a compound of formula IA1, IA2, IA3, IA4, IA5, IB1, IB2, IB3, IB4 or IB5, where X is S, q=1, Y is O, and $R_5$ is $C_1$-$C_6$ alkyl or $(CHR_6)_w C_3$-$C_6$ cycloalkyl.

In another more specific subgeneric embodiment, this invention provides or contemplates a compound of formula IA1, IA2, IA3, IA4, IA5, IB1, IB2, IB3, IB4 or IB5, where X is O, q=1, Y is S, and $R_5$ is $C_1$-$C_6$ alkyl or $(CHR_6)_w C_3$-$C_6$ cycloalkyl.

In another more specific subgeneric embodiment, this invention provides or contemplates a compound of formula IA1, IA2, IA3, IA4, IA5, IB1, IB2, IB3, IB4 or IB5, where X is O, q zero, and $R_5$ is $C_1$-$C_6$ alkyl or $(CHR_6)_w C_3$-$C_6$ cycloalkyl.

In a still more specific subgeneric embodiment, this invention provides or contemplates a compound of formula IA1, IA2, IA3, IA4, IA5, IB1, IB2, IB3, IB4 or IB5, where X is O, q=zero, and $R_5$ is $C_5$-$C_6$ alkyl, $CH_2$—$C_5$-$C_6$ cycloalkyl, $CH_2CH_2$—N-pyrrolidinyl, or $CH_2CH_2$—$C_5$-$C_6$ cycloalkyl.

In another still more specific subgeneric embodiment, this invention provides or contemplates a compound of formula IA1, IA2, IA3, IA4, IA5, IB1, IB2, IB3, IB4 or IB5, where X is O, q=1, Y is O, and $R_5$ is $C_5$-$C_6$ alkyl, $CH_2$—$C_5$-$C_6$ cycloalkyl, or $CH_2CH_2$—N-pyrrolidinyl, or $CH_2CH_2$—$C_5$-$C_6$ cycloalkyl.

In another more specific subgeneric embodiment, this invention provides or contemplates a compound of formula IA1, IA2, IA3, IA4, IA5, IB1, IB2, IB3, IB4 or IB5, where $R_1$ is halogen; $R_2$ is H, halogen, or $C_1$-$C_4$ alkyl; X is O; and $R_5$ is $C_1$-$C_6$ alkyl, $(CHR_6)_w C_3$-$C_6$ cycloalkyl, $(CHR_6)_w CH_2 C_3$-$C_6$ cycloalkyl, or $CH_2(CHR_6)_w C_3$-$C_6$ cycloalkyl.

In another more specific subgeneric embodiment, this invention provides or contemplates a compound of formula IA1, IA2, IA3, IA4, IA5, IB1, IB2, IB3, IB4 or IB5, where $R_1$ is halogen or halomethyl; $R_2$ is H, halogen, or $C_1$-$C_4$ alkyl; X is O; and $R_5$ is $C_1$-$C_6$ alkyl, $(CHR_6)_w C_3$-$C_6$ cycloalkyl, $(CHR_6)_w CH_2 C_3$-$C_6$ cycloalkyl, or $CH_2(CHR_6)_w C_3$-$C_6$ cycloalkyl.

In another more specific subgeneric embodiment, this invention provides or contemplates a compound of formula IA1, IA2, IA3, IA4, IA5, IB1, IB2, IB3, IB4 or IB5, where $R_1$ is halogen or halomethyl; $R_2$ is H, halogen, or $C_1$-$C_4$ alkyl; R' is halogen, methyl, or halomethyl; X is O; and $R_5$ is $C_1$-$C_6$ alkyl, $(CHR_6)_w C_3$-$C_6$ cycloalkyl, $(CHR_6)_w CH_2 C_3$-$C_6$ cycloalkyl, or $CH_2(CHR_6)_w C_3$-$C_6$ cycloalkyl.

In another more specific subgeneric embodiment, this invention provides or contemplates a compound of formula IA1, IA2, IA3, IA4, IA5, IB1, IB2, IB3, IB4 or IB5, where X is O, q zero, and $R_5$ is $C_3$-$C_6$ alkyl, $CH_2CH_2$-cyclopentyl or one of the groups below:

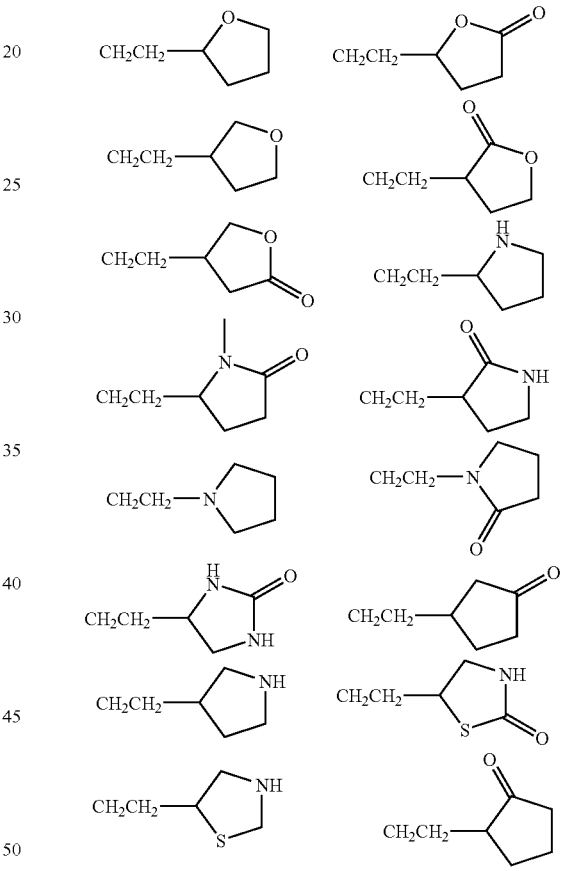

In another more specific subgeneric embodiment, this invention provides or contemplates a compound of formula IA1, IA2, IA3, IA4, IA5, IB1, IB2, IB3, IB4 or IB5, where $R_1$ is halogen or halomethyl; $R_2$ is H, halogen, or $C_1$-$C_4$ alkyl; X is O; and $R_5$ is one of the groups above.

In another more specific subgeneric embodiment, this invention provides or contemplates a compound of formula IA1, IA2, IA3, IA4, IA5, IB1, IB2, IB3, IB4 or IB5, where X is S, q zero, and $R_5$ is $C_1$-$C_6$ alkyl or $(CHR_6)_w C_3$-$C_6$ cycloalkyl.

In another subgeneric embodiment, this invention provides or contemplates a compound of formula IA1, IA2, IA3, IA4, IA5, IB1, IB2, IB3, IB4 or IB5, where $R_1$ is H, CN, halogen, $CH_2CN$, OH, $NO_2$, $CH_2F$, $CHF_2$, $CF_3$, $CF_2CF_3$, $C_1$-$C_6$ alkyl, or $C(=O)C_1$-$C_6$ alkyl.

In another subgeneric embodiment, this invention provides or contemplates a compound of formula IA1, IA2, IA3, IA4, IA5, IB1, IB2, IB3, IB4 or IB5, where $R_1$ is C(=O)$C_1$-$C_6$ alkyl, NHC(=O)$C_1$-$C_6$ alkyl, C(=O)N(CH$_3$)$_2$, C(=O)N(Et)$_2$, C(=O)NH—$C_1$-$C_6$ alkyl, C(=O)O$C_1$-$C_6$ alkyl, or OC(=O)$C_1$-$C_6$ alkyl.

In another subgeneric embodiment, this invention provides or contemplates a compound of formula IA1, IA2, IA3, IA4, IA5, IB1, IB2, IB3, IB4 or IB5, where $R_1$ is O$C_1$-$C_6$ alkyl, S$C_1$-$C_6$ alkyl, $C_3$-$C_6$ cycloalkyl, (CH$_2$)$_m$$C_3$-$C_6$ cycloalkyl, $C_3$-$C_6$ cycloalkenyl, (CH$_2$)$_m$$C_3$-$C_6$ cycloalkenyl, $C_2$-$C_6$ alkenyl, or $C_2$-$C_6$ alkynyl.

In another subgeneric embodiment, this invention provides or contemplates a compound of formula IA1, IA2, IA3, IA4, IA5, IB1, IB2, IB3, IB4 or IB5, where $R_1$ is phenyl, pyridyl, pyrrolyl, (CH$_2$)$_m$pyrazyl, (CH$_2$)$_m$imidazolyl, (CH$_2$)$_m$oxazolyl, (CH$_2$)$_m$isoxazolyl, (CH$_2$)$_m$thiazolyl, (CH$_2$)$_m$pyridyl, (CH$_2$)$_m$isothiazolyl, (CH$_2$)$_m$phenyl, (CH$_2$)$_m$pyrrolyl, or (CH$_2$)$_m$pyrimidyl.

In another more specific subgeneric embodiment, this invention provides or contemplates a compound of formula IA1, IA2, IA3, IA4, IA5, IB1, IB2, IB3, IB4 or IB5, where $R_1$ is C(=O)$C_1$-$C_6$ alkyl, NHC(=O)$C_1$-$C_6$ alkyl, C(=O)N(CH$_3$)$_2$, C(=O)N(Et)$_2$, C(=O)NH—$C_1$-$C_6$ alkyl, C(=O)O$C_1$-$C_6$ alkyl, or OC(=O)$C_1$-$C_6$ alkyl, and $R_5$ is $C_5$-$C_6$ alkyl or CH$_2$—$C_3$-$C_6$ cycloalkyl.

In another more specific subgeneric embodiment, this invention provides or contemplates a compound of formula IA1, IA2, IA3, IA4, IA5, IB1, IB2, IB3, IB4 or IB5, where $R_1$ is O$C_1$-$C_6$ alkyl, S$C_1$-$C_6$ alkyl, $C_3$-$C_6$ cycloalkyl, (CH$_2$)$_m$$C_3$-$C_6$ cycloalkyl, $C_3$-$C_6$ cycloalkenyl, (CH$_2$)$_m$$C_3$-$C_6$ cycloalkenyl, $C_2$-$C_6$ alkenyl, or $C_2$-$C_6$ alkynyl, and $R_5$ is $C_5$-$C_6$ alkyl or CH$_2$—$C_3$-$C_6$ cycloalkyl.

In another more specific subgeneric embodiment, this invention provides or contemplates a compound of formula IA1, IA2, IA3, IA4, IA5, IB1, IB2, IB3, IB4 or IB5, where $R_1$ is phenyl, pyridyl, pyrrolyl, (CH$_2$)$_m$imidazolyl, (CH$_2$)$_m$pyrazyl, (CH$_2$)$_m$oxazolyl, (CH$_2$)$_m$isoxazolyl, (CH$_2$)$_m$thiazolyl, (CH$_2$)$_m$isothiazolyl, (CH$_2$)$_m$phenyl, (CH$_2$)$_m$pyrrolyl, (CH$_2$)$_m$pyridyl, or (CH$_2$)$_m$pyrimidyl, and $R_5$ is $C_5$-$C_6$ alkyl or CH$_2$—$C_3$-$C_6$ cycloalkyl.

In a more specific subgeneric embodiment, this invention provides or contemplates a compound of any of formulas IA1-IA5, where X is O, q=1, Y is O, and $R_5$ is Ar$_1$ or CH$_2$—Ar$_1$, where Ar$_1$ is unsubstituted phenyl, mono substituted phenyl, unsubstituted pyridyl, or unsubstituted pyrrolyl.

In another more specific subgeneric embodiment, this invention provides or contemplates a compound of any of formulas IA1-IA5, where X is O, q=zero, and $R_5$ is Ar$_1$ or CH$_2$—Ar$_1$, where Ar$_1$ is unsubstituted phenyl, mono substituted phenyl, unsubstituted pyridyl, or unsubstituted pyrrolyl.

In another subgeneric embodiment, this invention provides or contemplates a compound of formula IA or IB, where $R_1$ and $R_2$ form a fused phenyl group, X is O, q=1, Y is O, and $R_5$ is $C_1$-$C_6$ alkyl or (CHR$_6$)$_w$$C_3$-$C_6$ cycloalkyl.

In another subgeneric embodiment, this invention provides or contemplates a compound of formula IA or IB, where $R_1$ and $R_2$ form a fused pyridyl group, X is O, q=1, Y is O, and $R_5$ is $C_1$-$C_6$ alkyl or (CHR$_6$)$_w$$C_3$-$C_6$ cycloalkyl.

In another subgeneric embodiment, this invention provides or contemplates a compound of formula IA1, IA2, IA3, IA4, IA5, IB1, IB2, IB3, IB4 or IB5, where $R_1$ is halogen, $C_1$-$C_6$ alkyl, mono-halo $C_1$-$C_6$ alkyl, CN, di-halo $C_1$-$C_6$ alkyl, CF$_3$, CN, or O—$C_1$-$C_6$ alkyl, and $R_5$ is $C_5$-$C_6$ alkyl or CH$_2$—$C_3$-$C_6$ cycloalkyl.

In another more specific subgeneric embodiment, this invention provides or contemplates a compound of formula IA1, IA2, IA3, IA4, IA5, IB1, IB2, IB3, IB4 or IB5, where $R_1$ is halogen, cyano, CF$_3$, or methoxy, $R_2$ is H or methyl, R' is H, halogen, or methyl, and $R_5$ is $C_5$-$C_6$ alkyl or CH$_2$—$C_3$-$C_6$ cycloalkyl.

In another more specific subgeneric embodiment, this invention provides or contemplates a compound of formula IA1, IA2, IA3, IA4, IA5, IB1, IB2, IB3, IB4 or IB5, where R' is halogen, CF$_3$, or $C_1$-$C_3$ alkyl.

In another more specific subgeneric embodiment, this invention provides or contemplates a compound of formula IA1, IA2, IA3, IA4, IA5, IB1, IB2, IB3, IB4 or IB5, where $R_1$ is halogen; $R_2$ is H or methyl, R' is H, halogen, or methyl; and $R_5$ is $C_5$-$C_6$ alkyl or CH$_2$—$C_5$-$C_6$ cycloalkyl.

In another more specific subgeneric embodiment, this invention provides or contemplates a compound of formula IA1, IA2, IA3, IA4, IA5, IB1, IB2, IB3, IB4 or IB5, where $R_1$ is halogen; $R_2$ is H or methyl, R' is H, halogen, or methyl; and $R_5$ is CH$_2$—$C_4$-alkyl or CH$_2$—$C_5$— alkyl.

In another subgeneric embodiment, this invention provides a compound of formula I, where $R_1$ or $R_5$ is CH$_2$Ar$_1$ or CH$_2$CH$_2$—Ar$_1$, where Ar$_1$ is phenyl, pyridyl, pyrrolyl, imidazolyl, oxazolyl, or thiazolyl.

In another subgeneric embodiment, this invention provides a compound of formula I, where $R_1$ and $R_2$ form pyrrolo, imidazolo, oxazolo, or thiazolo.

In another subgeneric embodiment, this invention provides a compound of formula I, where $R_1$ or $R_5$ is CH$_2$Ar$_1$ or CH$_2$CH$_2$—Ar$_1$, where Ar$_1$ is isoxazolyl or isothiazolyl.

In another subgeneric embodiment, this invention provides a compound of formula I, where $R_1$ or $R_5$ is CH$_2$Ar$_1$ or CH$_2$CH$_2$—Ar$_1$, where Ar$_1$ is quinolyl or isoquinolyl.

In another subgeneric embodiment, this invention provides a compound of formula I, where $R_1$ or $R_5$ is CH$_2$Ar$_1$ or CH$_2$CH$_2$—Ar$_1$, where Ar$_1$ is pyrimidyl or purinyl.

In another subgeneric embodiment, this invention provides a compound of formula I, where $R_1$ or $R_5$ is CH$_2$Ar$_1$ or CH$_2$CH$_2$—Ar$_1$, where Ar$_1$ is indolyl, isoindolyl, or benzimidazolyl.

In a more specific embodiment, this invention provides a compound of formula I, where $R_1$ or $R_5$ is CH$_2$Ar$_1$ or CH$_2$CH$_2$—Ar$_1$, where Ar$_1$ is halo phenyl.

In another more specific embodiment, this invention provides a compound of formula I, where $R_1$ or $R_5$ is CH$_2$Ar$_1$ or CH$_2$CH$_2$—Ar$_1$, where Ar$_1$ is dihalophenyl or dihalopyridyl.

In another more specific embodiment, invention provides or contemplates a compound of formula I, where Ar$_1$ is mono- or di-halothienyl, mono- or di-halofuryl, mono- or di-halobenzothienyl, or mono- or di-halobenzofuryl.

In another more specific embodiment, this invention provides or contemplates a compound of formula I, where $R_1$ or $R_5$ is CH$_2$Ar$_1$ or CH$_2$CH$_2$—Ar$_1$, where Ar$_1$ is o-, m-, or p-xylyl or o-, m-, or p-anisyl.

In another more specific embodiment, this invention provides or contemplates a compound of formula I, where $R_1$ or $R_5$ is CH$_2$Ar$_1$ or CH$_2$CH$_2$—Ar$_1$, where Ar$_1$ is m- or p-cyanophenyl or m- or p-cyanomethyl phenyl.

In another more specific embodiment, this invention provides a compound of formula I, where $R_1$ or $R_5$ is CH$_2$Ar$_1$ or CH$_2$CH$_2$—Ar$_1$, where Ar$_1$ is $C_2$-$C_5$ alkylphenyl.

In another more specific embodiment, this invention provides a compound of formula I, where $R_1$ or $R_5$ is CH$_2$Ar$_1$ or CH$_2$CH$_2$—Ar$_1$, where Ar$_1$ is 3,5-dichlorophenyl or 3,5-difluorophenyl.

In a more specific embodiment, this invention provides a compound of formula I, where $R_1$ or $R_5$ is Ar$_1$, (CHR$_6$)$_w$Ar$_1$, CH$_2$(CHR$_6$)$_w$Ar$_1$, or (CHR$_6$)$_w$CH$_2$Ar$_1$, where Ar$_1$ is phenyl or pyridyl, $R_3$ and $R_4$ are H or $C_1$-$C_6$ alkyl, unsubstituted or substituted with one or two groups selected from OH, OMe; $R_1$ is CN, $CH_2CN$, or halogen; q is 1; and X and Y are both O.

In another subgeneric embodiment, this invention provides a compound of formula I, where $R_5$ is $Ar_1$, $(CHR_6)_wAr_1$, $CH_2(CHR_6)_wAr_1$, or $(CHR_6)_wCH_2Ar_1$, where $Ar_1$ is phenyl or pyridyl, $R_1$ is F, $CH_2F$, $CHF_2$, $CF_3$, or $CF_2CF_3$, q is 1, and X and Y are both O.

In a more specific embodiment, this invention provides a compound of formula I, where $R_1$ or $R_5$ is $Ar_1$, $(CHR_6)_wAr_1$, $CH_2(CHR_6)_wAr_1$, or $(CHR_6)_wCH_2Ar_1$, where $Ar_1$ is phenyl or pyridyl, $R_1$ is $OC_1$-$C_6$ alkyl or $C(=O)C_1$-$C_6$ alkyl, q is 1, and X and Y are both O.

In a more specific embodiment, this invention provides a compound of formula I, where $R_1$ or $R_5$ is $Ar_1$, $(CHR_6)_wAr_1$, $CH_2(CHR_6)_wAr_1$, or $(CHR_6)_wCH_2Ar_1$, where $Ar_1$ is phenyl or pyridyl, $R_1$ is $C(=O)OC_1$-$C_6$ alkyl or $OC(=O)C_1$-$C_6$ alkyl, q is 1, and X and Y are both O.

In a more specific embodiment, this invention provides a compound of formula I, where $R_5$ is $Ar_1$, $(CHR_6)_wAr_1$, $CH_2(CHR_6)_wAr_1$, or $(CHR_6)_wCH_2Ar_1$, where $Ar_1$ is phenyl or pyridyl, $R_1$ is $C_2$-$C_6$ alkenyl or $C_2$-$C_6$ alkynyl, q is 1, and X and Y are both O.

In a more specific embodiment, this invention provides a compound of formula I, where where $R_5$ is $Ar_1$, $(CHR_6)_wAr_1$, $CH_2(CHR_6)_wAr_1$, or $(CHR_6)_wCH_2Ar_1$, $Ar_1$ is phenyl or pyridyl, $R_1$ is $SC_1$-$C_6$ alkyl, q is 1, and X and Y are both O.

In a more specific embodiment, this invention provides a compound of formula I, where $R_5$ is $Ar_1$, $(CHR_6)_wAr_1$, $CH_2(CHR_6)_wAr_1$, or $(CHR_6)_wCH_2Ar_1$, where $Ar_1$ is phenyl or pyridyl, $R_3$ and $R_4$ are H or $C_1$-$C_3$ alkyl, $R_1$ is $C_1$-$C_6$ alkyl, q is zero, and X is O.

In a more specific embodiment, this invention provides a compound of formula I, where $R_5$ is $Ar_1$, $(CHR_6)_wAr_1$, $CH_2(CHR_6)_wAr_1$, or $(CHR_6)_wCH_2Ar_1$, where $Ar_1$ is phenyl or pyridyl; $R_3$ and $R_4$ are H or $C_1$-$C_3$ alkyl; $R_1$ is $C_1$-$C_6$ alkyl; q is 1; and X is O.

In a more specific embodiment, this invention provides a compound of formula I, where $R_5$ is $Ar_1$, $(CHR_6)_wAr_1$, $CH_2(CHR_6)_wAr_1$, or $(CHR_6)_wCH_2Ar_1$, where $Ar_1$ is phenyl or pyridyl, $R_3$ and $R_4$ are H or $C_1$-$C_3$ alkyl, $R_1$ is CN, $CH_2CN$, or halogen, q is 1, Y is O, and X is O.

In another embodiment, this invention provides a compound of formula I, where $R_5$ is $Ar_1$, $(CHR_6)_wAr_1$, $CH_2(CHR_6)_wAr_1$, or $(CHR_6)_wCH_2Ar_1$, where $Ar_1$ is thienyl, furyl, benzothienyl, or benzofuryl; $R_3$ and $R_4$ are, independently, H, methyl, or ethyl; and $R_5$ is $C_1$-$C_6$ alkyl or $(CHR_6)_wC_3$-$C_6$ cycloalkyl.

In another embodiment, this invention provides a compound of formula I, where $R_5$ is $Ar_1$, $(CHR_6)_wAr_1$, $CH_2(CHR_6)_wAr_1$, or $(CHR_6)_wCH_2Ar_1$, where $Ar_1$ is pyrrolyl, imidazolyl, oxazolyl, or thiazolyl; $R_3$ and $R_4$ are, independently, H, methyl, or ethyl; and $R_5$ is $C_1$-$C_6$ alkyl or $(CHR_6)_wC_3$-$C_6$ cycloalkyl.

In another embodiment, this invention provides a compound of formula I, where $R_5$ is $Ar_1$, $(CHR_6)_wAr_1$, $CH_2(CHR_6)_wAr_1$, or $(CHR_6)_wCH_2Ar_1$, where $Ar_1$ is isoxazolyl or isothiazolyl; $R_3$ and $R_4$ are, independently, H, methyl, or ethyl; and $R_5$ is $C_1$-$C_6$ alkyl or $(CHR_6)_wC_3$-$C_6$ cycloalkyl.

In another embodiment, this invention provides a compound of formula I, in which $R_5$ is $C_1$-$C_6$ alkyl, where the alkyl group is substituted with one or two groups selected, independently, from OH, OMe, OEt, F, $CF_3$, Cl, or CN.

In another embodiment, this invention provides a compound of formula I, in which $R_5$ is $(CHR_6)_wC_3$-$C_6$ cycloalkyl, where w is 1 or 2 and $R_6$ is H or methyl, and where the cycloalkyl group is substituted with Me, OH, OMe, OEt, F, $CF_3$, Cl, or CN.

In a more specific embodiment, this invention provides a compound of formula I, in which $R_5$ is $(CH_2)_w$—$C_5$-$C_6$ cycloalkyl or $(CH_2)_w$—$C_5$-$C_6$ heterocycloalkyl.

In another embodiment, this invention provides a compound of formula I, in which $R_5$ is CH=CH—$C_3$-$C_6$ cycloalkyl or heterocycloalkyl, where the carbon-carbon double bond has the E configuration.

In another embodiment, this invention provides a compound of formula I, in which $R_5$ is CH=CH—$C_3$-$C_6$ cycloalkyl or heterocycloalkyl, where the carbon-carbon double bond has the Z configuration.

In another embodiment, this invention provides a compound of formula I, in which $R_5$ is $CH_2$—CH=CH—$C_3$-$C_6$ cycloalkyl or heterocycloalkyl, where the carbon-carbon double bond has the E configuration.

In another embodiment, this invention provides a compound of formula I, in which $R_5$ is $CH_2$CH=CH—$C_3$-$C_6$ cycloalkyl or heterocycloalkyl, where the carbon-carbon double bond has the Z configuration.

In another embodiment, this invention provides a compound of formula I, in which $R_5$ is CH=CH—$CH_2$—$C_3$-$C_6$ cycloalkyl or heterocycloalkyl, where the carbon-carbon double bond has the E configuration. In another embodiment, this invention provides a compound of formula I, in which $R_5$ is CH=CH—$CH_2$—$C_3$-$C_6$ cycloalkyl or heterocycloalkyl, where the carbon-carbon double bond has the Z configuration.

In another, more specific embodiment, this invention provides a compound of formula I, in which $R_5$ is $(CHR_6)_wC_3$-$C_6$ cycloalkyl or heterocycloalkyl, where the cycloalkyl or heterocycloalkyl group is monosubstituted.

In another embodiment, this invention provides a compound of formula I, in which $R_5$ is CH=CH—$CH_2$—$C_3$-$C_6$ cycloalkyl or heterocycloalkyl or CH=CH—$C_3$-$C_6$ cycloalkyl or heterocycloalkyl, where the cycloalkyl or heterocycloalkyl group is monosubstituted.

In another embodiment, this invention provides a compound of formula I, in which $R_5$ is $C_5$-$C_6$ alkyl.

In another embodiment, this invention provides a compound of formula I, in which q is zero and $R_5$ is $CH_2$—$C_4$-alkyl or $CH_2$—$C_5$— alkyl.

In another embodiment, this invention provides a compound of formula I, in which $R_5$ is $C_2$-$C_6$ alkynyl.

In another embodiment, this invention provides a compound of formula I, in which $R_5$ is $C_2$-$C_6$ alkenyl.

In a more specific embodiment, this invention provides a compound of formula IA1, IA2, IA3, IA4, or IA5, where X is O, $R_2$, R', and $R_3$ are H, and q=zero.

In another embodiment, this invention provides a compound of formula IB1, IB2, IB3, IB4 or IB5, where X is O, $R_2$, R', and $R_3$ are H, and q=zero.

In a more specific embodiment, this invention provides a compound of formula IA1, IA2, IA3, IA4, or IA5, where X is O, $R_2$, and R' are H, $R_3$ and $R_4$ are methyl or methoxy, and q=zero.

In another embodiment, this invention provides a compound of formula IB1, IB2, IB3, IB4 or IB5, where X is O, $R_2$, and R' are H, $R_3$ and $R_4$ are methyl or methoxy, and q=zero.

In a more specific subgeneric embodiment, this invention provides or contemplates a compound of any of formulas IB1-IB5, where X is O; q=1; Y is O; and $R_5$ is $C_1$-$C_6$ alkyl, $CH_2$—$C_3$-$C_6$ cycloalkyl, CH=CH—$C_3$-$C_6$ cycloalkyl or CH=CH—$CH_2$—$C_3$-$C_6$ cycloalkyl.

In a still more specific subgeneric embodiment, this invention provides or contemplates a compound of any of formulas IB1-IB5, where X is O; q=1; Y is O; and $R_5$ is $C_1$-$C_6$ alkyl, substituted with methoxy, methylthio, or halogen.

In a more specific embodiment, this invention provides a compound of formula IA1, IA2, IA3, IA4, or IA5, where X is O, $R_2$, and R' are H, $R_3$ and $R_4$ are methyl or methoxy, $R_5$ is $C_5$-$C_6$ alkyl, and q=zero.

In another embodiment, this invention provides a compound of formula IB1, IB2, IB3, IB4 or IB5, where X is O, $R_2$, and R' are H, $R_3$ and $R_4$ are methyl or methoxy, $R_5$ is $C_5$-$C_6$ alkyl, and q=zero.

DETAILED DESCRIPTION OF THE INVENTION

As used herein, the term heterocycloalkyl denotes a saturated carbocyclic moiety in which one or more ring carbon atoms is replaced by an atom selected from O, N, and S. As used herein, the term heterocycloalkenyl denotes a mono- or poly-unsaturated carbocyclic moiety in which one or more ring carbon atoms is replaced by an atom selected from O, N, and S. As used herein, the term heteroaryl denotes a mono- or bi-cyclic aromatic ring system with one or more ring atoms equal to O, N, and/or S.

Prophetic Examples

The examples below are intended to illustrate—but not to limit—the range of compounds contemplated by this invention.

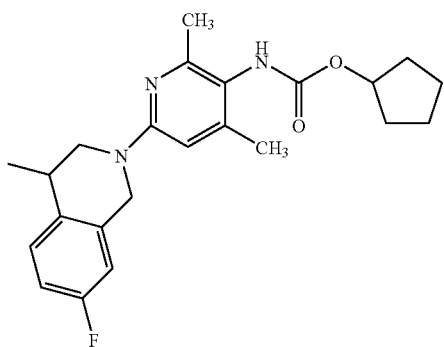

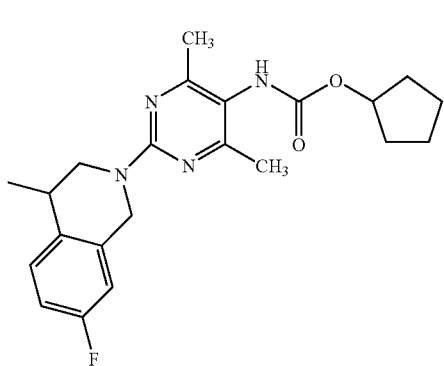

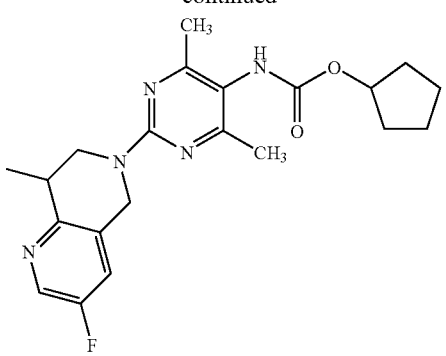

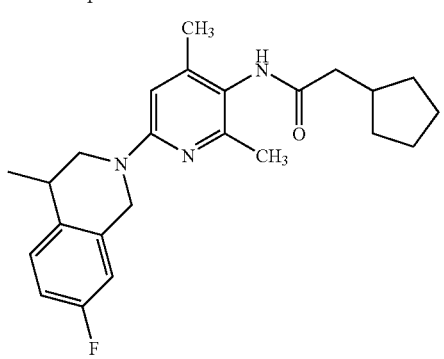

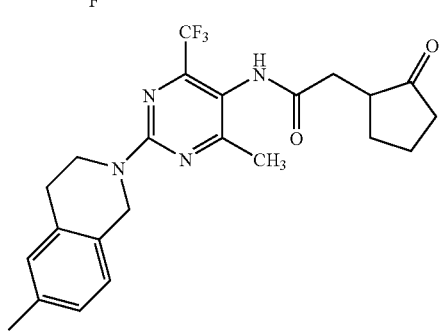

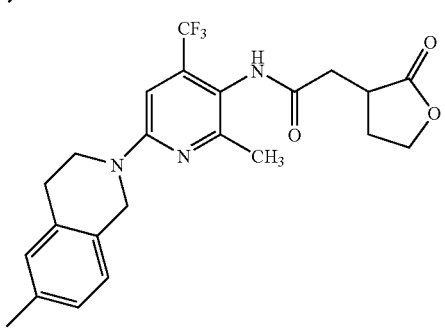

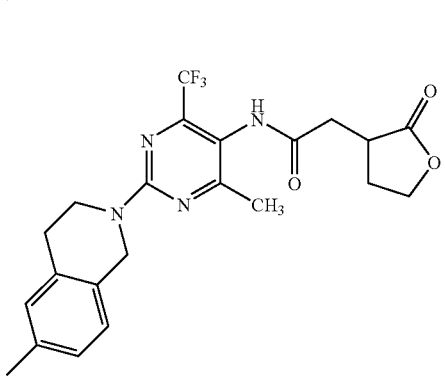

-continued
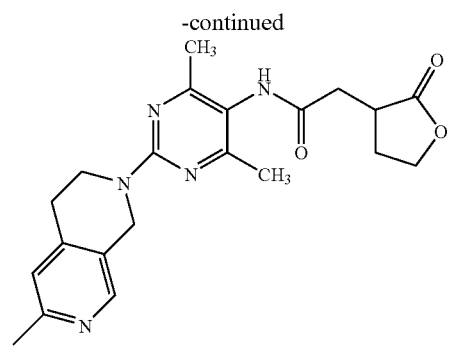
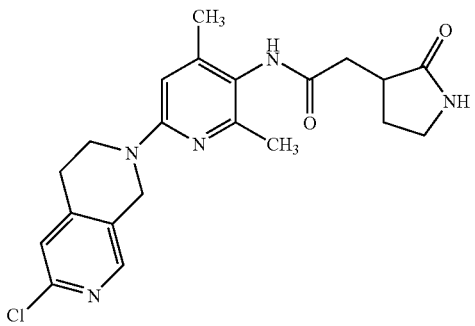
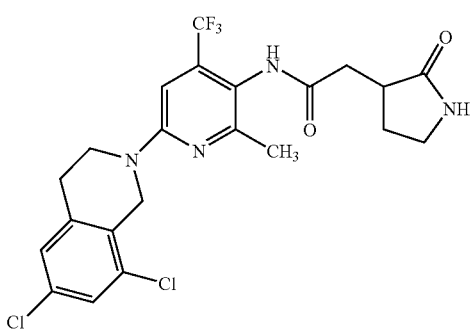
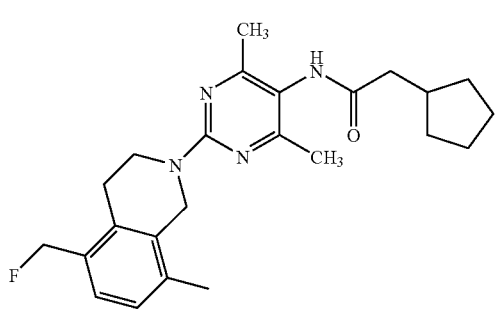
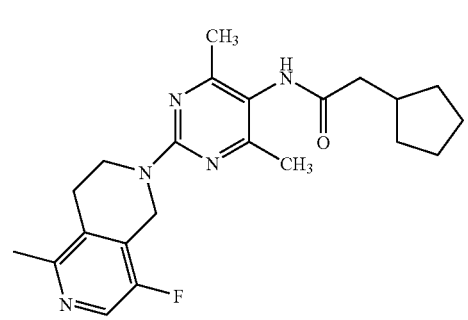
-continued
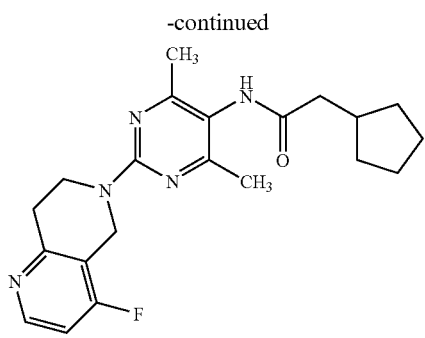
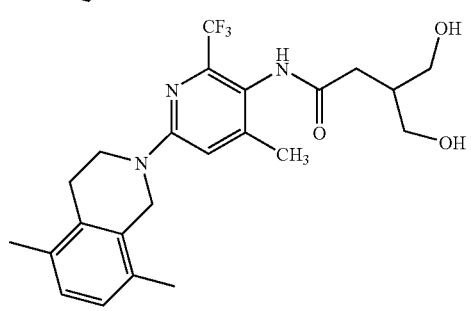
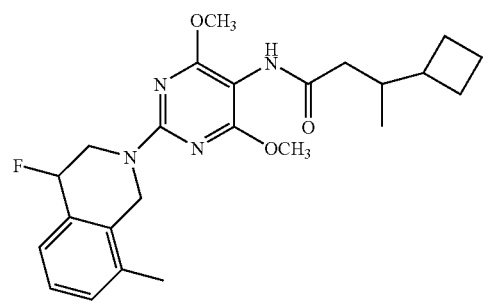
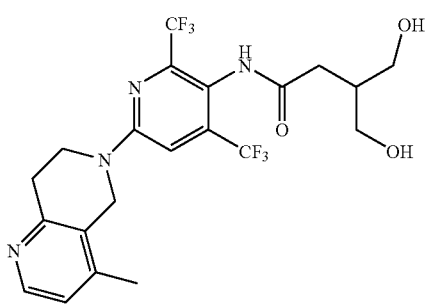
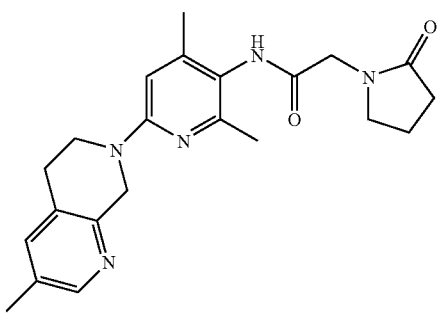

-continued
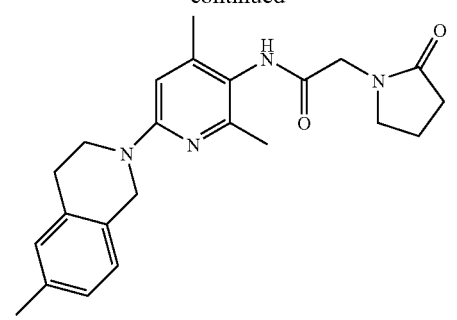
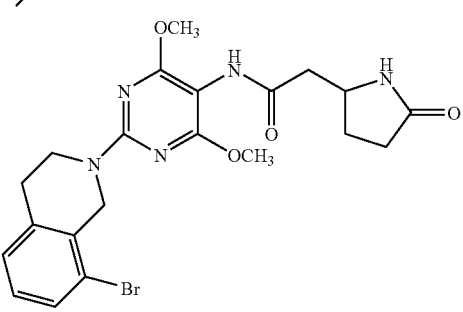
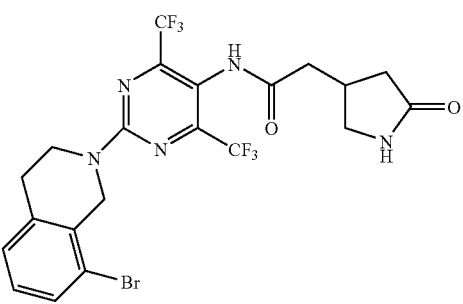
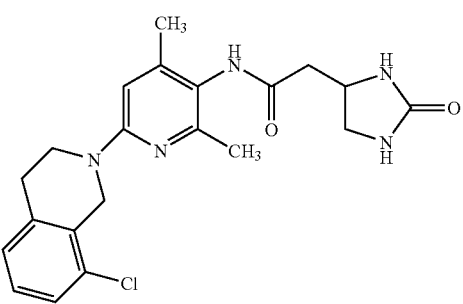
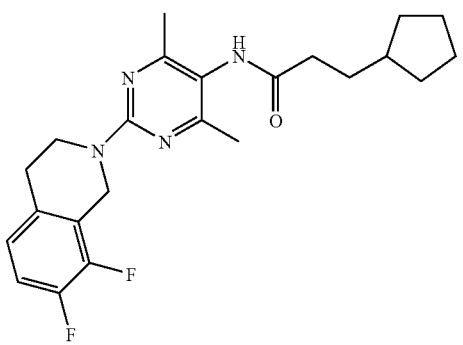
-continued
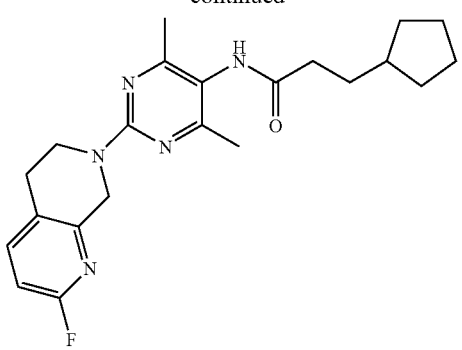
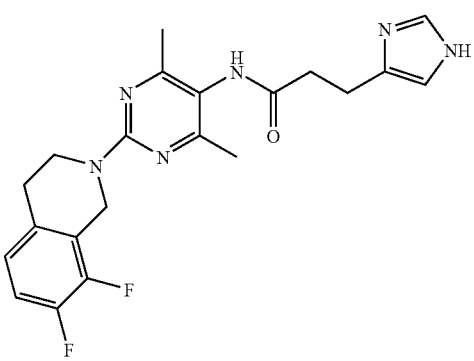
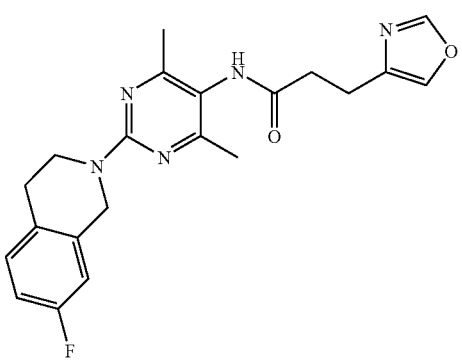
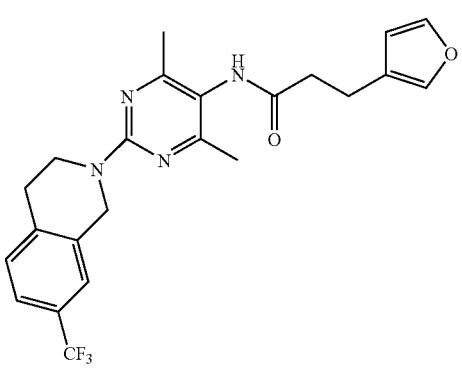

25
-continued
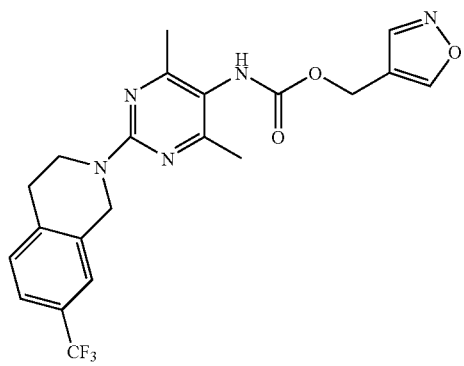
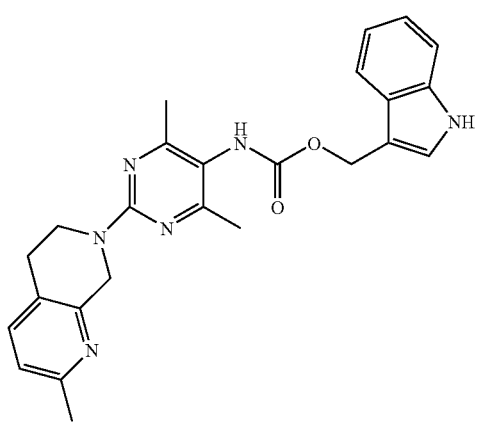
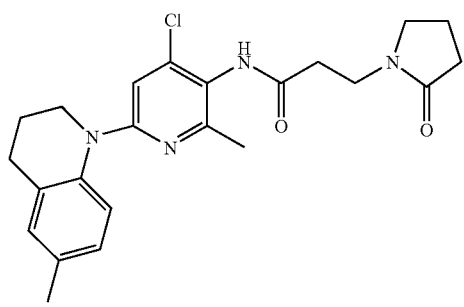
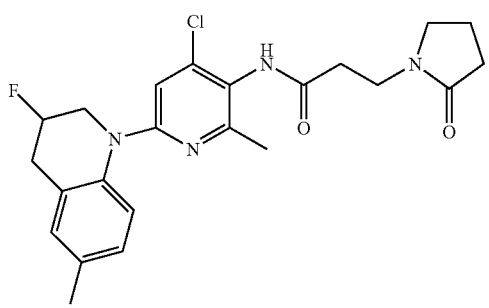
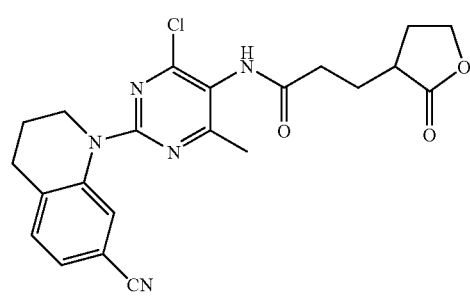
26
-continued
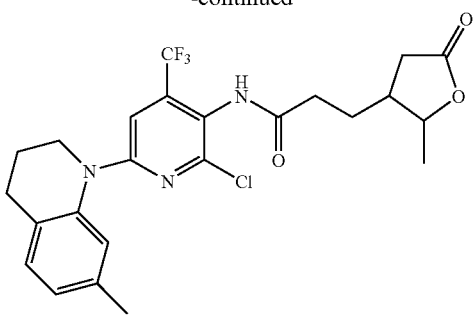
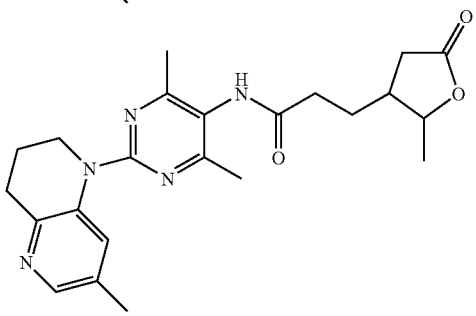
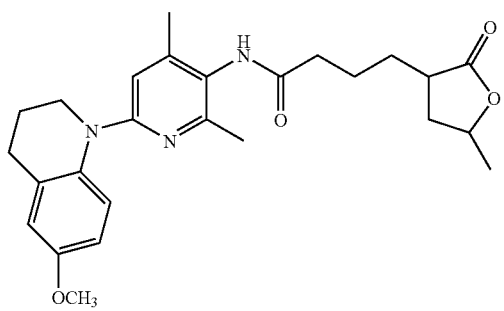
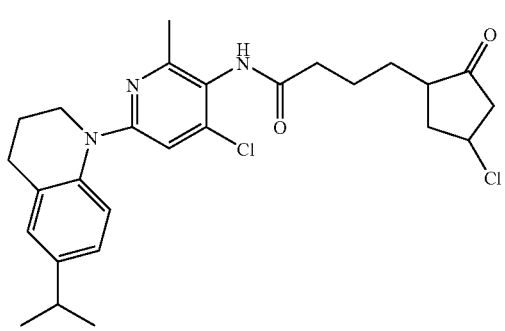
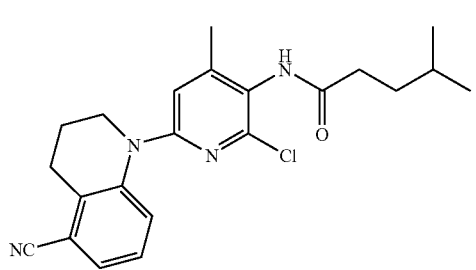

27
-continued
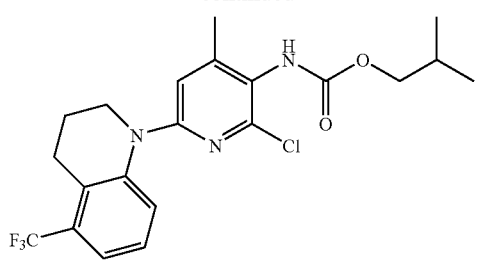
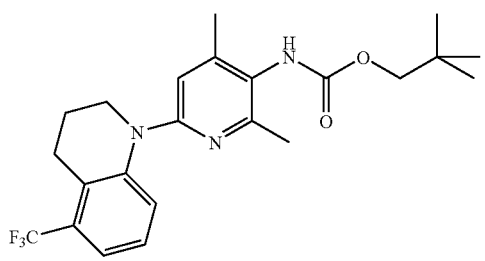
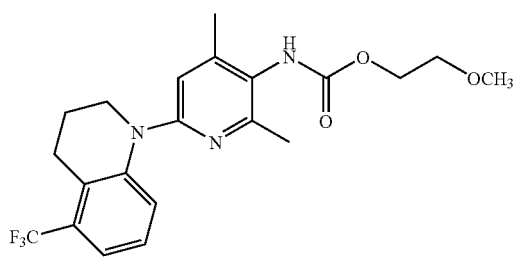
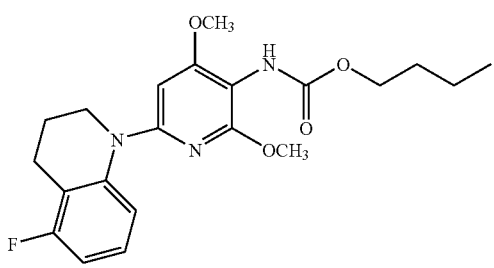
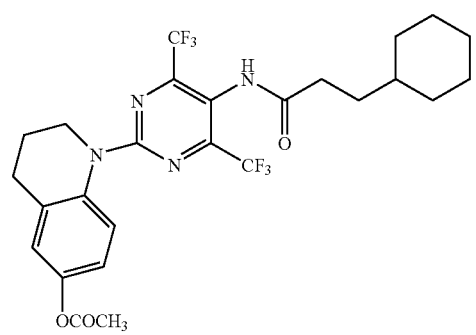
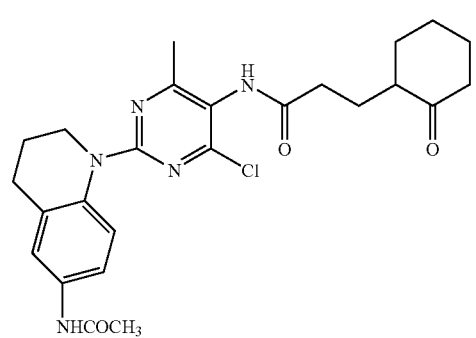
28
-continued
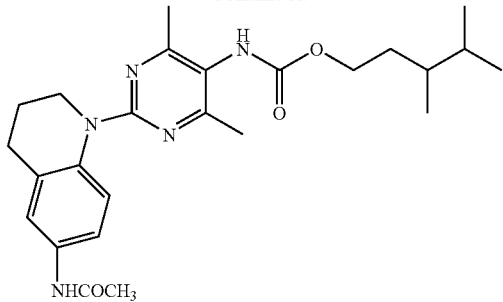
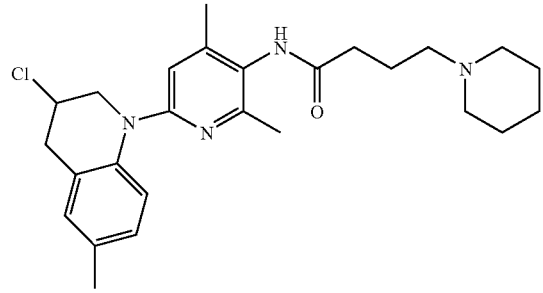
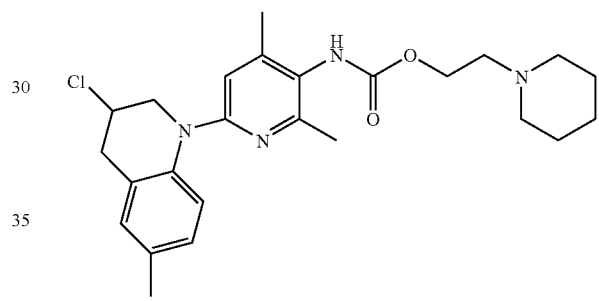
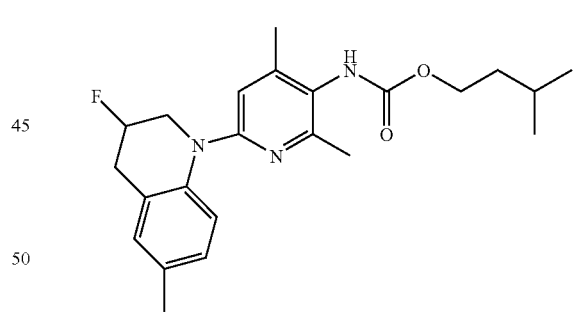
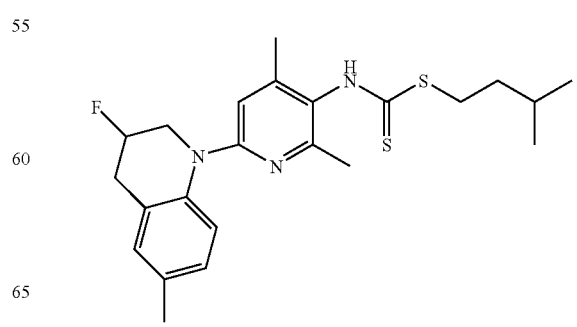

-continued
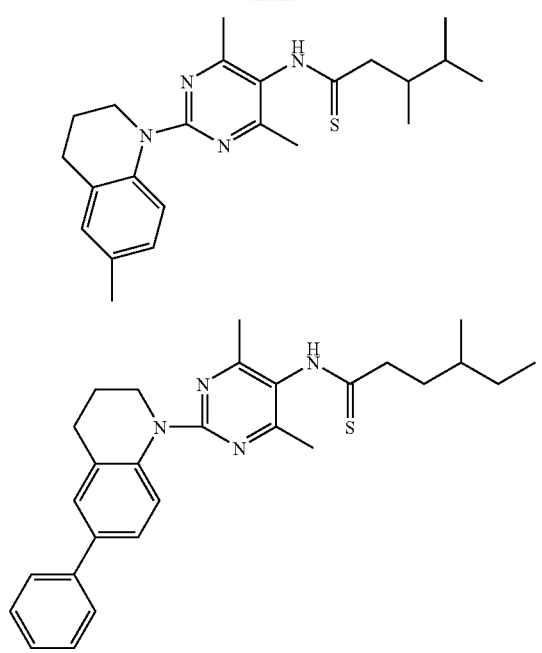
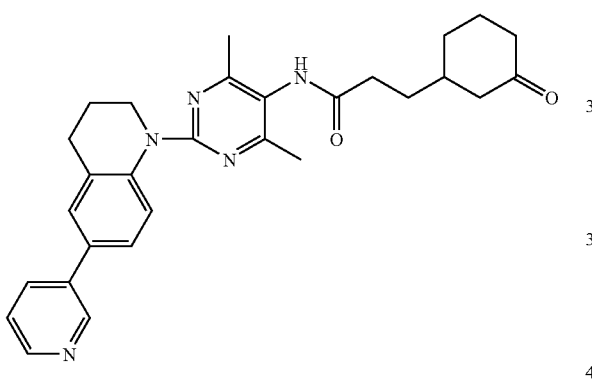
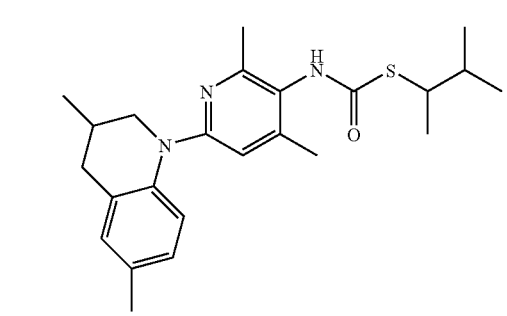
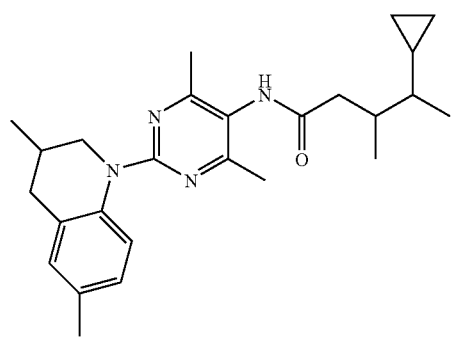
-continued
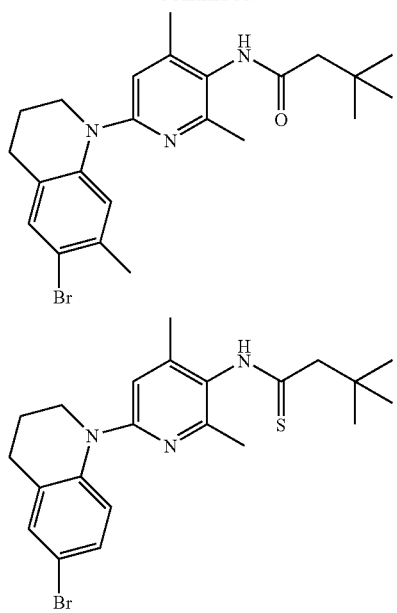
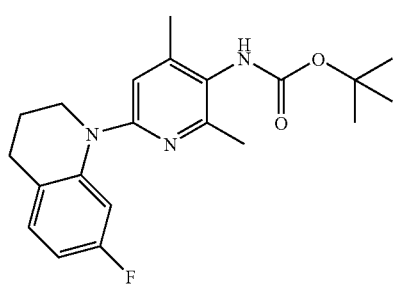
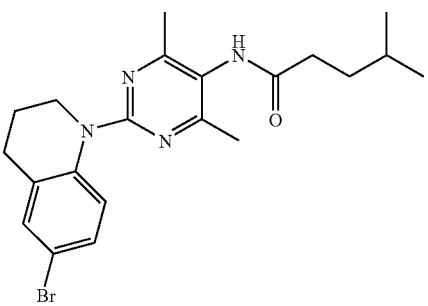
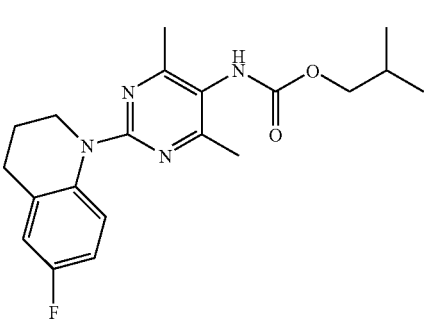

-continued
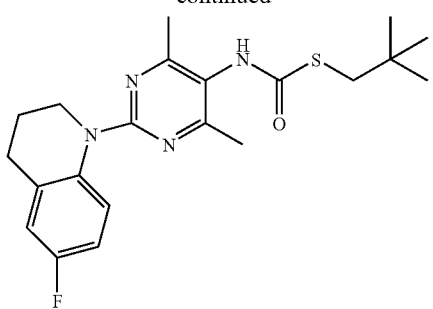
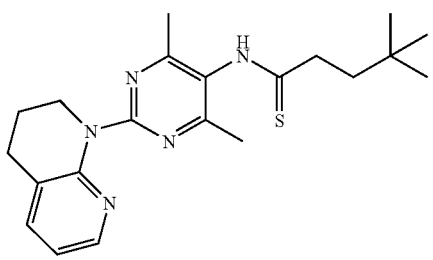
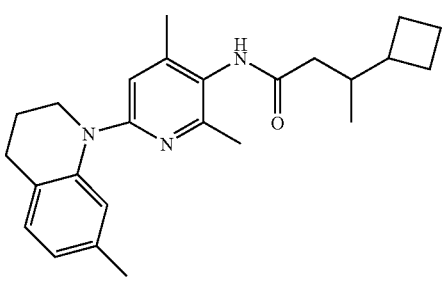
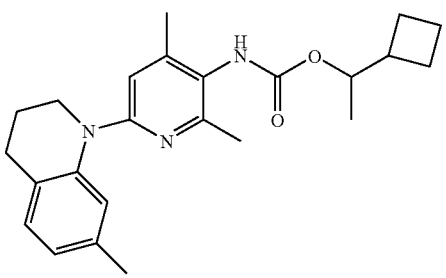
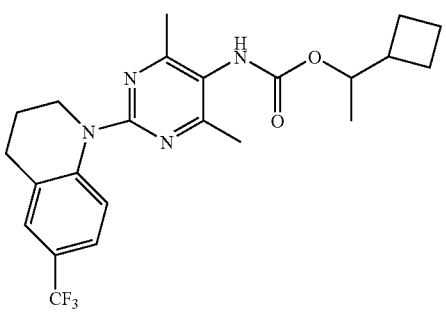
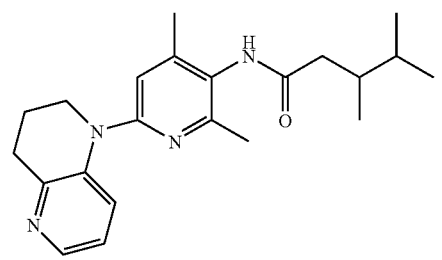
-continued
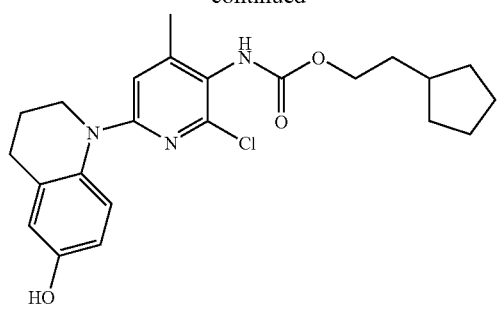
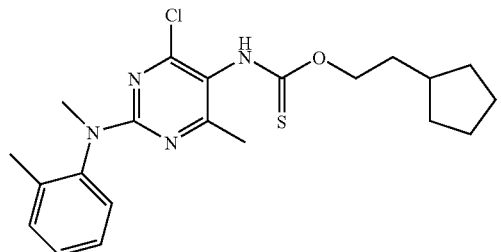
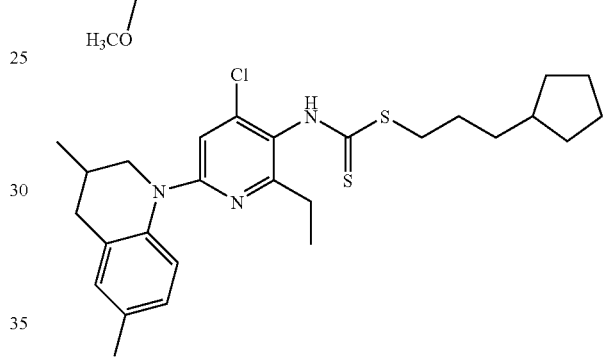
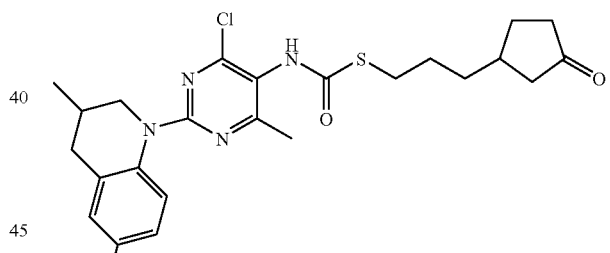
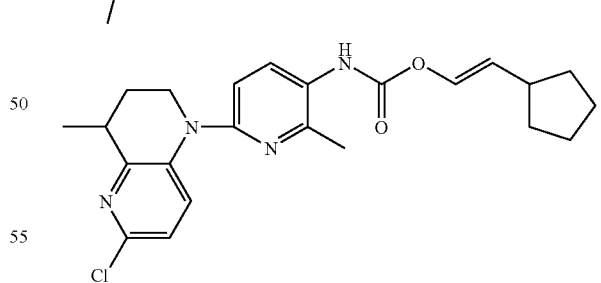
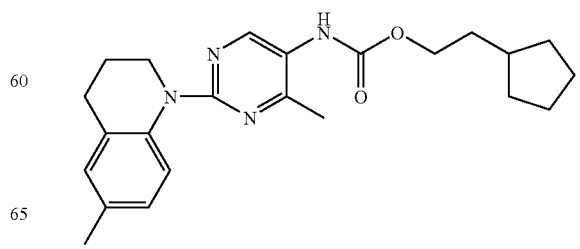

-continued
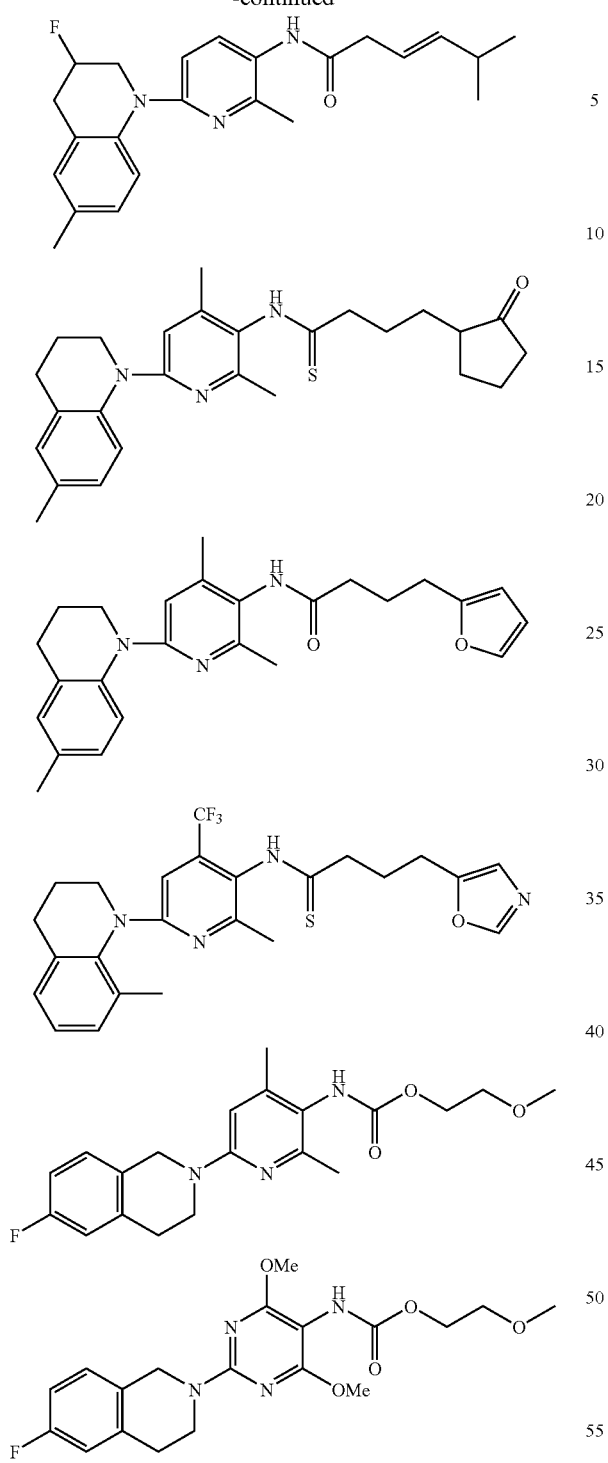
Preparation of Compounds
Preparation of Compounds as Potential KCNQ Channel Opener
Section I. The preparation of compounds of formula VIII is outlined in Scheme 1.
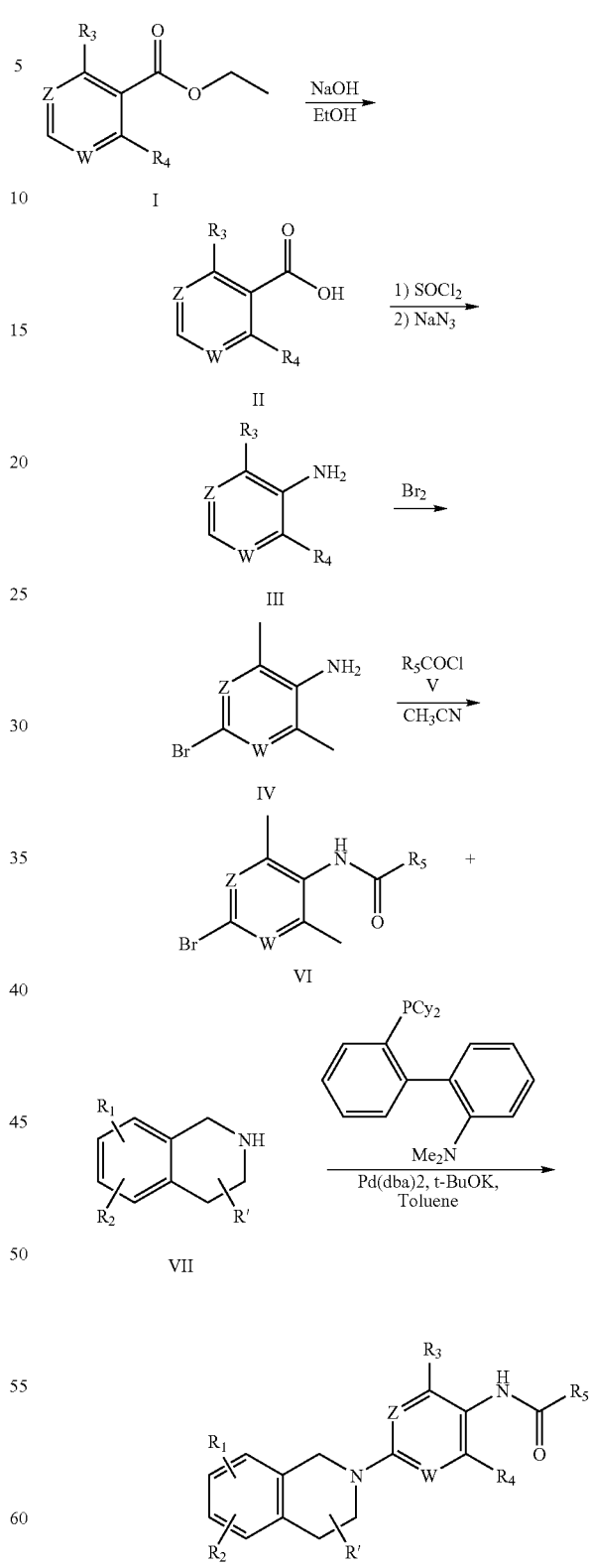
Section II. The preparation of compounds of formula XI is outlined in Scheme 2.

Scheme 2:
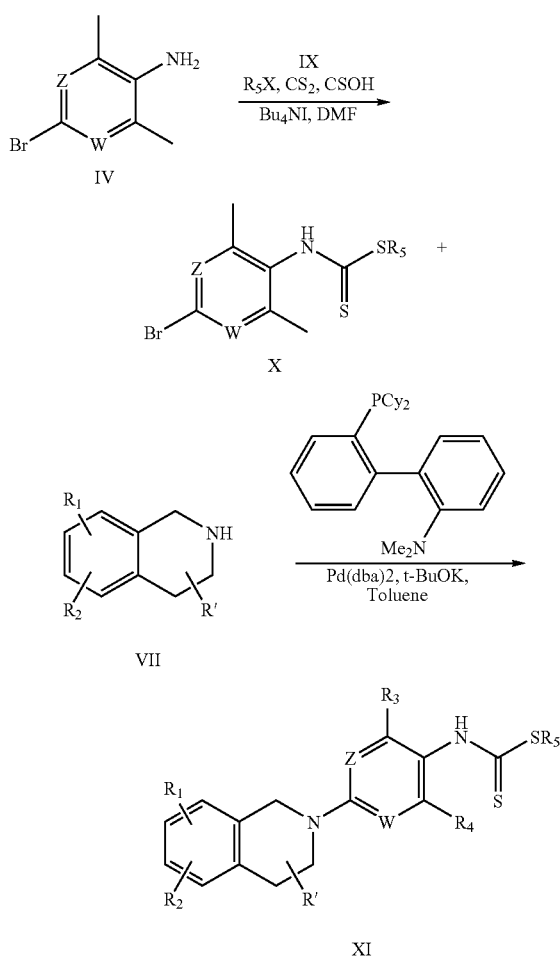
Section III. The preparation of compound of formula XIV is outlined in Scheme 3.
Scheme 3:
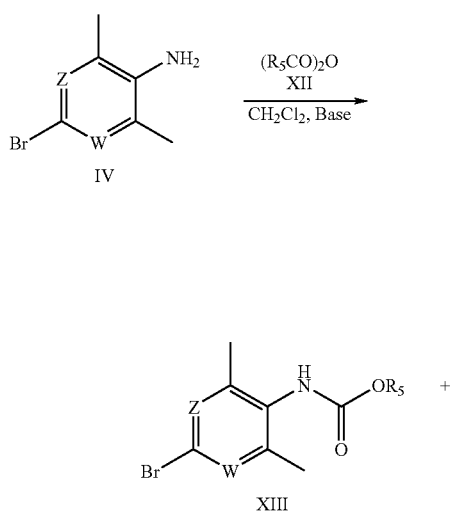
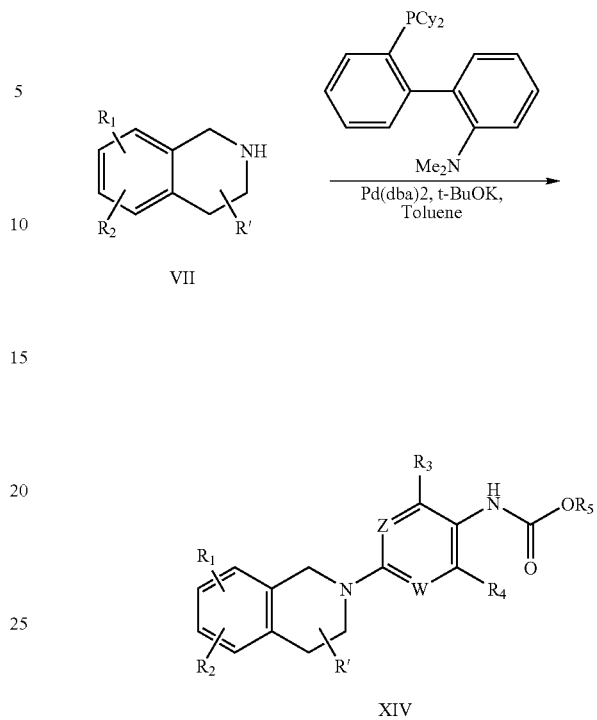
Section IV. The preparation of compound of formula XV is outlined in Scheme 4.
Scheme 4:
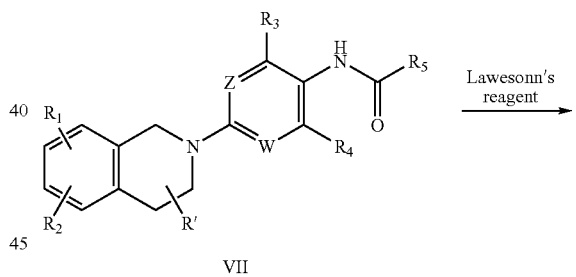
Section V. The preparation of compound of formula XVI is outlined in Scheme 5.

Scheme 5:

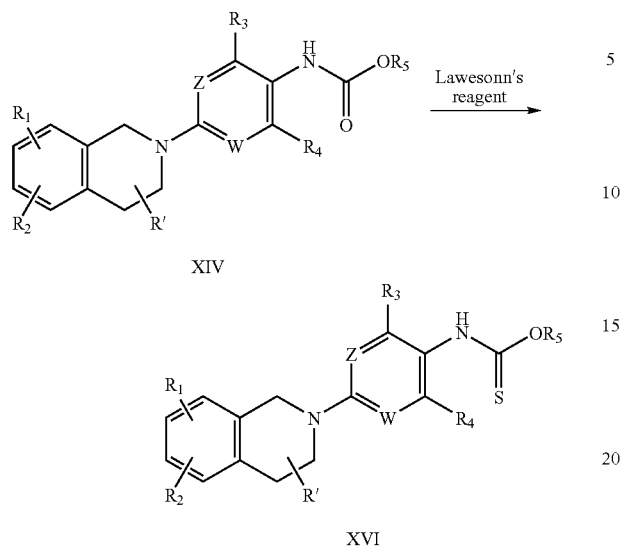

Section VI. The preparation of compound of formula XX is outlined in Scheme 6.

Scheme 6:

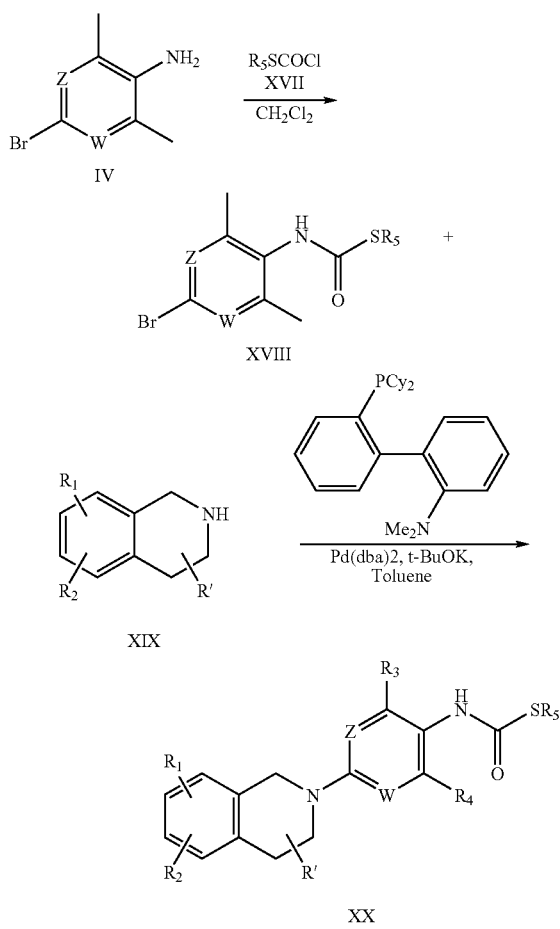

EXAMPLES

Example 1

N-(6-(3,4-dihydroisoquinolin-2(1H)-yl)-2,4-dimethylpyridin-3-yl)-3,3-dimethylbutanamide

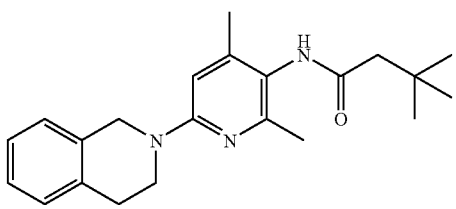

Step 1. Synthesis of 2,4-dimethylnicotinic acid, 1a

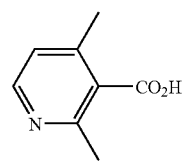

A mixture of ethyl 2,4-dimethylnicotinate (3.58 g, 20 mmol) and an aqueous solution of NaOH (10M, 20 ml) in ethanol (20 ml) was stirred at room temperature for 24 hours. The mixture was cooled to 0° C. and methanol (200 ml) was added follow by aqueous HCl (10 M) to adjust pH to 7. The resulting precipitated (NaCl) was filtered off.

The filtrated was concentrated to remain approximately 20 ml and methanol (100 ml) was added again to precipitate the remaining sodium chloride. The precipitation (NaCl) was repeated until all NaCl was removed from methanolic solution of the reaction mixture. The mixture was concentrated to dryness to yield 1a (3.01 g, 19.9 mmol, 99%).

Step 2. Synthesis of 2,4-dimethyl-3-aminopyridine, 1b

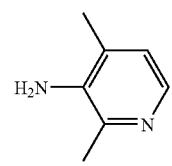

A mixture of 1a (0.98 g, 6.5 mmol) and thionyl chloride (5 ml) was heated to 60° C. for 1 hour. The mixture was concentrated to dryness. The mixture was then dissolved in acetone (10 ml) prior to the addition of NaN$_3$ (0.65 g, 10 mmol) and water (5 ml). The solution was heated to 70° C. for 1 hour. Acetone was evaporated from the reaction mixture which was washed with brine and extracted with ethyl acetate. The organic layer was dried over MgSO₄, concentrated and chromatographed to yield 1b (0.585 g, 4.79 mmol, 74%).

Step 3. Synthesis of 6-bromo-2,4-dimethyl-3-aminopyridine, 1c

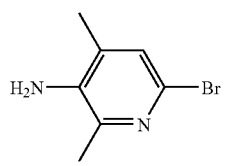

A solution of bromine in dichloromethane (0.96 g in 5 ml) was added to a solution of 1b (0.585, 4.79 mmol) in dichloromethane (25 ml) at 0° C. over 5 minutes. The mixture was warmed to room temperature and stirred for 2 hours. The mixture was washed with brine, extracted with ethyl acetate and chromatographed to yield 3c (0.364 g, 1.81 mmol, 38%).

Step 4. Synthesis of N-(6-bromo-2,4-dimethylpyridin-3-yl)-3,3-dimethylbutanamide, 1d

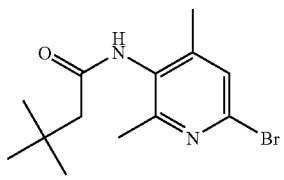

To a mixture of 1c (0.364 g, 1.81 mmol) and pyridine (0.158 ml, 2 mmol) in dichloromethane (5 ml) was added tert-butylacetyl chloride (0.242 g, 1.8 mmol). The mixture was stirred at room temperature for 2 hours. The mixture was washed with brine and extracted with ethyl acetate. The organic layer was dried over MgSO₄, concentrated and chromatographed to yield 1d (0.361 g, 1.64 mmol, 91%).

Step 5. Synthesis of N-(6-(3,4-dihydroisoquinolin-2 (1H)-yl)-2,4-dimethylpyridin-3-yl)-3,3-dimethylbutanamide

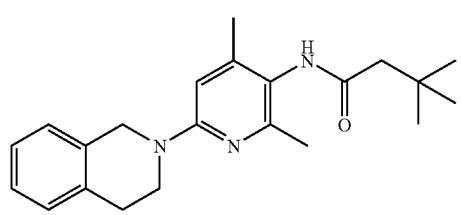

In a tube, a mixture of 1d (0.299 g, 1.0 mmol), 1,2,3,4-tetrahydroisoquinoline (0.20 g, 1.5 mmol) in toluene (10 ml) was degassed by nitrogen flow for 15 minutes. To this mixture was added tris(dichlorobenzylidenacetone)palladium (0) (0.046 g, 0.05 mmol), 2-dicyclohexylphosphino-2'-(N,N-dimethylamino)biphenyl (0.06 g, 0.15 mmol) and potassium tert-butoxide (0.168 g, 1.5 mmol). The tube was heated under microwave irradiation (Biotage Initiator®) for 2 hour at 100° C. The reaction mixture was cooled to room temperature, washed with water and extracted with ethyl acetate. The organic layer was washed with brine, dried over MgSO₄, concentrated and chromatographed to yield the title product (0.278 g, 0.79 mmol, 79%). $^1$H NMR (CDCl₃, 400 MHz) δ 1.14 (s, 9H), 2.19 (s, 3H), 2.27 (s, 2H), 2.35 (s, 3H), 2.93 (t, J=6.2 Hz, 2H), 3.84 (t, J=6.2 Hz, 2H), 4.66 (s, 2H), 6.39 (s, 1H), 6.49 (bs, 1H), 7.15-7.19 (m, 4H).

Example 2

N-(6-(6-fluoro-3,4-dihydroisoquinolin-2(1H)-yl)-2, 4-dimethylpyridin-3-yl)-3,3-dimethylbutanamide

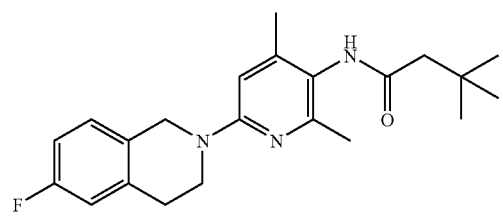 [SMILES: Cc1cc(N2CCc3cc(F)ccc3C2)nc(C)c1NC(=O)CC(C)(C)C]

In a tube, a mixture of 1d (0.65 g, 2.15 mmol), 6-fluoro-1, 2,3,4-tetrahydroisoquinoline (0.348 g, 2.6 mmol) in toluene (15 ml) was degassed by nitrogen flow for 15 minutes. To this mixture was added tris(dichlorobenzylidenacetone)palladium (0) (0.052 g, 0.055 mmol), 2-dicyclohexylphosphino-2'-(N,N-dimethylamino)biphenyl (0.08 g, 0.2 mmol) and potassium tert-butoxide (0.437 g, 3.9 mmol). The tube was heated under microwave irradiation (Biotage Initiator®) for 6 hour at 100° C. The reaction mixture was cooled to room temperature, washed with water and extracted with ethyl acetate. The organic layer was washed with brine, dried over MgSO₄, concentrated and chromatographed to yield the title compound (0.584 g, 1.58 mmol, 73%). $^1$H NMR (CDCl₃, 400 MHz) δ 1.14 (s, 9H), 2.19 (s, 3H), 2.27 (s, 2H), 2.35 (s, 3H), 2.91 (t, J=6.2 Hz, 2H), 3.82 (t, J=6.2 Hz, 2H), 4.62 (s, 2H), 6.38 (s, 1H), 6.50 (bs, 1H), 6.85-6.92 (m, 2H), 7.09-7.16 (m, 1H).

Example 3

N-(2,4-dimethyl-6-(6-(trifluoromethyl)-3,4-dihydroisoquinolin-2(1H)-yl)pyridin-3-yl)-3,3-dimethylbutanamide

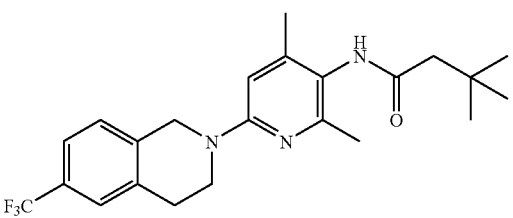 [SMILES: Cc1cc(N2CCc3cc(C(F)(F)F)ccc3C2)nc(C)c1NC(=O)CC(C)(C)C]

In a tube, a mixture of 1d (0.374 g, 1.25 mmol), 6-trifluoromethyl-1,2,3,4-tetrahydroisoquinoline (0.301 g, 1.5 mmol) in toluene (15 ml) was degassed by nitrogen flow for 15 minutes. To this mixture was added tris(dichlorobenzylidenacetone)palladium (0) (0.037 g, 0.04 mmol), 2-dicyclohexylphosphino-2'-(N,N-dimethylamino)biphenyl (0.06 g, 0.15 mmol) and potassium tert-butoxide (0.336 g, 3.0 mmol). The tube was heated under microwave irradiation (Biotage Initiator®) for 6 hour at 100° C. The reaction mixture was cooled to room temperature, washed with water and extracted with ethyl acetate. The organic layer was washed with brine, dried over MgSO₄, concentrated and chromatographed to yield the title compound (0.326 g, 0.78 mmol, 63%). ¹H NMR (CDCl₃, 400 MHz) δ 1.14 (s, 9H), 2.19 (s, 3H), 2.27 (s, 2H), 2.35 (s, 3H), 2.91 (t, J=6.2 Hz, 2H), 3.82 (t, J=6.2 Hz, 2H), 4.62 (s, 2H), 6.39 (s, 1H), 6.55 (bs, 1H), 6.98 (d, J=7.2 Hz, 2H), 7.24 (s, 1H).

Example 4

N-(2-(3,4-dihydroisoquinolin-2(1H)-yl)-4,6-dimethoxypyrimidin-5-yl)-3,3-dimethylbutanamide

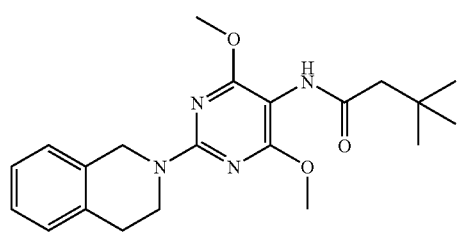 [SMILES: COc1nc(N2CCc3ccccc3C2)nc(OC)c1NC(=O)CC(C)(C)C]

Step 1. Synthesis of 2-chloro-4,6-dimethoxy-5-nitropyrimidine, 4a

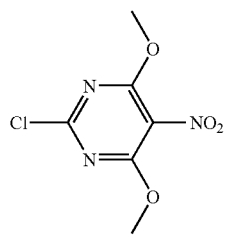

Triflic anhydride (4.25 g, 15 mmol) was added to a suspension of tetramethylammonium nitrate (2.04 g, 15 mmol) in dichloromethane (40 ml) at 0° C. over 15 minutes. The mixture was warmed to room temperature and stirred for 2 hours and then a solution of 2-chloro-4,6-dimethoxypyrimidine (1.75 g in 10 ml, 10 mmol) was added to the mixture over 30 minutes. The mixture was stirred for 2 days. The reaction mixture was poured into ice bath, washed with an aqueous solution of NaHCO₃ and extracted with dichloromethane. The organic layer was washed with brine, concentrated to dryness to yield 4a (2.13 g, 9.73 mmol, 97%).

Step 2. Synthesis of 2-(4,6-dimethoxy-5-nitropyrimidin-2-yl)-1,2,3,4-tetrahydroisoquinoline, 4b

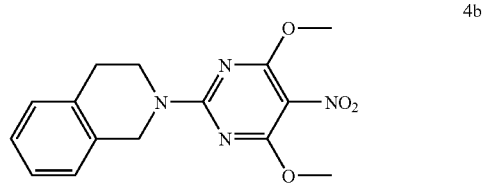 [SMILES: COc1nc(N2CCc3ccccc3C2)nc(OC)c1[N+](=O)[O-]]

1,8-diazabicyclo[5.4.0]undec-7-ene (0.304 g, 2 mmol) was added to a mixture of 4a (0.438 g, 2 mmol) and 1,2,3,4-tetrahydroisoquinoline (0.293 g, 2.2 mmol) in DMF (3 ml) at 0° C. over 5 minutes. The mixture was stirred for an additional 5 minutes at room temperature. The mixture was washed with brine, extracted with ethyl acetate and chromatographed to yield 4b (0.592 g, 1.87 mmol, 94%).

Step 3. Synthesis of 2-(3,4-dihydroisoquinolin-2(1H)-yl)-4,6-dimethoxypyrimidin-5-amine, 4c

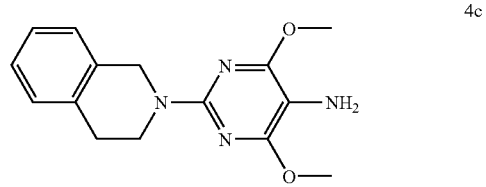 [SMILES: COc1nc(N2CCc3ccccc3C2)nc(OC)c1N]

A suspension of Raney®-Nickel in a methanolic solution of 4b (0.57 g in 50 ml, 1.8 mmol) was shaken under 50 psi of hydrogen atmosphere for 12 hours. The mixture was filtered and the filtrate was concentrated and used for the next step without further purification (0.51 g, 1.78 mmol, 99%).

Step 4. Synthesis of N-(2-(3,4-dihydroisoquinolin-2(1H)-yl)-4,6-dimethoxypyrimidin-5-yl)-3,3-dimethylbutanamide. 4d

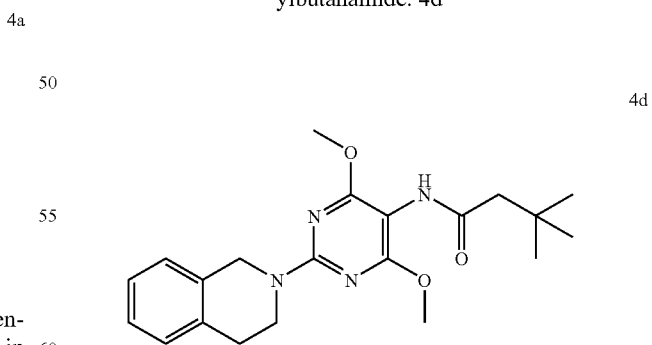

To a mixture of 4c (0.219 g, 0.76 mmol) and pyridine (0.06 g, 0.76 mmol) in dichloromethane (5 ml) was added tert-butylacetyl chloride (0.102 g, 0.76 mmol). The mixture was stirred at room temperature for 1 hour. The mixture was washed with brine and extracted with ethyl acetate. The organic layer was dried over MgSO₄, concentrated and chromatographed to yield the title compound (0.262 g, 0.73 mmol, 96%). $^1$H NMR (CDCl$_3$, 400 MHz) δ 1.10 (s, 9H), 2.20 (s, 2H), 2.90 (t, J=5.8 Hz, 2H), 3.92 (s, 6H), 4.01 (t, J=5.8 Hz, 2H), 4.87 (s, 2H), 6.14 (s, 1H), 7.15-7.19 (m, 4H).

Example 5

N-(4,6-dimethoxy-2-(6-(trifluoromethyl)-3,4-dihydroisoquinolin-2(1H)-yl)pyrimidin-5-yl)-3,3-dimethylbutanamide

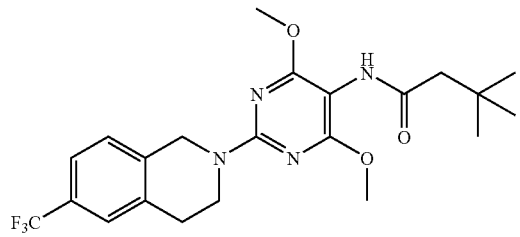 [SMILES: COc1nc(N2CCc3cc(C(F)(F)F)ccc3C2)nc(OC)c1NC(=O)CC(C)(C)C]

Step 1. Refer to example 4

Step 2. Synthesis of 2-(4,6-dimethoxy-5-nitropyrimidin-2-yl)-6-(trifluoromethyl)-1,2,3,4-tetrahydroisoquinoline, 5b

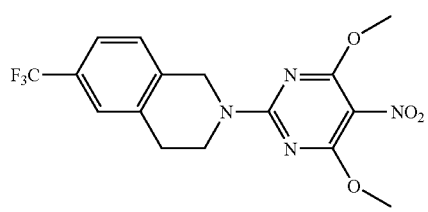

5b 1,8-diazabicyclo[5.4.0]undec-7-ene (0.669 g, 4.4 mmol) was added to a mixture of 4a (0.438 g, 2 mmol) and 6-(trifluoromethyl)-1,2,3,4-tetrahydroisoquinoline hydrochloride (0.487 g, 2.05 mmol) in DMF (5 ml) at 0° C. over 5 minutes. The mixture was stirred for an additional 5 minutes at room temperature. The mixture was washed with brine, extracted with ethyl acetate and chromatographed to yield 5b (0.76 g, 1.98 mmol, 99%).

Step 3. Synthesis of 4,6-dimethoxy-2-(6-(trifluoromethyl)-3,4-dihydroisoquinolin-2(1H)-yl)pyrimidin-5-amine, 5c

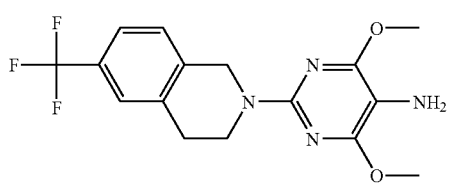

5c

A suspension of Raney®-Nickel in a methanolic solution of 5b (0.76 g in 50 ml, 1.98 mmol) was shaken under 50 psi of hydrogen atmosphere for 12 hours. The mixture was filtered and the filtrate was concentrated and used for the next step without further purification (0.69 g, 1.96 mmol, 99%).

Step 4. Synthesis of N-(4,6-dimethoxy-2-(6-(trifluoromethyl)-3,4-dihydroisoquinolin-2(1H)-yl)pyrimidin-5-yl)-3,3-dimethylbutanamide To a mixture of 5c (0.69 g, 1.96 mmol) and pyridine (0.156 g, 2.0 mmol) in dichloromethane (20 ml) was added tert-butylacetyl chloride (0.269 g, 2.0 mmol). The mixture was stirred at room temperature for 1 hour. The mixture was washed with brine and extracted with ethyl acetate. The organic layer was dried over MgSO$_4$, concentrated and chromatographed to yield the title compound (0.657 g, 1.45 mmol, 72%). $^1$H NMR (CDCl$_3$, 400 MHz) δ 1.10 (s, 9H), 2.20 (s, 2H), 2.95 (t, J=5.8 Hz, 2H), 3.92 (s, 6H), 4.04 (t, J=5.8 Hz, 2H), 4.92 (s, 2H), 6.18 (s, 1H), 7.29 (d, J=7.8 Hz, 1H), 7.42 (s, 1H), 7.44 (d, J=7.8 Hz, 1H).

Example 6

N-(2-(3,4-dihydroisoquinolin-2(1H)-yl)-4,6-dimethylpyrimidin-5-yl)-3,3-

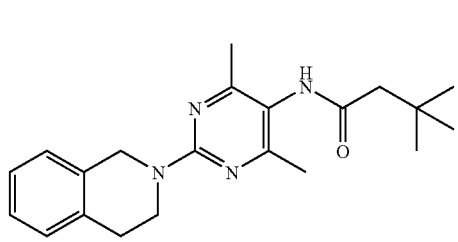 [SMILES: Cc1nc(N2CCc3ccccc3C2)nc(C)c1NC(=O)CC(C)(C)C]

Step 1. Synthesis of ethyl 2-hydroxy-4,6-dimethylpyrimidine-5-carboxylate. 6a

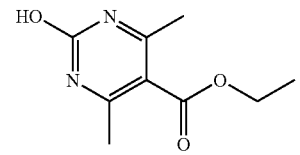

6a

A mixture of ethyl diacetoacetate (17.22 g, 100 mmol), urea (9.61 g, 160 mmol) and HCl (10 M, 4 ml) in ethanol (400 ml) was heated to 90° C. for 12 hours. The mixture was concentrated to remain 200 ml and then was cooled to −20° C.

to allow precipitation. The mixture was filtered at room temperature to obtained 6a as solid granulate (5.32 g, 2.71 mmol, 27%).

Step 2. Synthesis of ethyl
2-chloro-4,6-dimethylpyrimidine-5-carboxylate, 6b

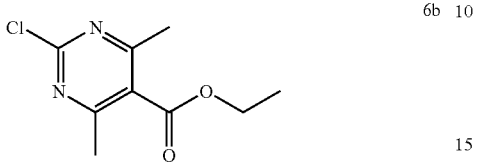

Phosphorus oxychloride (2.8 ml, 30 mmol) was added to a mixture of 6a (1.47 g, 7.5 mmol), benzyltriethylammonium chloride (1.71 g, 7.5 mmol) and N,N-dimethylaniline (1.82 g, 15 mmol) in acetonitrile (30 ml). The mixture was reflux for 5 hours. The mixture was poured into ice water and neutralized with $NaHCO_3$. The solution was extracted with ethyl acetate. The organic layer washed with brine, dried over $MgSO_4$, concentrated and chromatographed to obtain 6b, (1.02 g, 4.75 mmol, 63%).

Step 3. Synthesis of ethyl 2-(3,4-dihydroisoquinolin-2(1H)-yl)-4,6-dimethylpyrimidine-5-carboxylate, 6c

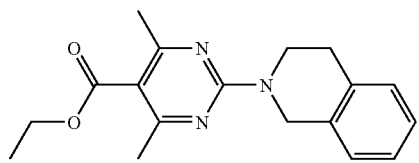

1,8-diazabicyclo[5.4.0]undec-7-ene (1.086 g, 7.15 mmol) was added to a mixture of 6b (1.02 g, 4.75 mmol) and 1,2,3,4-tetrahydroisoquinoline (0.95 g, 7.13 mmol) in DMSO (5 ml) at 0° C. over 5 minutes. The mixture was stirred for an additional 5 minutes at room temperature. The mixture was washed with brine, extracted with ethyl acetate and chromatographed to yield 6c (1.43 g, 4.5 mmol, 95%).

Step 4. Synthesis of 2-(3,4-dihydroisoquinolin-2(1H)-yl)-4,6-dimethylpyrimidine-5-carboxylic acid, 6d

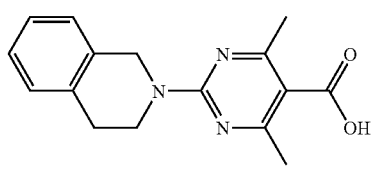

A mixture of 6c (1.43 g, 4.5 mmol) and an aqueous solution of NaOH (10M, 20 ml) in ethanol (20 ml) was refluxed for 6 hours. To the mixture was added 100 ml of water and then the mixture was washed with dichloromethane (100 ml). The aqueous phase was neutralized with hydrochloric acid to pH=6. Product was precipitated at pH=6. After filtration, 6d was obtained as white powder (1.10 g, 3.88 mmol, 86%).

Step 5. Synthesis of 2-(3,4-dihydroisoquinolin-2(1H)-yl)-4,6-dimethylpyrimidin-5-amine, 6e

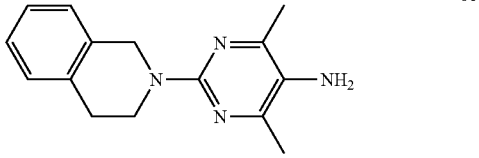

To a cold (−20° C.) thionyl chloride (5 ml) was added 9d (0.8 g, 2.82 mmol). The mixture was heated to 70° C. for 1 hour. Excess thionyl chloride was evaporated. The residue was dissolved in THF (3 ml) and acetone (3 ml) and then trimethylsilyl azide (0.55 ml, 4.25 mmol) was added into the mixture. The mixture was heated to 70° C. for 2 hours. The reaction media was washed with brine, extracted with ethyl acetate. Organic layer was dried over $MgSO_4$, concentrated and chromatographed to yield 6e (0.028 g, 0.11 mmol, 4%).

Step 6. Synthesis of N-(2-(3,4-dihydroisoquinolin-2(1H)-yl)-4,6-dimethylpyrimidin-5-yl)-N-(3,3-dimethylbutanoyl)-3,3-dimethylbutanamide, 6f

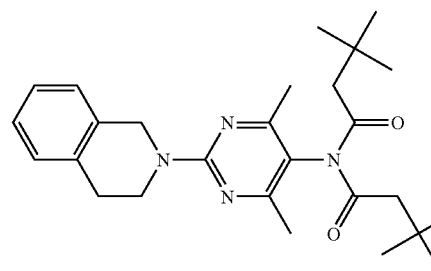

To a mixture of 6e (0.028 g, 0.11 mmol) and pyridine (0.03 g, 0.4 mmol) in dichloromethane (2 ml) was added tert-butylacetyl chloride (0.053 g, 0.4 mmol). The mixture was stirred at room temperature for 5 hour. The mixture was washed with brine and extracted with ethyl acetate. The organic layer was dried over MgSO$_4$, concentrated and chromatographed to yield 6f (0.031 g, 0.07 mmol, 63%).

Step 7. Synthesis of N-(2-(3,4-dihydroisoquinolin-2(1H)-yl)-4,6-dimethylpyrimidin-5-yl)-3,3-dimethylbutanamide

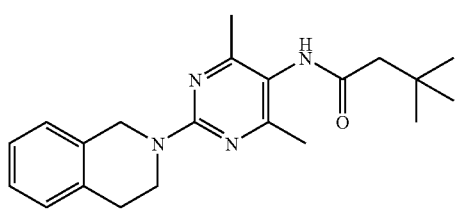 [SMILES: Cc1nc(N2CCc3ccccc3C2)nc(C)c1NC(=O)CC(C)(C)C]

An aqueous solution of ammonium hydroxide (30%, 1 ml) was added to a solution of 6f (0.031 g, 0.07 mmol) in methanol (1 ml) and stirred for 20 hours. The mixture was washed with brine and extracted with ethyl acetate. The organic layer was dried over MgSO$_4$, concentrated and chromatographed to yield the title compound (0.019 g, 0.054 mmol, 77%). $^1$H NMR (CDCl$_3$, 400 MHz) δ 1.11 (s, 9H), 2.23 (s, 2H), 2.30 (s, 6H), 2.91 (t, J=6.0 Hz, 2H), 4.04 (t, J=6.0 Hz, 2H), 4.89 (s, 2H), 6.68 (s, 1H), 7.17 (dd, J=7.8, 3.4 Hz, 4H).

Example 7

N-(6-(6-fluoro-3,4-dihydroisoquinolin-2(1H)-yl)-2,4-dimethylpyridin-3-yl)-2-(2-methoxyethoxy)acetamide

Step 1. Synthesis of N-(6-bromo-2,4-dimethylpyridin-3-yl)-2-(2-methoxyethoxy)acetamide

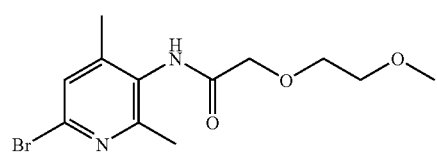

7d

To a mixture of 1c (0.5114 g, 2.54 mmol) and pyridine (0.22 ml, 2.78 mmol) in dichloromethane (5 ml) was added 2-(2-methoxyethoxy)acetyl chloride (0.425 g, 2.78 mmol). The mixture was stirred at room temperature overnight. The mixture was washed with brine and extracted with ethyl acetate. The organic layer was dried over MgSO$_4$, concentrated and chromatographed to yield 7d (0.72 g, 2.27 mmol, 90%).

Step 2. N-(6-(6-fluoro-3,4-dihydroisoquinolin-2(1H)-yl)-2,4-dimethylpyridin-3-yl)-2-(2-methoxyethoxy)acetamide

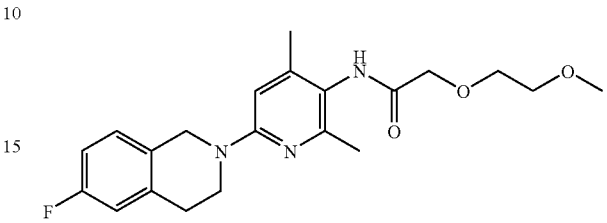

In a tube, a mixture of 7d (0.245 g, 0.77 mmol), 6-fluoro-1,2,3,4-tetrahydroisoquinoline (0.1876 g, 1.0 mmol) in toluene (5 ml) was degassed by nitrogen flow for 15 minutes. To this mixture was added tris(dichlorobenzylidenacetone)palladium (0) (0.025 g, 0.027 mmol), 2-dicyclohexylphosphino-2'-(N,N-dimethylamino)biphenyl (0.04 g, 0.1 mmol) and potassium tert-butoxide (0.336 g, 3.0 mmol). The tube was heated under microwave irradiation (Biotage Initiator®) for 6 hour at 100° C. The reaction mixture was cooled to room temperature, washed with water and extracted with ethyl acetate. The organic layer was washed with brine, dried over MgSO$_4$, concentrated and chromatographed to yield the title compound (0.259 g, 0.668 mmol, 87%). $^1$H NMR (CDCl$_3$, 400 MHz) δ 2.19 (s, 3H), 2.36 (s, 3H), 2.92 (t, J=5.7 Hz, 2H), 3.40 (s, 3H), 3.62 (dd, J=4.3, 2.2 Hz, 2H), 3.80-3.84 (m, 4H), 4.19 (s, 2H), 4.64 (s, 2H), 6.40 (s, 1H), 6.85-6.91 (m, 2H), 7.14 (dd, J=7.9, 7.9 Hz, 1H), 8.21 (bs, 1H).

Example 8

N-(2,4-dimethyl-6-(6-(trifluoromethyl)-3,4-dihydroisoquinolin-2(1H)-yl)pyridin-3-yl)-2-(2-methoxyethoxy)acetamide

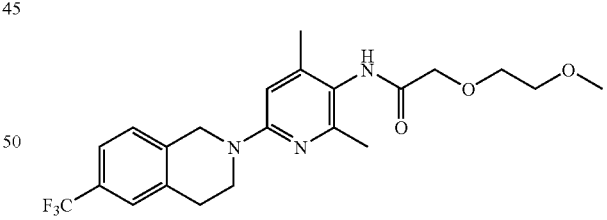

In a tube, a mixture of 7d (0.2 g, 0.6 mmol), 6-trifluoromethyl-1,2,3,4-tetrahydroisoquinoline (0.209 g, 0.88 mmol) in toluene (5 ml) was degassed by nitrogen flow for 15 minutes. To this mixture was added tris(dichlorobenzylidenacetone) palladium (0) (0.025 g, 0.027 mmol), 2-dicyclohexylphosphino-2'-(N,N-dimethylamino)biphenyl (0.04 g, 0.1 mmol) and potassium tert-butoxide (0.224 g, 2.0 mmol). The tube was heated under microwave irradiation (Biotage Initiator®) for 6 hour at 100° C. The reaction mixture was cooled to room temperature, washed with water and extracted with ethyl acetate. The organic layer was washed with brine, dried over MgSO$_4$, concentrated and chromatographed to yield the title compound (0.262 g, 0.6 mmol, 95%). $^1$H NMR (CDCl$_3$, 400

MHz) δ 2.18 (s, 3H), 2.35 (s, 3H), 2.96 (t, J=5.5 Hz, 2H), 3.37 (s, 3H), 3.62 (dd, J=3.8, 1.6 Hz, 2H), 3.78-3.84 (m, 4H), 4.17 (s, 2H), 4.71 (s, 2H), 6.41 (s, 1H), 7.27 (d, J=7.7, 1H), 7.40 (s, 1H) 7.41 (d, J=8.4 Hz, 1H), 8.25 (bs, 1H).

Example 9

N-(2,4-dimethyl-6-(7-(trifluoromethyl)-3,4-dihydroisoquinolin-2(1H)-yl)pyridin-3-yl)-3,3-dimethylbutanamide

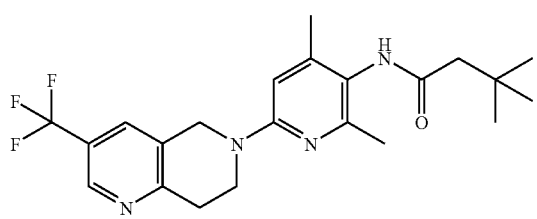 [SMILES: Cc1cc(N2CCc3ncc(C(F)(F)F)cc3C2)nc(C)c1NC(=O)CC(C)(C)C]

Bis(dibenzylidineacetone)palladium (4 mg, 0.069 mmol) and (2'-dicyclohexylphosphanyl-biphenyl-2-yl)-dimethylamine (6.5 mg, 0.014 mmol) were added to dry toluene (1 mL purged with argon) and stirred for 15 minutes under argon. Potassium tert-butoxide (34 mg, 0.3 mmol), 1d (50 mg, 0.17 mmol) and 3-(trifluoromethyl)-5,6,7,8-tetrahydro-1,6-naphthyridine (28 mg, 0.14 mmol) were then added and the reaction mixture was stirred at 80° C. over night. The reaction mixture was then cooled to room temperature, concentrated and purified by biotage (75% ethyl acetate:hexanes) to afford the tittle compound as a solid. $^1$H NMR (DMSO-d$_6$, 400 MHz) δ 1.03 (s, 9H), 2.09 (s, 3H), 2.15 (s, 2H), 2.21 (s, 3H), 3.03 (t, J=4 Hz, 2H), 3.92 (t, J=4 Hz, 2H), 4.79 (s, 2H), 6.68 (s, 1H), 8.12 (s, 1H), 8.75 (s, 1H), 9.02 (s, 1H).

Example 10

N-(6-(7,8-dihydropyrido[4,3-d]pyrimidin-6(5H)-yl)-2,4-dimethylpyridin-3-yl)-3,3-dimethylbutanamide

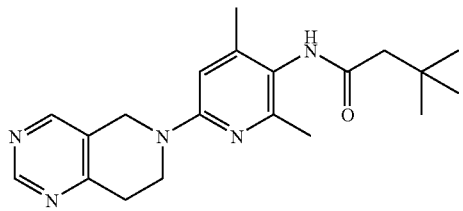 [SMILES: Cc1cc(N2CCc3ncncc3C2)nc(C)c1NC(=O)CC(C)(C)C]

Bis(dibenzylidineacetone)palladium (5 mg, 0.009 mmol) and (2'-dicyclohexylphosphanyl-biphenyl-2-yl)-dimethylamine (9 mg, 0.018 mmol) were added to dry toluene (1 mL purged with argon) and stirred for 15 minutes under argon. Potassium tert-butoxide (46 mg, 0.41 mmol), 1d (66 mg, 0.22 mmol) and 5,6,7,8-tetrahydropyrido[4,3-d]pyrimidine (25 mg, 0.19 mmol) were then added and the reaction mixture was stirred at 80° C. over night. The reaction mixture was then cooled to room temperature, concentrated and purified by biotage (75% Ethyl acetate:Hexanes) to afford the tittle compound as a solid. $^1$H NMR (CDCl$_3$, 400 MHz) δ 1.15 (s, 9H), 2.21 (s, 3H), 2.28 (s, 2H), 2.36 (s, 3H), 3.06 (t, J=4 Hz, 2H), 3.92 (t, J=4 Hz, 2H), 4.73 (s, 2H), 6.48 (s, 1H), 6.55 (s, 1H), 8.55 (s, 1H), 9.01 (s, 1H).

Example 11

N-(2,4-dimethyl-6-(2-(trifluoromethyl)-7,8-dihydropyrido[4,3-d]pyrimidin-6(5H)-yl)pyridin-3-yl)-3,3-dimethylbutanamide

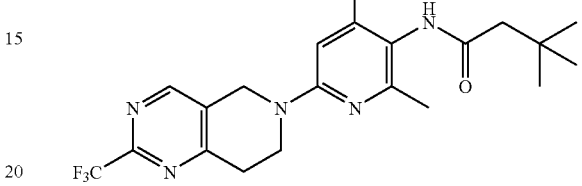

Bis(dibenzylidineacetone)palladium (4 mg, 0.07 mmol) and (2'-dicyclohexylphosphanyl-biphenyl-2-yl)-dimethylamine (6.5 mg, 0.014 mmol) were added to dry toluene (1 mL purged with argon) and stirred for 15 minutes under argon. Potassium tert-butoxide (34 mg, 0.31 mmol), 1d (50 mg, 0.18 mmol) and 2-(trifluoromethyl)-5,6,7,8-tetrahydropyrido[4,3-d]pyrimidine (28 mg, 0.14 mmol) were then added and the reaction mixture was stirred at 80° C. over night. The reaction mixture was then cooled to room temperature, concentrated and purified by biotage (75% Ethyl acetate: Hexanes) to afford compound 9 as a solid. $^1$H NMR (CDCl$_3$, 400 MHz) δ 1.14 (s, 9H), 2.21 (s, 3H), 2.28 (s, 2H), 2.36 (s, 3H), 3.17 (t, J=4 Hz, 2H), 3.92 (t, J=4 Hz, 2H), 4.83 (s, 2H), 6.51 (s, 1H), 8.70 (s, 1H).

Biological Results

Compounds of this invention formula were evaluated as potassium channel modulators by measuring rhubidium release in the following assay.

Methods: PC-12 cells were grown at 37° C. and 5% $CO_2$ in DMEM/F12 Medium supplemented with 10% horse serum, 5% fetal bovine serum, 2 mM glutamine, 100 U/ml penicillin, 100 U/ml streptomycin. They were plated in poly-D-lysine-coated 96-well cell culture microplates at a density of 40,000 cells/well and differentiated with 100 ng/ml NGF-7s for 2-5 days. For the assay, the medium was aspirated and the cells were washed once with 0.2 ml in wash buffer (25 mM Hepes, pH 7.4, 150 mM NaCl, 1 mM $MgCl_2$, 0.8 mM $NaH_2PO_4$, 2 mM $CaCl_2$). The cells were then loaded with 0.2 ml $Rb^+$ loading buffer (wash buffer plus 5.4 mM $RbCl_2$, 5 mM glucose) and incubated at 37° C. for 2 h. Attached cells were quickly washed three times with buffer (same as $Rb^+$ loading buffer, but containing 5.4 mM KCl instead of RbCl) to remove extracellular $Rb^+$. Immediately following the wash, 0.2 ml of depolarization buffer (wash buffer plus 15 mM KCl) with or without compounds was added to the cells to activate efflux of potassium ion channels. After incubation for 10 min at room temperature, the supernatant was carefully removed and collected. Cells were lysed by the addition of 0.2 ml of lysis buffer (depolarization buffer plus 0.1% Triton X-100) and the cell lysates were also collected. If collected samples were not immediately analyzed for $Rb^+$ contents by atomic absorption spectroscopy (see below), they were stored at 4° C. without any negative effects on subsequent $Rb^+$ analysis.

The concentration of $Rb^+$ in the supernatants ($Rb^+_{Sup}$) and cell lysates ($Rb^+_{Lys}$) was quantified using an ICR8000 flame atomic absorption spectrometer (Aurora Biomed Inc., Vancouver, B.C.) under conditions defined by the manufacturer. One 0.05 ml samples were processed automatically from microtiter plates by dilution with an equal volume of $Rb^+$ sample analysis buffer and injection into an air-acetylene flame. The amount of $Rb^+$ in the sample was measured by absorption at 780 nm using a hollow cathode lamp as light source and a PMT detector. A calibration curve covering the range 0-5 mg/L $Rb^+$ in sample analysis buffer was generated with each set of plates. The percent $Rb^+$ efflux (F) was defined by $F=[Rb^+_{sup}/(Rb^+_{sup}+Rb^+_{Lys})]\times 100\%$.

The effect (E) of a compound was defined by: $E=[(F_c-F_b)/(F_s-F_b)]\times 100\%$ where the $F_c$ is the efflux in the presence of compound in depolarization buffer, $F_b$ is the efflux in basal buffer, and $F_s$ is the efflux in depolarization buffer, and $F_c$ is the efflux in the presence of compound in depolarization buffer. The effect (E) and compound concentration relationship was plotted to calculate an $EC_{50}$ value, a compound's concentration for 50% of maximal $Rb^+$ efflux. The results are shown below. Legend: A: EC50=1 nM-50 nM; B: EC50=50 nM-100 nM; C: EC50=100-200 nM.

TABLE 1

ACTIVITIES OF EXEMPLARY COMPOUNDS

| COMPOUND | ACTIVITY |
|---|---|
| 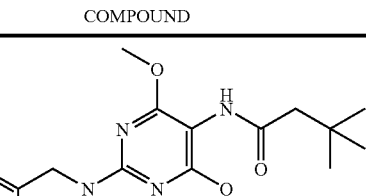 | A |

TABLE 1-continued

ACTIVITIES OF EXEMPLARY COMPOUNDS

| COMPOUND | ACTIVITY |
|---|---|
| 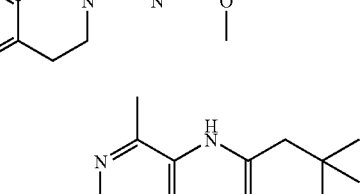 | |

What is claimed is:

1. A compound of formula IA-1a

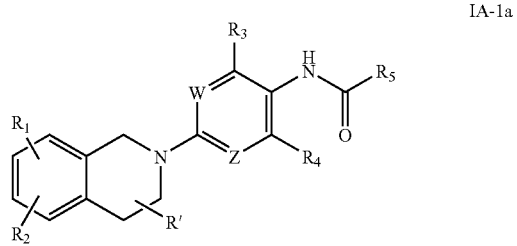

wherein $R_5$ is $C_3$-$C_6$ alkyl or $CH_2$—$C_3$—$C_6$-cycloalkyl and where $R_5$ is optionally substituted with halogen, hydroxy, or methoxy;

at least one of W and Z is N, and the other is C;

$R_1$ is H, CN, halogen, $CH_2CN$, OH, $NO_2$, $CH_2F$, $CHF_2$, $CF_3$, $CF_2CF_3$, $C_1$-$C_6$ alkyl, $C(=O)C_1$-$C_6$ alkyl, NH—$C_1$-$C_6$ alkyl, $NHC(=O)C_1$-$C_6$ alkyl, $C(=O)N(CH_3)_2$, $C(=O)N(Et)_2$, $C(=O)NH$—$C_1$-$C_6$ alkyl, $C(=O)OC_1$-$C_6$ alkyl, $OC(=O)C_1$-$C_6$ alkyl, $OC_1$-$C_6$ alkyl, $SC_1$-$C_6$ alkyl, $C_3$-$C_6$ cycloalkyl, $(CH_2)_mC_3$-$C_6$ cycloalkyl, $C_3$-$C_6$ cycloalkenyl, $(CH_2)_mC_3$-$C_6$ cycloalkenyl, $C_2$-$C_6$ alkenyl, $C_2$-$C_6$ alkynyl, $Ar_1$, $(CH_2)_mAr_1$, phenyl, pyridyl, pyrrolyl, $(CH_2)_m$imidazolyl, $(CH_2)_m$pyrazyl, furyl, thienyl, $(CH_2)_m$oxazolyl, $(CH_2)_m$isoxazolyl, $(CH_2)_m$thiazolyl, $(CH_2)_m$isothiazolyl, $(CH_2)_m$phenyl, $(CH_2)_m$pyrrolyl, $(CH_2)_m$pyridyl, or $(CH_2)_m$pyrimidyl, which cycloalkyl and said cycloalkenyl groups optionally contain one or two heteroatoms selected independently from O, N, and S, and which alkyl, cycloalkyl, cycloalkenyl, alkenyl, alkynyl, imidazolyl, pyrazyl, oxazolyl, isoxazolyl, thiazolyl, isothiazolyl, phenyl, pyrrolyl, pyridyl, or pyrimidyl groups are optionally substituted with one or two groups selected, independently, from OH, halogen, cyano, methyl, ethyl, or trifluoromethyl, where m is zero, 1, or 2;

$R_3$ and $R_4$ are, independently, H, halogen, methyl, methoxy, or trifluoromethyl;

R' and $R_2$ are, independently, H, halogen, methyl, or trifluoromethyl;

and pharmaceutically acceptable salts thereof.

2. The compound of claim 1 wherein $R_1$ is H, F, methyl, or trifluoromethyl.

3. The compound of claim 1 wherein $R_3$ and $R_4$ are, independently, H, methyl, or methoxy.

4. A compound of formula IA-1b

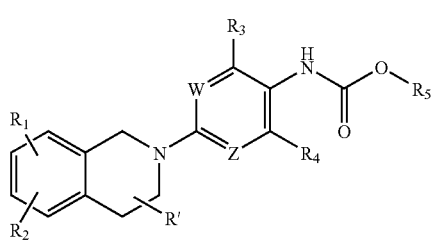

IA-1b where at least one of W and Z is N, and the other is C;

$R_1$ and $R_2$, are, independently, H, CN, halogen, $CH_2CN$, OH, $NO_2$, $CH_2F$, $CHF_2$, $CF_3$, $CF_2CF_3$, $C_1$-$C_6$ alkyl, C(=O)$C_1$-$C_6$ alkyl, NH—$C_1$-$C_6$ alkyl, NHC(=O)$C_1$-$C_6$ alkyl, C(=O)N(CH_3)_2, C(=O)N(Et)_2, C(=O)NH—$C_1$-$C_6$ alkyl, C(=O)O$C_1$-$C_6$ alkyl, OC(=O)$C_1$-$C_6$ alkyl, O$C_1$-$C_6$ alkyl, S$C_1$-$C_6$ alkyl, $C_3$-$C_6$ cycloalkyl, $(CH_2)_m$$C_3$-$C_6$ cycloalkyl, $C_3$-$C_6$ cycloalkenyl, $(CH_2)_m$$C_3$-$C_6$ cycloalkenyl, $C_2$-$C_6$ alkenyl, $C_2$-$C_6$ alkynyl, $Ar_1$, $(CH_2)_m Ar_1$, phenyl, pyridyl, pyrrolyl, $(CH_2)_m$imidazolyl, $(CH_2)_m$pyrazyl, furyl, thienyl, $(CH_2)_m$oxazolyl, $(CH_2)_m$isoxazolyl, $(CH_2)_m$thiazolyl, $(CH_2)_m$isothiazolyl, $(CH_2)_m$phenyl, $(CH_2)_m$pyrrolyl, $(CH_2)_m$pyridyl, or $(CH_2)_m$pyrimidyl, which cycloalkyl and said cycloalkenyl groups optionally contain one or two heteroatoms selected independently from O, N, and S, and which alkyl, cycloalkyl, cycloalkenyl, alkenyl, alkynyl, imidazolyl, pyrazyl, oxazolyl, isoxazolyl, thiazolyl, isothiazolyl, phenyl, pyrrolyl, pyridyl, or pyrimidyl groups are optionally substituted with one or two groups selected, independently, from OH, halogen, cyano, methyl, ethyl, or trifluoromethyl, where m is zero, 1, or 2; or $R_1$ and $R_2$, together with the ring carbon atoms to which they are attached, form a 5- or 6-member fused ring, which ring may be saturated, unsaturated, or aromatic, which optionally contains one or two heteroatoms selected independently from O, N, and S, and which is optionally substituted with halogen, $CF_3$, or $C_1$-$C_3$ alkyl;

R' is H, halogen, $CF_3$, or $C_1$-$C_3$ alkyl;

$R_3$ and $R_4$ are, independently, H, CN, halogen, $CF_3$, $OCF_3$, O$C_1$-$C_3$ alkyl, or $C_1$-$C_6$ alkyl, all said $C_1$-$C_3$ alkyl groups and said $C_1$-$C_6$ alkyl groups optionally substituted with one or two groups selected, independently, from OH, halogen, $C_1$-$C_3$ alkyl, O$C_1$-$C_3$ alkyl, or trifluoromethyl;

$R_5$ is $C_1$-$C_6$ alkyl, $(CHR_6)_w$$C_3$-$C_6$ cycloalkyl, $(CHR_6)_w$$CH_2$$C_3$-$C_6$ cycloalkyl, $CH_2(CHR_6)_w$$C_3$-$C_6$ cycloalkyl, $CR_6$=CH—$C_3$-$C_6$ cycloalkyl, CH=$CR_6$—$C_3$-$C_6$ cycloalkyl, $(CHR_6)_w$$C_5$-$C_6$ cycloalkenyl, $CH_2(CHR_6)_w$$C_5$-$C_6$ cycloalkenyl, $C_2$-$C_6$ alkenyl, $C_2$-$C_6$ alkynyl, $Ar_1$, $(CHR_6)_w Ar_1$, $CH_2(CHR_6)_w Ar_1$, or $(CHR_6)_w CH_2 Ar_1$, where w=0-3, $Ar_1$ is a 5- to 10-member mono- or bicyclic aromatic group, optionally containing 1-4 ring heteroatoms selected independently from N, O, and S; $R_6$ is hydrogen or $C_1$-$C_3$ alkyl; where all cycloalkyl and cycloalkenyl groups optionally contain one or two ring heteroatoms selected independently from N, O, and S; where all alkyl, cycloalkyl, alkenyl, cycloalkenyl, heterocycloalkyl, heterocycloalkenyl, alkynyl, aryl, and heteroaryl groups in $R_1$, $R_2$, $R_3$, $R_4$, $R_5$, $R_6$, or $Ar_1$ are optionally substituted with one or two substituents selected independently from $C_1$-$C_3$ alkyl, halogen, OH, OMe, SMe, CN, $CH_2F$, and trifluoromethyl; where, additionally, all cycloalkyl and heterocycloalkyl groups are optionally substituted with either an exocyclic carbon-carbon double bond or a carbonyl group; and where, additionally, the alkenyl and alkynyl groups are also optionally substituted with phenyl or $C_3$-$C_6$ cycloalkyl; and pharmaceutically acceptable salts thereof.

5. The compound of claim 4 wherein $R_3$ and $R_4$ are, independently, H, halogen, methyl, methoxy, or trifluoromethyl.

6. The compound of claim 5 wherein R' and $R_2$ are, independently, H, halogen, methyl, or trifluoromethyl.

7. The compound of claim 6, wherein $R_5$ is $C_3$-$C_6$ alkyl or $CH_2$—$C_3$-$C_6$-cycloalkyl and where $R_5$ is optionally substituted with halogen, hydroxy, or methoxy.

8. The compound of claim 7 wherein $R_1$ is H, F, methyl, or trifluoromethyl.

9. The compound of claim 4 wherein $R_3$ and $R_4$ are, independently, H, methyl, or methoxy.

10. A compound of formula IA2

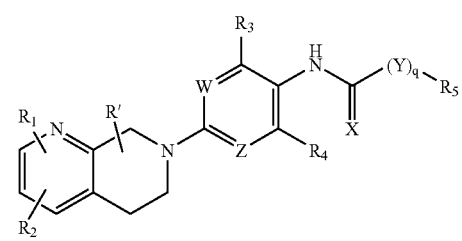

IA2 where at least one of W and Z is N, and the other is C;

$R_1$ and $R_2$, are, independently, H, CN, halogen, $CH_2CN$, OH, $NO_2$, $CH_2F$, $CHF_2$, $CF_3$, $CF_2CF_3$, $C_1$-$C_6$ alkyl, C(=O)$C_1$-$C_6$ alkyl, NH—$C_1$-$C_6$ alkyl, NHC(=O)$C_1$-$C_6$ alkyl, C(=O)N(CH_3)_2, C(=O)N(Et)_2, C(=O)NH—$C_1$-$C_6$ alkyl, C(=O)O$C_1$-$C_6$ alkyl, OC(=O)$C_1$-$C_6$ alkyl, O$C_1$-$C_6$ alkyl, S$C_1$-$C_6$ alkyl, $C_3$-$C_{66}$ cycloalkyl, $(CH_2)_m$$C_3$-$C_6$ cycloalkyl, $C_3$-$C_6$ cycloalkenyl, $(CH_2)_m$$C_3$-$C_6$ cycloalkenyl, $C_2$-$C_6$ alkenyl, $C_2$-$C_6$ alkynyl, $Ar_1$, $(CH_2)_m Ar_1$, phenyl, pyridyl, pyrrolyl, $(CH_2)_m$imidazolyl, $(CH_2)_m$pyrazyl, furyl, thienyl, $(CH_2)_m$oxazolyl, $(CH_2)_m$isoxazolyl, $(CH_2)_m$thiazolyl, $(CH_2)_m$isothiazolyl, $(CH_2)_m$phenyl, $(CH_2)_m$pyrrolyl, $(CH_2)_m$pyridyl, or $(CH_2)_m$pyrimidyl, which cycloalkyl and said cycloalkenyl groups optionally contain one or two heteroatoms selected independently from O, N, and S, and which alkyl, cycloalkyl, cycloalkenyl, alkenyl, alkynyl, imidazolyl, pyrazyl, oxazolyl, isoxazolyl, thiazolyl, isothiazolyl, phenyl, pyrrolyl, pyridyl, or pyrimidyl groups are optionally substituted with one or two groups selected, independently, from OH, halogen, cyano, methyl, ethyl, or trifluoromethyl, where m is zero, 1, or 2; or $R_1$ and $R_2$, together with the ring carbon atoms to which they are attached, form a 5- or 6-member fused ring, which ring may be saturated, unsaturated, or aromatic, which optionally contains one or two heteroatoms selected independently from O, N, and S, and which is optionally substituted with halogen, $CF_3$, or $C_1$-$C_3$ alkyl;

R' is H, halogen, $CF_3$, or $C_1$-$C_3$ alkyl;

$R_3$ and $R_4$ are, independently, H, CN, halogen, $CF_3$, $OCF_3$, $OC_1$-$C_3$ alkyl, or $C_1$-$C_6$ alkyl, all said $C_1$-$C_3$ alkyl groups and said $C_1$-$C_6$ alkyl groups optionally substituted with one or two groups selected, independently, from OH, halogen, $C_1$-$C_3$ alkyl, $OC_1$-$C_3$ alkyl, or trifluoromethyl;

X=O or S; Y is O or S; q=1 or 0;

$R_5$ is $C_1$-$C_6$ alkyl, $(CHR_6)_w C_3$-$C_6$ cycloalkyl, $(CHR_6)_w CH_2C_3$-$C_6$ cycloalkyl, $CH_2(CHR_6)_w C_3$-$C_6$ cycloalkyl, $CR_6$=CH—$C_3$-$C_6$ cycloalkyl, CH=$CR_6$—$C_3$-$C_6$ cycloalkyl, $(CHR_6)_w C_5$-$C_6$ cycloalkenyl, $CH_2(CHR_6)_w C_5$-$C_6$ cycloalkenyl, $C_2$-$C_6$ alkenyl, $C_2$-$C_6$ alkynyl, $Ar_1$, $(CHR_6)_w Ar_1$, $CH_2(CHR_6)_w Ar_1$, or $(CHR_6)_w CH_2 Ar_1$, where w=0-3, $Ar_1$ is a 5- to 10-member mono- or bicyclic aromatic group, optionally containing 1-4 ring heteroatoms selected independently from N, O, and S; $R_6$ is hydrogen or $C_1$-$C_3$ alkyl; where all cycloalkyl and cycloalkenyl groups optionally contain one or two ring heteroatoms selected independently from N, O, and S; where all alkyl, cycloalkyl, alkenyl, cycloalkenyl, heterocycloalkyl, heterocycloalkenyl, alkynyl, aryl, and heteroaryl groups in $R_1$, $R_2$, $R_3$, $R_4$, $R_5$, $R_6$, or $Ar_1$ are optionally substituted with one or two substituents selected independently from $C_1$-$C_3$ alkyl, halogen, OH, OMe, SMe, CN, $CH_2F$, and trifluoromethyl; where, additionally, all cycloalkyl and heterocycloalkyl groups are optionally substituted with either an exocyclic carbon-carbon double bond or a carbonyl group; and where, additionally, the alkenyl and alkynyl groups are also optionally substituted with phenyl or $C_3$-$C_6$ cycloalkyl; and pharmaceutically acceptable salts thereof.

11. The compound of claim 10 wherein X is O, Y is O, and q is 0 or 1.

12. The compound of claim 11 wherein $R_3$ and $R_4$ are, independently, H, halogen, methyl, methoxy, or trifluoromethyl.

13. The compound of claim 12 wherein R' and $R_2$ are, independently, H, halogen, methyl, or trifluoromethyl.

14. The compound of claim 13, wherein $R_5$ is $C_3$-$C_6$ alkyl or $CH_2$—$C_3$-$C_6$-cycloalkyl and where $R_5$ is optionally substituted with halogen, hydroxy, or methoxy.

15. The compound of claim 14 wherein $R_1$ is H, F, methyl, or trifluoromethyl.

16. The compound claim 11 wherein $R_3$ and $R_4$ are, independently, H, methyl, or methoxy.

17. A compound of formula IA3

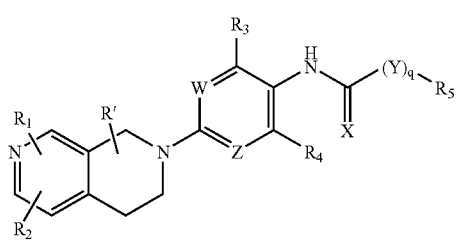

IA3 where at least one of W and Z is N, and the other is C;

$R_1$ and $R_2$, are, independently, H, CN, halogen, $CH_2CN$, OH, $NO_2$, $CH_2F$, $CHF_2$, $CF_3$, $CF_2CF_3$, $C_1$-$C_6$ alkyl, C(=O)$C_1$-$C_6$ alkyl, NH—$C_1$-$C_6$ alkyl, NHC(=O)$C_1$-$C_6$ alkyl, C(=O)N($CH_3$)$_2$, C(=O)N(Et)$_2$, C(=O)NH—$C_1$-$C_6$ alkyl, C(=O)O$C_1$-$C_6$ alkyl, OC(=O)$C_1$-$C_6$ alkyl, O$C_1$-$C_6$ alkyl, S$C_1$-$C_6$ alkyl, $C_3$-$C_6$ cycloalkyl, $(CH_2)_m C_3$-$C_6$ cycloalkyl, $C_3$-$C_6$ cycloalkenyl, $(CH_2)_m C_3$-$C_6$ cycloalkenyl, $C_2$-$C_6$ alkenyl, $C_2$-$C_6$ alkynyl, $Ar_1$, $(CH_2)_m Ar_1$, phenyl, pyridyl, pyrrolyl, $(CH_2)_m$imidazolyl, $(CH_2)_m$pyrazyl, furyl, thienyl, $(CH_2)_m$oxazolyl, $(CH_2)_m$isoxazolyl, $(CH_2)_m$thiazolyl, $(CH_2)_m$isothiazolyl, $(CH_2)_m$phenyl, $(CH_2)_m$pyrrolyl, $(CH_2)_m$pyridyl, or $(CH_2)_m$pyrimidyl, which cycloalkyl and said cycloalkenyl groups optionally contain one or two heteroatoms selected independently from O, N, and S, and which alkyl, cycloalkyl, cycloalkenyl, alkenyl, alkynyl, imidazolyl, pyrazyl, oxazolyl, isoxazolyl, thiazolyl, isothiazolyl, phenyl, pyrrolyl, pyridyl, or pyrimidyl groups are optionally substituted with one or two groups selected, independently, from OH, halogen, cyano, methyl, ethyl, or trifluoromethyl, where m is zero, 1, or 2; or $R_1$ and $R_2$, together with the ring carbon atoms to which they are attached, form a 5- or 6-member fused ring, which ring may be saturated, unsaturated, or aromatic, which optionally contains one or two heteroatoms selected independently from O, N, and S, and which is optionally substituted with halogen, $CF_3$, or $C_1$-$C_3$ alkyl;

R' is H, halogen, $CF_3$, or $C_1$-$C_3$ alkyl;

$R_3$ and $R_4$ are, independently, H, CN, halogen, $CF_3$, $OCF_3$, $OC_1$-$C_3$ alkyl, or $C_1$-$C_6$ alkyl, all said $C_1$-$C_3$ alkyl groups and said $C_1$-$C_6$ alkyl groups optionally substituted with one or two groups selected, independently, from OH, halogen, $C_1$-$C_3$ alkyl, $OC_1$-$C_3$ alkyl, or trifluoromethyl;

X=O or S; Y is O or S; q=1 or 0;

$R_5$ is $C_1$-$C_6$ alkyl, $(CHR_6)_w C_3$-$C_6$ cycloalkyl, $(CHR_6)_w CH_2C_3$-$C_6$ cycloalkyl, $CH_2(CHR_6)_w C_3$-$C_6$ cycloalkyl, $CR_6$=CH—$C_3$-$C_6$ cycloalkyl, CH=$CR_6$—$C_3$-$C_6$ cycloalkyl, $(CHR_6)_w C_5$-$C_6$ cycloalkenyl, $CH_2(CHR_6)_w C_5$-$C_6$ cycloalkenyl, $C_2$-$C_6$ alkenyl, $C_2$-$C_6$ alkynyl, $Ar_1$, $(CHR_6)_w Ar_1$, $CH_2(CHR_6)_w Ar_1$, or $(CHR_6)_w CH_2 Ar_1$, where w=0-3, $Ar_1$ is a 5- to 10-member mono- or bicyclic aromatic group, optionally containing 1-4 ring heteroatoms selected independently from N, O, and S; $R_6$ is hydrogen or $C_1$-$C_3$ alkyl; where all cycloalkyl and cycloalkenyl groups optionally contain one or two ring heteroatoms selected independently from N, O, and S; where all alkyl, cycloalkyl, alkenyl, cycloalkenyl, heterocycloalkyl, heterocycloalkenyl, alkynyl, aryl, and heteroaryl groups in $R_1$, $R_2$, $R_3$, $R_4$, $R_5$, $R_6$, or $Ar_1$ are optionally substituted with one or two substituents selected independently from $C_1$-$C_3$ alkyl, halogen, OH, OMe, SMe, CN, $CH_2F$, and trifluoromethyl; where, additionally, all cycloalkyl and heterocycloalkyl groups are optionally substituted with either an exocyclic carbon-carbon double bond or a carbonyl group; and where, additionally, the alkenyl and alkynyl groups are also optionally substituted with phenyl or $C_3$-$C_6$ cycloalkyl; and pharmaceutically acceptable salts thereof.

18. The compound of claim 17 wherein X is O, Y is O, and q is 0 or 1.

19. The compound of claim 18 wherein $R_3$ and $R_4$ are, independently, H, halogen, methyl, methoxy, or trifluoromethyl.

20. The compound of claim 19 wherein R' and $R_2$ are, independently, H, halogen, methyl, or trifluoromethyl.

21. The compound of claim 20, wherein $R_5$ is $C_3$-$C_6$ alkyl or $CH_2$—$C_3$-$C_6$-cycloalkyl and where $R_5$ is optionally substituted with halogen, hydroxy, or methoxy.

22. The compound of claim 21 wherein $R_1$ is H, F, methyl, or trifluoromethyl.

23. The compound of claim 17 wherein $R_3$ and $R_4$ are, independently, H, methyl, or methoxy.

24. A compound of formula IA4

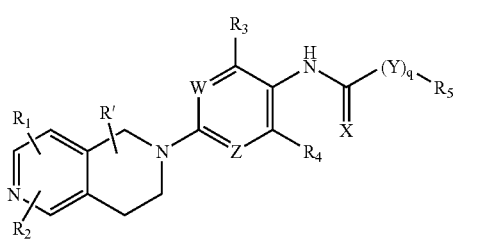

where at least one of W and Z is N, and the other is C;

$R_1$ and $R_2$, are, independently, H, CN, halogen, $CH_2CN$, OH, $NO_2$, $CH_2F$, $CHF_2$, $CF_3$, $CF_2CF_3$, $C_1$-$C_6$ alkyl, $C(=O)C_1$-$C_6$ alkyl, NH—$C_1$-$C_6$ alkyl, NHC(=O)$C_1$-$C_6$ alkyl, $C(=O)N(CH_3)_2$, $C(=O)N(Et)_2$, $C(=O)$NH—$C_1$-$C_6$ alkyl, $C(=O)OC_1$-$C_6$ alkyl, $OC(=O)C_1$-$C_6$ alkyl, $OC_1$-$C_6$ alkyl, $SC_1$-$C_6$ alkyl, $C_3$-$C_6$ cycloalkyl, $(CH_2)_mC_3$-$C_6$ cycloalkyl, $C_3$-$C_6$ cycloalkenyl, $(CH_2)_m$ $C_3$-$C_6$ cycloalkenyl, $C_2$-$C_6$ alkenyl, $C_2$-$C_6$ alkynyl, $Ar_1$, $(CH_2)_mAr_1$, phenyl, pyridyl, pyrrolyl, $(CH_2)_m$imidazolyl, $(CH_2)_m$pyrazyl, furyl, thienyl, $(CH_2)_m$oxazolyl, $(CH_2)_m$isoxazolyl, $(CH_2)_m$thiazolyl, $(CH_2)_m$isothiazolyl, $(CH_2)_m$phenyl, $(CH_2)_m$pyrrolyl, $(CH_2)_m$pyridyl, or $(CH_2)_m$pyrimidyl, which cycloalkyl and said cycloalkenyl groups optionally contain one or two heteroatoms selected independently from O, N, and S, and which alkyl, cycloalkyl, cycloalkenyl, alkenyl, alkynyl, imidazolyl, pyrazyl, oxazolyl, isoxazolyl, thiazolyl, isothiazolyl, phenyl, pyrrolyl, pyridyl, or pyrimidyl groups are optionally substituted with one or two groups selected, independently, from OH, halogen, cyano, methyl, ethyl, or trifluoromethyl, where m is zero, 1, or 2; or $R_1$ and $R_2$, together with the ring carbon atoms to which they are attached, form a 5- or 6-member fused ring, which ring may be saturated, unsaturated, or aromatic, which optionally contains one or two heteroatoms selected independently from O, N, and S, and which is optionally substituted with halogen, $CF_3$, or $C_1$-$C_3$ alkyl;

R' is H, halogen, $CF_3$, or $C_1$-$C_3$ alkyl;

$R_3$ and $R_4$ are, independently, H, CN, halogen, $CF_3$, $OCF_3$, $OC_1$-$C_3$ alkyl, or $C_1$-$C_6$ alkyl, all said $C_1$-$C_3$ alkyl groups and said $C_1$-$C_6$ alkyl groups optionally substituted with one or two groups selected, independently, from OH, halogen, $C_1$-$C_3$ alkyl, $OC_1$-$C_3$ alkyl, or trifluoromethyl;

X=O or S; Y is O or S; q=1 or 0;

$R_5$ is $C_1$-$C_6$ alkyl, $(CHR_6)_wC_3$-$C_6$ cycloalkyl, $(CHR_6)_w$ $CH_2C_3$-$C_6$ cycloalkyl, $CH_2(CHR_6)_wC_3$-$C_6$ cycloalkyl, $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_w$ $C_5$-$C_6$ cycloalkenyl, $C_2$-$C_6$ alkenyl, $C_2$-$C_6$ alkynyl, $Ar_1$, $(CHR_6)_wAr_1$, $CH_2(CHR_6)_wAr_1$, or $(CHR_6)_wCH_2Ar_1$, where w=0-3, $Ar_1$ is a 5- to 10-member mono- or bicyclic aromatic group, optionally containing 1-4 ring heteroatoms selected independently from N, O, and S; $R_6$ is hydrogen or $C_1$-$C_3$ alkyl; where all cycloalkyl and cycloalkenyl groups optionally contain one or two ring heteroatoms selected independently from N, O, and S; where all alkyl, cycloalkyl, alkenyl, cycloalkenyl, heterocycloalkyl, heterocycloalkenyl, alkynyl, aryl, and heteroaryl groups in $R_1$, $R_2$, $R_3$, $R_4$, $R_5$, $R_6$, or $Ar_1$ are optionally substituted with one or two substituents selected independently from $C_1$-$C_3$ alkyl, halogen, OH, OMe, SMe, CN, $CH_2F$, and trifluoromethyl; where, additionally, all cycloalkyl and heterocycloalkyl groups are optionally substituted with either an exocyclic carbon-carbon double bond or a carbonyl group; and where, additionally, the alkenyl and alkynyl groups are also optionally substituted with phenyl or $C_3$-$C_6$ cycloalkyl; and pharmaceutically acceptable salts thereof.

25. The compound of claim 24 wherein X is O, Y is O, and q is 0 or 1.

26. The compound of claim 25 wherein $R_3$ and $R_4$ are, independently, H, halogen, methyl, methoxy, or trifluoromethyl.

27. The compound of claim 26 wherein R' and $R_2$ are, independently, H, halogen, methyl, or trifluoromethyl.

28. The compound of claim 27, wherein $R_5$ is $C_3$-$C_6$ alkyl or $CH_2$—$C_3$-$C_6$-cycloalkyl and where $R_5$ is optionally substituted with halogen, hydroxy, or methoxy.

29. The compound of claim 28 wherein $R_1$ is H, F, methyl, or trifluoromethyl.

30. The compound of claim 24 wherein $R_3$ and $R_4$ are, independently, H, methyl, or methoxy.

31. A compound of formula IA5

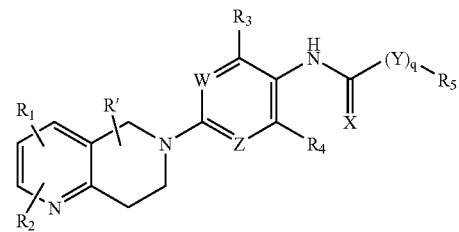

where at least one of W and Z is N, and the other is C;

$R_1$ and $R_2$, are, independently, H, CN, halogen, $CH_2CN$, OH, $NO_2$, $CH_2F$, $CHF_2$, $CF_3$, $CF_2CF_3$, $C_1$-$C_6$ alkyl, $C(=O)C_1$-$C_6$ alkyl, NH—$C_1$-$C_6$ alkyl, NHC(=O)$C_1$-$C_6$ alkyl, $C(=O)N(CH_3)_2$, $C(=O)N(Et)_2$, $C(=O)$NH—$C_1$-$C_6$ alkyl, $C(=O)OC_1$-$C_6$ alkyl, $OC(=O)C_1$-$C_6$ alkyl, $OC_1$-$C_6$ alkyl, $SC_1$-$C_6$ alkyl, $C_3$-$C_6$ cycloalkyl, $(CH_2)_mC_3$-$C_6$ cycloalkyl, $C_3$-$C_6$ cycloalkenyl, $(CH_2)_m$ $C_3$-$C_6$ cycloalkenyl, $C_2$-$C_6$ alkenyl, $C_2$-$C_6$ alkynyl, $Ar_1$, $(CH_2)_mAr_1$, phenyl, pyridyl, pyrrolyl, $(CH_2)_m$imidazolyl, $(CH_2)_m$pyrazyl, furyl, thienyl, $(CH_2)_m$oxazolyl, $(CH_2)_m$isoxazolyl, $(CH_2)_m$thiazolyl, $(CH_2)_m$isothiazolyl, $(CH_2)_m$phenyl, $(CH_2)_m$pyrrolyl, $(CH_2)_m$pyridyl, or $(CH_2)_m$pyrimidyl, which cycloalkyl and said cycloalkenyl groups optionally contain one or two heteroatoms selected independently from O, N, and S, and which alkyl, cycloalkyl, cycloalkenyl, alkenyl, alkynyl, imidazolyl, pyrazyl, oxazolyl, isoxazolyl, thiazolyl, isothiazolyl, phenyl, pyrrolyl, pyridyl, or pyrimidyl groups are optionally substituted with one or two groups selected, independently, from OH, halogen, cyano, methyl, ethyl, or trifluoromethyl, where m is zero, 1, or 2; or $R_1$ and $R_2$, together with the ring carbon atoms to which they are attached, form a 5- or 6-member fused ring, which ring may be saturated, unsaturated, or aromatic, which optionally contains one or two heteroatoms selected independently from O, N, and S, and which is optionally substituted with halogen, $CF_3$, or $C_1$-$C_3$ alkyl;

R' is H, halogen, $CF_3$, or $C_1$-$C_3$ alkyl;

$R_3$ and $R_4$ are, independently, H, CN, halogen, $CF_3$, $OCF_3$, $OC_1$-$C_3$ alkyl, or $C_1$-$C_6$ alkyl, all said $C_1$-$C_3$ alkyl groups and said $C_1$-$C_6$ alkyl groups optionally substituted with one or two groups selected, independently, from OH, halogen, $C_1$-$C_3$ alkyl, $OC_1$-$C_3$ alkyl, or trifluoromethyl; X=O or S; Y is O or S; q=1 or 0;

$R_5$ is $C_1$-$C_6$ alkyl, $(CHR_6)_wC_3$-$C_6$ cycloalkyl, $(CHR_6)_wCH_2C_3$-$C_6$ cycloalkyl, $CH_2(CHR_6)_wC_3$-$C_6$ cycloalkyl, $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, $C_2$-$C_6$ alkynyl, $Ar_1$, $(CHR_6)_wAr_1$, $CH_2(CHR_6)_wAr_1$, or $(CHR_6)_wCH_2Ar_1$, where w=0-3, $Ar_1$ is a 5- to 10-member mono- or bicyclic aromatic group, optionally containing 1-4 ring heteroatoms selected independently from N, O, and S; $R_6$ is hydrogen or $C_1$-$C_3$ alkyl; where all cycloalkyl and cycloalkenyl groups optionally contain one or two ring heteroatoms selected independently from N, O, and S; where all alkyl, cycloalkyl, alkenyl, cycloalkenyl, heterocycloalkyl, heterocycloalkenyl, alkynyl, aryl, and heteroaryl groups in $R_1$, $R_2$, $R_3$, $R_4$, $R_5$, $R_6$, or $Ar_1$ are optionally substituted with one or two substituents selected independently from $C_1$-$C_3$ alkyl, halogen, OH, OMe, SMe, CN, $CH_2F$, and trifluoromethyl; where, additionally, all cycloalkyl and heterocycloalkyl groups are optionally substituted with either an exocyclic carbon-carbon double bond or a carbonyl group; and where, additionally, the alkenyl and alkynyl groups are also optionally substituted with phenyl or $C_3$-$C_6$ cycloalkyl; and
pharmaceutically acceptable salts thereof.

32. The compound of claim 31 wherein X is O, Y is O, and q is 0 or 1.

33. The compound of claim 32 wherein $R_3$ and $R_4$ are, independently, H, halogen, methyl, methoxy, or trifluoromethyl.

34. The compound of claim 33 wherein R' and $R_2$ are, independently, H, halogen, methyl, or trifluoromethyl.

35. The compound of claim 34, wherein $R_5$ is $C_3$-$C_6$ alkyl or $CH_2$—$C_3$-$C_6$-cycloalkyl and where $R_5$ is optionally substituted with halogen, hydroxy, or methoxy.

36. The compound of claim 35 wherein $R_1$ is H, F, methyl, or trifluoromethyl.

37. The compound of claim 31 wherein $R_3$ and $R_4$ are, independently, H, methyl, or methoxy.

38. A pharmaceutical composition comprising a compound of claim 1 with a pharmaceutically acceptable carrier.

39. A pharmaceutical composition comprising a compound of claim 4 with a pharmaceutically acceptable carrier.

40. A pharmaceutical composition comprising a compound of claim 10 with a pharmaceutically acceptable carrier.

41. A pharmaceutical composition comprising a compound of claim 17 with a pharmaceutically acceptable carrier.

42. A pharmaceutical composition comprising a compound of claim 24 with a pharmaceutically acceptable carrier.

43. A pharmaceutical composition comprising a compound of claim 31 with a pharmaceutically acceptable carrier.

* * * * *